United States Patent
Ridinger et al.

(10) Patent No.: US 11,957,677 B2
(45) Date of Patent: Apr. 16, 2024

(54) CANCER TREATMENT USING FGFR INHIBITORS AND PLK1 INHIBITORS

(71) Applicant: Cardiff Oncology, Inc., San Diego, CA (US)

(72) Inventors: Maya Ridinger, San Diego, CA (US); Mark Erlander, San Diego, CA (US); Anju Karki, San Diego, CA (US)

(73) Assignee: Cardiff Oncology, Inc., San Diego, CA (US)

( * ) Notice: Subject to any disclaimer, the term of this patent is extended or adjusted under 35 U.S.C. 154(b) by 0 days.

(21) Appl. No.: 18/046,648

(22) Filed: Oct. 14, 2022

(65) Prior Publication Data
US 2023/0124366 A1 Apr. 20, 2023

Related U.S. Application Data

(60) Provisional application No. 63/256,407, filed on Oct. 15, 2021.

(51) Int. Cl.
| | |
|---|---|
| *A61K 31/496* | (2006.01) |
| *A61K 31/506* | (2006.01) |
| *A61K 31/519* | (2006.01) |
| *A61K 35/00* | (2006.01) |
| *A61P 35/00* | (2006.01) |

(52) U.S. Cl.
CPC .......... *A61K 31/496* (2013.01); *A61K 31/506* (2013.01); *A61K 31/519* (2013.01); *A61P 35/00* (2018.01)

(58) Field of Classification Search
CPC ..... A61P 35/00; A61K 31/496; A61K 31/506; A61K 31/519; A61K 31/5025; A61K 31/517; A61K 31/5377; A61K 9/2013; C12Q 1/485; C12Q 2600/118; C12Q 1/6886; C12Y 207/10001; G01N 2800/52
See application file for complete search history.

(56) References Cited

U.S. PATENT DOCUMENTS

| | | |
|---|---|---|
| 7,737,149 B2 | 6/2010 | Buttar et al. |
| 8,927,530 B2 | 1/2015 | Valsasina et al. |

FOREIGN PATENT DOCUMENTS

| | | | |
|---|---|---|---|
| WO | WO2008/075068 | 6/2008 | |
| WO | WO2021/146322 | 1/2021 | |
| WO | WO-2021138392 A1 * | 7/2021 | ............... A61P 35/00 |

OTHER PUBLICATIONS

Golub, T. R., et. al., Molecular classification of cancer: class discovery and class prediction by gene expression monitoring, 1999, Science., vol. 286, Issue 5439, 531-537. (Year: 1999).*
Sero, V., et. al., Targeting polo-like kinase 1 by NMS-P937 in osteosarcoma cell lines inhibits tumor cell growth and partially overcomes drug resistance., 2014, Invest. New Drugs, vol. 32, 1167-1180. (Year: 2014).*
Gleixner, K. V., et. al., Polo-like Kinase 1 (Plk1) as a Novel Drug Target in Chronic Myeloid Leukemia: Overriding Imatinib Resistance with the Plk1 Inhibitor BI 2536., 2010, vol. 70, Issue 4, 1513-1523. (Year: 2010).*
Rothman, N., The use of common genetic polymorphisms to enhance the epidemiologic study of environmental carcinogens, 2001, Biochimica et Biophysica Acta (BBA)—Reviews on Cancer, vol. 1471, Issue 2, C1-C10. (Year: 2001).*
Li, F., et. al., FGFR-Mediated Reactivation of MAPK Signaling Attenuates Antitumor Effects of Imatinib in Gastrointestinal Stromal Tumors., Cancer Discov., 2015, vol. 5, Issue 4, 438-451. (Year: 2015).*
Bartova, A and Trckova et a. WO-2022040111-A2-NPL Document, 2022, pp. 1-9. (Year 2022).*
Dai et al., "Fibroblast growth factor receptors (FGFRs): structures and small molecule inhibitors," Cells 2019, 8(6), in 15 pages.
Gavine et al., "AZD4547: an orally bioavailable, potent, and selective inhibitor of the fibroblast growth factor receptor tyrosine kinase family," Cancer Research 2012, 72(8), 2045-2056.
Krook et al., "Fibroblast growth factor receptors in cancer: genetic alterations, diagnostics, therapeutic targets and mechanisms of resistance," British Journal of Cancer 2021, 124(5), 880-892.
Pacini et al., "Targeting the fibroblast growth factor receptor (FGFR) family in lung cancer," Cells 2021, 10(5), in 22 pages.
Yang et al., "CRISPR-mediated kinome editing prioritizes a synergistic combination therapy for FGFR1-amplified lung cancer," Cancer Research 2021, 81(11), 3121-3133.

* cited by examiner

*Primary Examiner* — Joseph R Kosack
*Assistant Examiner* — Quincy A McKoy
(74) *Attorney, Agent, or Firm* — Sheppard, Mullin, Richter & Hampton LLP

(57) ABSTRACT

Provided include methods, compositions and kits for treating cancer in a subject. The method can comprise administrating an FGFR inhibitor (for example, AZD4547) and a PLK1 inhibitor (for example, onvansertib) to the subject in a manner sufficient to inhibit progression of the cancer.

18 Claims, 30 Drawing Sheets

FIG. 13

Bliss synergy and antagonism

CANCER TREATMENT USING FGFR INHIBITORS AND PLK1 INHIBITORS

RELATED APPLICATIONS

This application claims the benefit under 35 U.S.C. § 119(e) of U.S. Provisional Patent Application No. 63/256,407, filed Oct. 15, 2021; the content of this related application is incorporated herein by reference in its entirety for all purposes.

BACKGROUND

Field

The present application generally relates to treatment for cancer. More specifically, combination therapies for treating cancer using fibroblast growth factor receptor (FGFR) inhibitors in combination with polo-like kinase 1 (PLK1) inhibitors are provided.

Description of the Related Art

Polo-like kinase 1 (PLK1) is a well-characterized member of the 5 members of the family of serine/threonine protein kinases and strongly promotes the progression of cells through mitosis. PLK1 performs several important functions throughout the mitotic (M) phase of the cell cycle, including the regulation of centrosome maturation and spindle assembly, the removal of cohesins from chromosome arms, the inactivation of anaphase-promoting complex/cyclosome (APC/C) inhibitors, and the regulation of mitotic exit and cytokinesis. PLK1 plays a key role in centrosome functions and the assembly of bipolar spindles. PLK1 also acts as a negative regulator of p53 family members leading to ubiquitination and subsequent degradation of p53/TP53, inhibition of the p73/TP73 mediated pro-apoptotic functions and phosphorylation/degradation of bora, a cofactor of Aurora kinase A. During the various stages of mitosis, PLK1 localizes to the centrosomes, kinetochores and central spindle. PLK1 is a master regulator of mitosis and aberrantly overexpressed in a variety of human cancers including AML and is correlated with cellular proliferation and poor prognosis.

FGFR inhibitors are inhibitors of fibroblast growth factor receptors (FGFRs). FGFRs are receptor tyrosine kinase (RTK) that regulate a variety of biological processes. FGFR signaling is frequently deregulated in cancers, most often because of FGFR alterations such as gene amplifications, point mutations, and fusions as well as of epigenetic and/or transcriptional deregulation. FGFR-targeted therapies have been limited by their lack of activity in a majority of FGFR-altered cancers as well as by acquired resistance of initially responding tumors.

There is a need to develop effective treatments for cancer patients, including patients with FGFR-altered tumors and/or patients resistant to FGFR inhibitor treatment.

SUMMARY

Provided herein include methods, compositions and kits for treating cancer. Some embodiments provide a method of treating cancer comprises administrating a fibroblast growth factor receptor (FGFR) inhibitor and a Polo-like kinase 1 (PLK1) inhibitor to a subject with cancer, thereby inhibiting cancer progression. In some embodiments, the subject has head and neck cancer (e.g., head and neck squamous cell carcinoma), lung cancer (e.g., non-small cell lung cancer and small-cell lung cancer), intrahepatic cholangiocarcinoma (iCCA), gastric cancer, urothelial cancer, endometrial cancer, cervical cancer, rhabdomyosarcoma, cholangiocarcinoma, glioblastoma, low-grade glioma, ovarian cancer, prostate adenocarcinoma, thyroid carcinoma, endometrial cancer, gallbladder cancer, breast cancer or a combination thereof. The cancer can be FGFR-altered cancer. In some embodiments, the subject is human. In some embodiments, the subject is a patient with FGFR-altered tumors (e.g., FGFR-amplified tumors). For example, the patient can have fibroblast growth factor receptor 1 (FGFR1)-amplified cancer, including but not limited to FGFR1-amplified breast cancer, FGFR1-amplified lung cancer, and FGFR1-amplified colon cancer. The patient can have FGFR2-amplified cancer, including but not limited to FGFR2-amplified gastric cancer, and FGFR2-amplified gastroesophageal cancer. In some embodiments, the subject is resistant to, or has been developed resistance to, FGFR inhibitor treatment alone. The patient's resistance to FGFR inhibitor treatment can be partial lack of response, or a complete lack of response to the FGFR inhibitor treatment alone.

Disclosed herein include compositions and kits for treating cancer. In some embodiments, the kit comprises: a PLK1 inhibitor; and a manual providing instructions for co-administrating the PLK1 inhibitor with an FGFR inhibitor to a subject in need thereof for treating cancer. In some embodiments, the kit comprises the FGFR inhibitor. The PLK1 inhibitor can be, for example, onvansertib. The FGFR inhibitor can be, for example, AZD4547 (N-[5-[2-(3,5-Dimethoxyphenyl)ethyl]-2H-pyrazol-3-yl]-4-(3,5-diemthylpiperazin-1-yl)benzamide). In some embodiments, the instructions comprise instructions for administering onvansertib to the subject at 8 mg/m$^2$-90 mg/m$^2$. In some embodiments, the FGFR inhibitor is AZD4547 and the PLK1 inhibitor is onvansertib.

Also disclosed herein include a method of sensitizing cancer cells to cancer treatment using one or more FGFR inhibitors. The method can, for example, comprises contacting cancer cells with a composition comprising a PLK1 inhibitor (e.g., onvansertib, or a pharmaceutically acceptable salt, solvate, stereoisomer thereof, thereby sensitizing the cancer cells to one or more FGFR inhibitors (e.g., AZD4547).

BRIEF DESCRIPTION OF THE DRAWINGS

FIG. 6A-B depict dose-response curves of NCI-H1703 cell line (A) and NCI-H520 cell line (B) when treated with AZD4547 alone or onvansertib in combination with different doses of AZD4547. Following drug co-treatment, the observed cell viability is compared to the results expected from simple drug additivity according to the Bliss independence model (BLISS, 1939). Synergistic effects are defined as the difference between the expected and observed responses, which can then be analyzed in terms of greater-than-expected sensitivity to one of the drug components. FIG. 6C-D depict the synergy distribution onto the dose-response surface of onvansertib and AZD4547 based on the Bliss model in NCI-H1703 cells (C) and NCI-H520 cells (D). FIG. 6E-F depicts the synergy distribution of onvansertib and AZD4547 based on the Bliss model in NCI-H1703 cells (E) and NCI-H520 (F), using a different gradient scale.

FIG. 10 shows the concentration of AZD4547 in logarithm.

FIG. 13 depicts non-limiting exemplary embodiments and data related to Bliss synergy combination matrix of onvansertib and AZD4547 in NCI-H520 cell line, in a 2D view using the same gradient scale as FIG. 6D. The scores shown in the boxes are synergy scores. Asterisk(s) (*, , or *) indicate that the corresponding score is significant (* $P<5\times10^{-2}$,  $P<10^{-3}$, and * $P<10^{-4}$).

FIG. 16 shows the concentration of AZD4547 in logarithm.

FIG. 19 depicts non-limiting exemplary embodiments and data related to Bliss synergy combination matrix of onvansertib and AZD4547 in the gastric cancer SNU16 cell line (which as a FGFR2 amplification). The scores shown in the boxes are synergy scores. Asterisk(s) (*, , or *) indicate that the corresponding score is significant (* $P<5\times10^{-2}$,  $P<10^{-3}$, and * $P<10^{-4}$).

FIG. 20 depicts non-limiting exemplary embodiments and data related to Bliss synergy combination matrix of onvansertib and Erdafitinib in SNU16 cell line. The scores shown in the boxes are synergy scores. Asterisk(s) (*, , or *) indicate that the corresponding score is significant (* $P<5\times10^{-2}$,  $P<10^{-3}$, and * $P<10^{-4}$).

DETAILED DESCRIPTION

Figure 1:
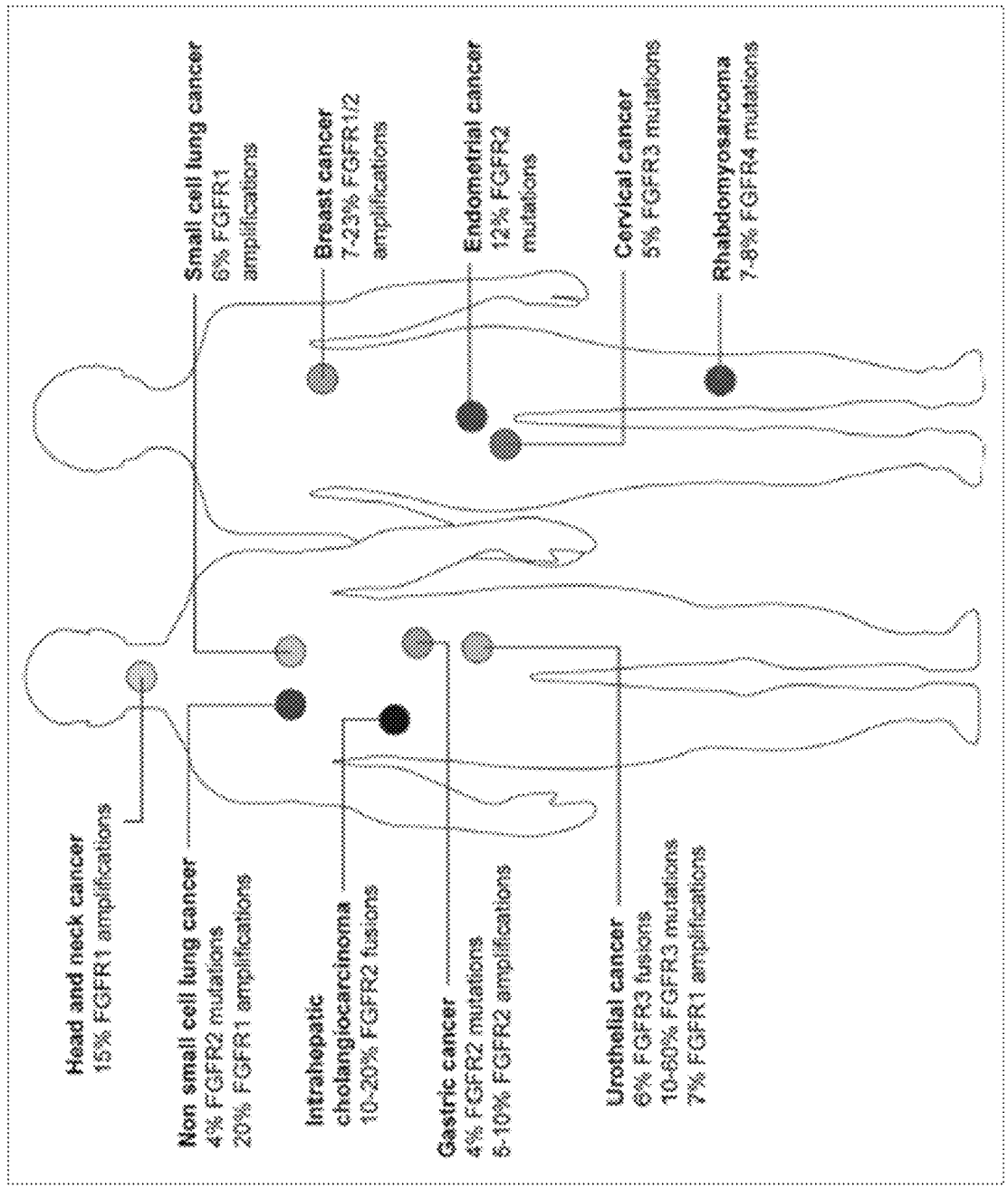
FIG. 1 depicts a non-limiting schematic illustration showing cancer types that harbor alterations in FGFR. This figure is reproduced from Krook et al., *Br. J. Cancer,* 2021, 124, 880.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Onvansertib (also known as PCM-075, NMS-1286937, NMS-937, "compound of formula (I)" in U.S. Pat. No. 8,927,530; IUPAC name 1-(2-hydroxyethyl)-8-{[5-(4-methylpiperazin-1-yl)-2-(trifluoromethoxy) phenyl] amino}-4,5-dihydro-1H-pyrazolo[4,3-h] quinazoline-3-carboxamide) is the first PLK1 specific ATP competitive inhibitor administered by oral route to enter clinical trials with proven antitumor activity in different preclinical models.

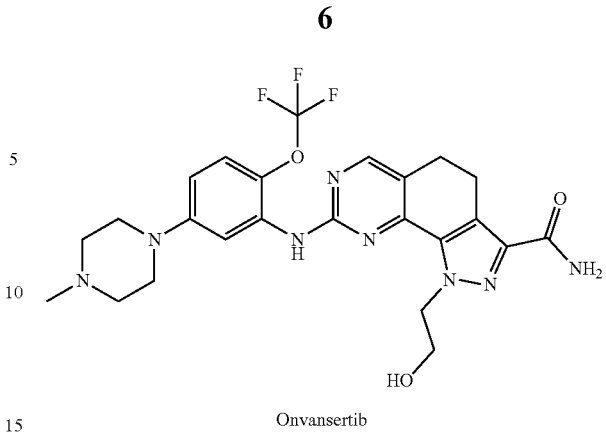

Onvansertib

Onvansertib shows high potency in proliferation assays having low nanomolar activity on a large number of cell lines, both from solid as well as hematologic tumors. Onvansertib potently causes a mitotic cell-cycle arrest followed by apoptosis in cancer cell lines and inhibits xenograft tumor growth with a clear PLK1-related mechanism of action at well tolerated doses in mice after oral administration. In addition, onvansertib shows activity in combination therapy with approved cytotoxic drugs, such as irinotecan, in which there is enhanced tumor regression in HT29 human colon adenocarcinoma xenografts compared to each agent alone, and shows prolonged survival of animals in a disseminated model of AML in combination therapy with cytarabine. Onvansertib has favorable pharmacologic parameters and good oral bioavailability in rodent and nonrodent species, as well as proven antitumor activity in different nonclinical models using a variety of dosing regimens, which may potentially provide a high degree of flexibility in dosing schedules, warranting investigation in clinical settings. Onvansertib has several advantages over volasertib (BI6727, another PLK1 inhibitor), including a higher degree of potency and specificity for the PLK1 isozyme, and oral bioavailability.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e., Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place. In some embodiments, the patient is a human or an animal. In some embodiments, the patient is a mammal.

As used herein, "administration" or "administering" refers to a method of giving a dosage of a pharmaceutically active ingredient to a vertebrate.

As used herein, a "dosage" refers to the combined amount of the active ingredients (e.g., onvansertib, an FGFR inhibitor (e.g., AZD4547, or a combination of onvansertib and AZD4547).

As used herein, a "unit dosage" refers to an amount of therapeutic agent administered to a patient in a single dose.

As used herein, the term "daily dose" or "daily dosage" refers to a total amount of a pharmaceutical composition or a therapeutic agent that is to be taken within 24 hours.

As used herein, the term "delivery" refers to approaches, formulations, technologies, and systems for transporting a pharmaceutical composition or a therapeutic agent into the body of a patient as needed to safely achieve its desired therapeutic effect. In some embodiments, an effective amount of the composition or agent is formulated for delivery into the blood stream of a patient.

As used herein, the term "formulated" or "formulation" refers to the process in which different chemical substances, including one or more pharmaceutically active ingredients, are combined to produce a dosage form. In some embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to a diseased tissue or a tissue adjacent to the diseased tissue. Carriers or excipients can be used to produce compositions. The carriers or excipients can be chosen to facilitate administration of a drug or pro-drug. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

As used herein, the term "pharmaceutically acceptable salt" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this disclosure are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

As used herein, the term "hydrate" refers to a complex formed by combination of water molecules with molecules or ions of the solute. As used herein, the term "solvate" refers to a complex formed by combination of solvent molecules with molecules or ions of the solute. The solvent can be an organic compound, an inorganic compound, or a mixture of both. Solvate is meant to include hydrate, hemihydrate, channel hydrate etc. Some examples of solvents include, but are not limited to, methanol, N,N-dimethylformamide, tetrahydrofuran, dimethylsulfoxide, and water.

As used herein, "therapeutically effective amount" or "pharmaceutically effective amount" refers to an amount of therapeutic agent, which has a therapeutic effect. The dosages of a pharmaceutically active ingredient which are useful in treatment when administered alone or in combination with one or more additional therapeutic agents are therapeutically effective amounts. Thus, as used herein, a therapeutically effective amount refers to an amount of therapeutic agent which produces the desired therapeutic effect as judged by clinical trial results and/or model animal studies. The therapeutically effective amount will vary depending on the compound, the disease, disorder or condition and its severity and the age, weight, etc., of the mammal to be treated. The dosage can be conveniently administered, e.g., in divided doses up to four times a day or in sustained-release form.

As used herein, the term "treat," "treatment," or "treating," refers to administering a therapeutic agent or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition. As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

As used herein, the term "prophylaxis," "prevent," "preventing," "prevention," and grammatical variations thereof as used herein refers the preventive treatment of a subclinical disease-state in a subject, e.g., a mammal (including a human), for reducing the probability of the occurrence of a clinical disease-state. The method can partially or completely delay or preclude the onset or recurrence of a disorder or condition and/or one or more of its attendant symptoms or barring a subject from acquiring or reacquiring a disorder or condition or reducing a subject's risk of acquiring or requiring a disorder or condition or one or more of its attendant symptoms. The subject is selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, each of the terms "partial response" and "partial remission" refers to the amelioration of a cancerous state, as measured by, for example, tumor size and/or cancer marker levels, in response to a treatment. In some embodiments, a "partial response" means that a tumor or tumor-indicating blood marker has decreased in size or level by about 50% in response to a treatment. The treatment can be any treatment directed against cancer, including but not limited to, chemotherapy, radiation therapy, hormone therapy, surgery, cell or bone marrow transplantation, and immunotherapy. The size of a tumor can be detected by clinical or by radiological means. Tumor-indicating markers can be detected by means well known to those of skill, e.g., ELISA or other antibody-based tests.

As used herein, each of the terms "complete response" or "complete remission" means that a cancerous state, as measured by, for example, tumor size and/or cancer marker levels, has disappeared following a treatment, including but are not limited to, chemotherapy, radiation therapy, hormone therapy, surgery, cell or bone marrow transplantation, and immunotherapy. The presence of a tumor can be detected by clinical or by radiological means. Tumor-indicating markers can be detected by means well known to those of skill, e.g., ELISA or other antibody-based tests. A "complete response" does not necessarily indicate that the cancer has been cured, however, as a complete response can be followed by a relapse.

Cancer

Methods, compositions and kits disclosed herein can be used for treating cancer. In some embodiments, a method for treating cancer comprises administrating an FGFR inhibitor (e.g., AZD4547), or a pharmaceutically acceptable salt, solvate, stereoisomer thereof, and a Polo-like kinase 1 (PLK1) inhibitor (e.g., onvansertib), or a pharmaceutically acceptable salt, solvate, stereoisomer thereof, to a subject (e.g., a patient) in need thereof.

The methods, compositions and kits disclosed herein can be used to various types of cancer, including but are not limited to, melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer (NSCLC) and small-cell lung cancer (SCLC)), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the disease or condition provided herein includes refractory or recurrent malignancies whose growth may be inhibited using the methods and compositions disclosed herein. In some embodiments, the cancer is carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, or a combination thereof. In some embodiments, the cancer is carcinoma, squamous carcinoma (e.g., cancer of cervical canal, eyelid, tunica conjunctiva, vagina, lung, oral cavity, skin, urinary bladder, tongue, larynx, and gullet), and adenocarcinoma (for example, cancer of prostate, small intestine, endometrium, cervical canal, large intestine, lung, pancreas, gullet, rectum, uterus, stomach, mammary gland, and ovary). In some embodiments, the cancer is sarcomata (e.g., myogenic sarcoma), leukosis, neuroma, melanoma, and lymphoma. In some embodiments, the cancer is bone cancer, breast cancer, brain tumor, central nervous system tumor, colorectal cancer, connective tissue cancer, endometrial cancer, esophageal cancer, gastric cancer, head and neck cancer, kidney cancer, leukemia, liver cancer, lung cancer, lymphoma, myeloma, ovarian cancer, pancreatic cancer, prostate cancer, skin cancer, soft tissue sarcoma, thyroid cancer, or bladder cancer.

The cancer can be a solid tumor, a liquid tumor, or a combination thereof. In some embodiments, the cancer is a solid tumor, including but are not limited to, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, Merkel cell carcinoma, brain and central nervous system cancers, and any combination thereof. In some embodiments, the cancer is a liquid tumor. In some embodiments, the cancer is a hematological cancer. Non-limiting examples of hematological cancer include Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), and multiple myeloma ("MM").

The cancer can be FGFR altered cancer which comprises one or more FGFR alterations and/or FGFR aberrant activation such as copy number alteration (CNA), single-nucleotide variation (SNV), and gene rearrangement or fusions. The FGFR alterations can be in one or more of the FGFR genes including FGFR1, FGFR2, FGFR3, and FGFR4. Non-limiting exemplary cancer with FGFR alterations include head and neck cancer (e.g., head and neck squamous cell carcinoma), lung cancer (e.g., non-small cell lung cancer and small-cell lung cancer), intrahepatic cholangiocarcinoma (iCCA), gastric cancer, urothelial cancer, endometrial cancer, cervical cancer, rhabdomyosarcoma, cholangiocarcinoma, glioblastoma, low-grade glioma, ovarian cancer, prostate adenocarcinoma, thyroid carcinoma, endometrial cancer, and gallbladder cancer.

In some embodiments, the cancer can comprise FGFR gene fusion, which can occur, for example, through chromosomal rearrangements or translocations. The cancer with FGFR gene fusion include, but are not limited to, breast cancer, urothelial carcinoma, glioblastoma, head and neck squamous cell carcinoma, intrahepatic cholangiocarcinoma (iCCA), low-grade glioma, lung adenocarcinoma, lung squamous cell carcinoma, ovarian cancer, prostate adenocarcinoma and thyroid carcinoma.

In some embodiments, the cancer can be FGFR-amplified cancer in which one or more FGFR gene (e.g., FGFR1, FGFR2, FGFR3, and FGFR4) is amplified, for example, as a result of gene duplication or aberrant gene transcriptional control. For example, the cancer with FGFR amplification can be breast cancer with FGFR (e.g., FGFR1) amplification including, for example, hormone-receptor positive (HR+) breast cancer, human epidermal growth factor receptor 2-positive (HER2+) breast cancer, and triple negative breast cancer, lung cancer with FGFR (e.g., FGFR1) amplification including, for example, squamous lung cancer and small-cell lung cancer, and urothelial cancer with FGFR (e.g., FGFR1) amplification.

In some embodiments, the cancer can comprise one or more SNVs in one or more of the FGFR genes (e.g., FGFR1, FGFR2, FGFR3, and FGFR4). For example, the cancer with one or more SNVs in FGFR genes include, but are not limited to, breast cancer, gallbladder cancer, endometrial cancer, non-small cell lung cancer, gastric cancer, urothelial carcinoma and rhabdomyosarcoma.

FIG. 1 is a non-limiting schematic illustration showing cancer types that harbor alterations in FGFR. This figure is reproduced from Krook et al., *Br. J. Cancer,* 2021, 124, 880, the content of which is incorporated herein by reference in its entirety.

In some embodiments, the cancer is a lung cancer. The lung cancer can be, for example, non-small cell lung cancer (NSCLC) and small-cell lung cancer (SCLC, also known as oat cell lung cancer). NSCLC can comprise subcategories such as adenocarcinoma, squamous cell carcinoma (SqCC), large cell carcinoma, and other cancer types including adenosquamous carcinoma and sarcomatoid carcinoma. In some embodiments, the lung cancer is NSCLC, SqCC, NSCLC adenocarcinoma, NSCLC large cell carcinoma, and/or SCLC. The lung cancer can be, in some embodiments, pulmonary metastases or pulmonary neuroendocrine tumor (including but not limited to large cell neuroendocrine carcinoma, typical carcinoid tumor, and atypical carcinoid tumor).

In some embodiments, the lung cancer can be FGFR-altered lung cancer which comprises one or more FGFR genomic alterations such as FGFR gene amplification, mutations (e.g., somatic mutations), and translocations. The FGFR genomic alterations can be in one or more of the FGFR genes including FGFR1, FGFR2, FGFR3, and FGFR4. In some embodiments, the lung cancer can be FGFR-amplified lung cancer (e.g., FGFR1-amplified lung cancer) in which FGFR gene is amplified. In some embodiments, the lung cancer comprises one or more point mutations in FGFR1-4 (e.g., FGFR2 and FGFR3). Details of FGFR alterations in lung cancer are described in, for example, Pacini et al., Cells, 2021, 10, 1154, the content of which is incorporated herein by reference in its entirety.

FGFR Inhibitors and PLK Inhibitors

Methods, compositions and kits disclosed herein can be used for treating cancer, for example lung cancer, cervical cancer, urothelial cancer, gastric cancer intrahepatic cholangiocarcinoma, endometrial cancer, rhabdomyosarcoma, cholangiocarcinoma, ovarian cancer, breast cancer, prostate cancer, colorectal cancer, pancreatic cancer, or a combination thereof. In some embodiments, a method for treating cancer comprises administrating an FGFR inhibitor (e.g., AZD4547), or a pharmaceutically acceptable salt, solvate, stereoisomer thereof, and a Polo-like kinase 1 (PLK1) inhibitor (e.g., onvansertib), or a pharmaceutically acceptable salt, solvate, stereoisomer thereof, to a subject (e.g., a patient) in need thereof. The method can comprise administering a pharmaceutically effective amount of the FGFR inhibitor (e.g., AZD4547) and a pharmaceutically effective amount of the PLK1 inhibitor (e.g., onvansertib).

The fibroblast growth factor receptor (FGFR) family plays a central role in a broad range of important physiological events during embryonic development and adult response to injury, tissue repair and regeneration. FGFRs are key to the regulation of a number of cellular processes such as survival, proliferation, migration, differentiation and metabolism. They are also involved in the development and progression of several cancer types (e.g., lung cancer). The FGFR family is composed of four highly conserved receptor tyrosine kinases, FGFR1, FGFR2, FGFR3 and FRFR4. From the N- to the C-terminus, the FGFR members each contain a large extracellular ligand-binding domain that comprises three immunoglobulin (Ig)-like subunits (D1, D2 and D3) followed by a single transmembrane helix and an intracellular tyrosine kinase domain. The linker region between D1 and D2 contains a highly conserved motif that is rich in aspartate acids. D2 and D3 subunits of the extracellular ligand-binding domain are the fibroblast growth factor binding region. The intracellular tyrosine kinase domain of FGFR exhibits the canonical bilobed architecture of protein kinase. The fold of the N-terminal small lobe (N-lobe, ~100 amino acid residues) consists of a five-stranded antiparallel β-sheet (β1-β5) and the αC-helix. The C-terminal large lobe (C-lobe, ~200 amino acid residues) predominately comprises seven a helices. The active site, which is responsible for ATP and substrate protein binding, is located in a clef between the two lobes. The active site comprises several loops including an activation loop, which is essential for kinase activation. The conformation of the highly conserved Asp-Phe-Gly motif (DFG-motif) in the activation loop is an indicator of kinase activity status. Generally, the DFG-motif exists in two states: the active DFG-in and inactive DFG-out conformations. In the DFG-in state, the aspartate residue of the DFG-motif plays a key role in ATP binding through the coordination of all three phosphate groups of ATP, while these interactions are sterically impossible when the motif is in the DFG-out conformation.

FGFR1-4 can be activated by the binding of a variety of fibroblast growth factor (FGF) ligands. There are 22 FGF ligands in mammals that range in size from 150-300 amino acids. Crystallography studies have shown that there is a homologous core domain in all FGFs composed of around 125 amino acids. The region outside the conserved core is comprised of variable amino acid sequences that determine the selectivity of binding of distinct FGFs to different FGFR family members. FGFs bind to FGFR, resulting in receptor dimerization which drives the transphosphorylation of the intracellular tyrosine kinase domain including the recruitment of adaptor proteins responsible for the activation of several downstream signaling pathways through which these receptors exert their biological functions. Examples of the most common signaling pathways activated by FGFRs are the rat sarcoma kinase (RAS) and mitogen-activated protein kinase (MAPK), the phosphatidylinositol 3-kinase/protein kinase B (PI3K/AKT), signal transduction and activation of transcription (STAT), the c-Jun N-terminal kinase (JNK) and SRC pathways. These pathways play multiple roles in cell survival, growth, migration, differentiation and metabolism.

Figure 2:
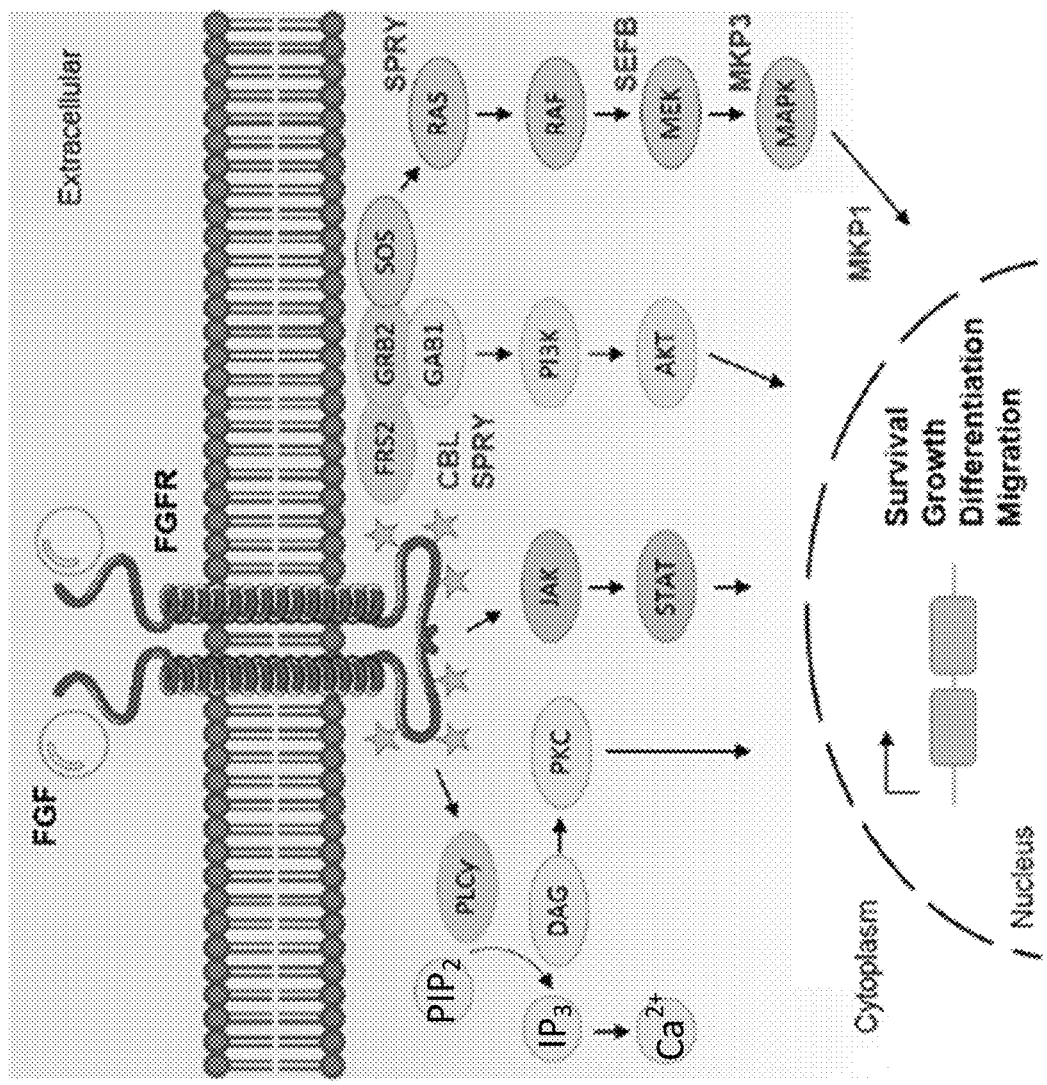
FIG. 2 depicts a non-limiting schematic illustration showing FGFR canonical signaling pathways. This figure is reproduced from Pacini et al., *Cells* 2021, 10, 1154.

FIG. 2 is a non-limiting schematic illustration showing FGFR canonical signaling pathways. FGFs bind to FGFR inducing receptor dimerization which then drives the transphosphorylation of the tyrosine kinase domain in the intracellular compartment of the cell. The intracellular portion of active FGFR is phosphorylated at multiple tyrosine sites (denoted as the yellow stars), leading to activation of downstream signaling pathways. This figure is reproduced from Pacini et al., *Cells* 2021, 10, 1154, the content of which is incorporated herein by reference in its entirety.

FGFR-altered cancer can comprise one or more aberrations in one or more of the FGFR1-4. Aberrations in FGFR have been implicated in the initiation and progression of several cancer types. Reported FGFR alterations in cancer include receptor translocations, amplifications and point mutations (single-nucleotide variations). In addition to these mechanisms, a switch in FGFR splicing isoform, alterations in FGFR internalization, impaired signaling termination and defective FGF ligand secretion have also been reported to affect FGFR canonical pathways leading to oncogenesis. It has been reported that FGFRs are aberrantly activated in about 5-10% of all human cancers, and 10-30% in urothelial carcinoma, intrahepatic cholangiocarcinoma, lung cancer and certain breast cancer. It has also been reported that of the FGFR altered cancers, 66% of aberrations are due to CNVs, 26% are SNVs, and 8% are gene rearrangements or fusions.

FGFR SNVs can cause the receptor to be constitutively active by conferring increased dimerization, increased kinase activity or enhanced affinity for FGF ligands. SNVs in FGFR can be in the extracellular domain, the transmembrane domain and the intracellular kinase domain of FGFR. For example, mutations identified in SqCC lung cancer patients include extracellular domain mutations such as mutations W290C and S320C and the kinase domain mutations such as mutations K660E and K660N in FGFR2. Mutations identified in FGFR3 include mutations in the kinase domain including, for example, R248C and S249C.

FGFR gene fusions can occur through chromosomal rearrangements or translocations, leading to increased receptor dimerization and activation, as well as the dysregulated expression of FGFR or its fusion partner gene. Fusions of FGFR (e.g., FGFR1-3) involving many different partner genes have been detected in a variety of cancers. The fusion can occur between a partner gene and either FGFR N-terminus or C-terminus.

FGFR amplification has been reported to be the most common alteration in the FGFR family. FGFR amplification has been shown to occur as a results of gene duplication or aberrant gene transcriptional control. Amplification of the FGFR gene can lead to receptor overexpression at the cell membrane, which results in ligand-independent dimerization by stochastic diffusion through the membrane. Studies have shown that amplifications are relatively common in breast cancer (23% of HR+, 27% of HER2+ and 7% of TNBC), squamous lung cancer (17%), SCLC (6%) and urothelial cancer (7%).

The methods and compositions for treating cancer in combination with one or more PLK1 inhibitors disclosed herein can include one or more FGFR inhibitors. FGFR inhibitors used herein are molecules capable of inhibiting FGFR phosphorylation and signaling, thus decreasing cell viability in cancer cells expressing FGFR genetic alterations, while exhibiting little or no toxicity. FGFR inhibitors include small-molecule tyrosine kinase inhibitors (TKIs), which can be non-selective, selective and covalent, monoclonal antibodies, FGF ligand traps and DNA/RNA aptamers. In some embodiments, the FGFR inhibitors used herein can bind to the adenosine triphosphate (ATP) pocket of aberrant FGFRs while exhibiting little or no toxicity to an individual.

The FGFR inhibitors can comprise non-selective TKIs. Non-selective TKIs are multitargeted kinase inhibitors, including for example ponatinib, dovitinib and nintedanib, which, although not designed to target FGFR specifically, are able to reversibly and competitively bind to, and therefore disrupt, the ATP-binding pocket in FGFR1-4.

The FGFR inhibitors can comprise selective TKIs. Selective TKIs are FGFR specific TKIs that selectively and/or specifically target FGFR1, FGFR2, FGFR3 and/or FGFR4, also referred to as "pan-FGFR inhibitors". Selective TKIs include, for example, AZD4547, erdafitinib (JNJ-42756493), Debio1347, infigratinib (BGJ398), LY2874455, E7090, pemigatinib (INCB054828), CPL-304-110 and rogaratinib (BAY1163877). The pan-FGFR inhibitors can be reversible or irreversible based on the interaction between the inhibitor and FGFR. The interaction can be covalent (irreversible) or noncovalent (reversible). Examples of reversible pan-FGFR inhibitors include FGF401, Rogaratinib, pemigatinib (INCB054828), infigratinib (BGJ398), CH5183284, LY2874455, AZD4547, and Erdafitinib. The irreversible pan-FGFR inhibitors can form a covalent bond and cannot be readily displaced by ATP, resulting in prolonged inhibition. Irreversible pan-FGFR inhibitor include, for example, Futibatinib (TAS-120), fisogatinib (BLU-554), roblitinib (FGF401), INCB062079, PRN1371, and H3B-6527.

The FGFR inhibitors can be monoclonal antibodies that can inhibit FGFR through a number of mechanisms, including disruption of ligand binding and/or receptor dimerization, or conjugation of the antibody of interest to a cytotoxic agent (ADCs). Exemplary monoclonal antibody FGFR inhibitor include, for example, Bemarituzumab (FPA144), MFGR1877S, LY3076226, and Vofatamab (B-701).

The FGFR inhibitors can also be an FGF ligand trap, which inhibits FGF/FGFR signaling in cancer by disrupting the binding of FGF ligands to their cognate receptors. For example, an FGF ligand trap can be a decoy receptor that lacks the transmembrane and cytoplasmic domains but maintains the extracellular FGFR domain, which allows for the interaction with, and consequent sequestration of, FGF ligands. Exemplary FGF ligand traps include, for example, FP-1039/GSK3052230.

Figure 3:
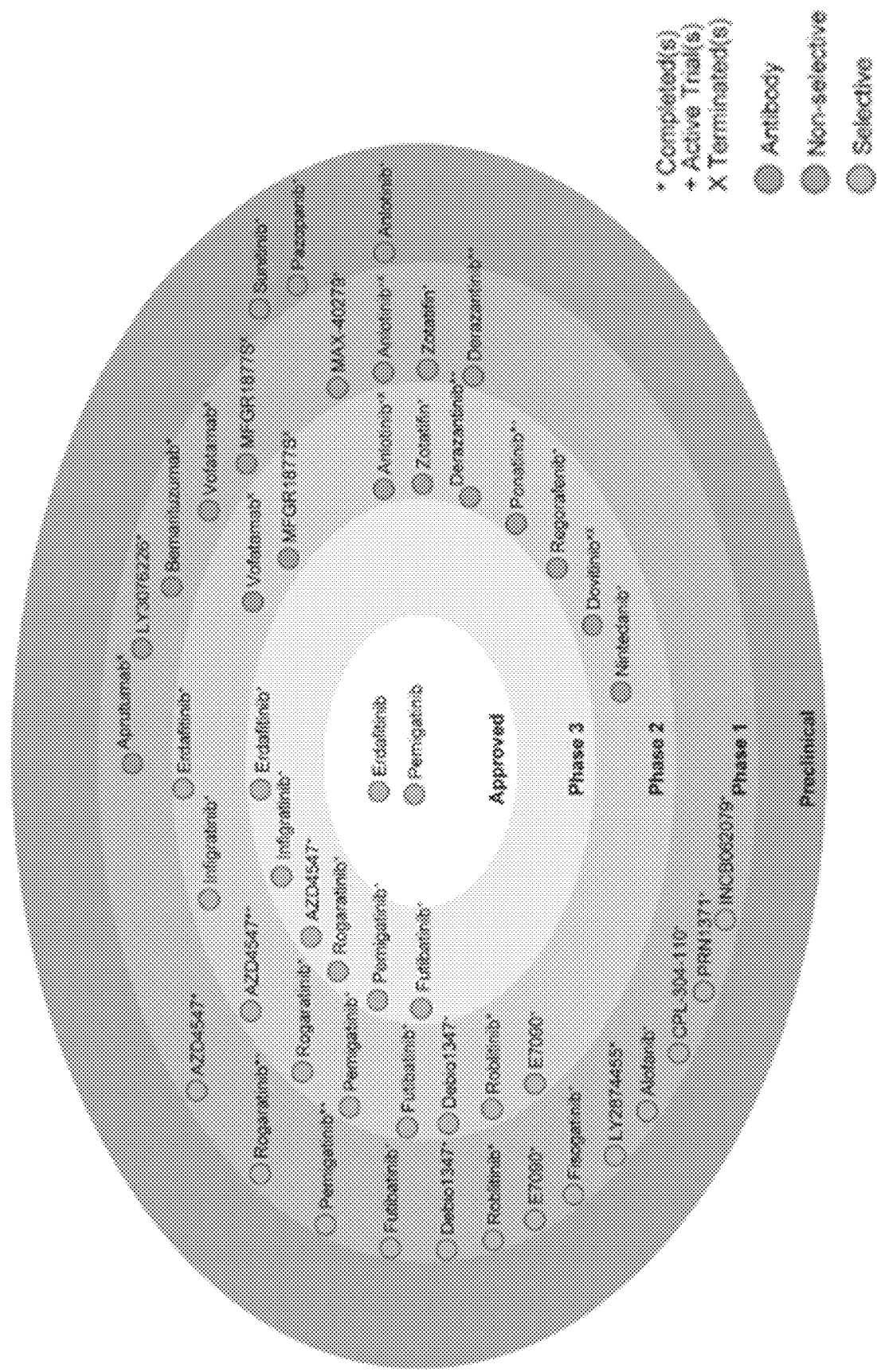
FIG. 3 depicts a non-limiting schematic illustration showing current clinical landscape FGFR inhibitors. This figure is reproduced from Krook et al., *Br. J. Cancer,* 2021, 124, 880.

FIG. 3 is a non-limiting schematic illustration showing current clinical landscape of FGFR inhibitors. This figure is reproduced from Krook et al., *Br. J. Cancer,* 2021, 124, 880. Numerous FGFR inhibitors are currently being assessed in preclinical, Phase 1, Phase 2 and Phase 3 clinical trials.

In some embodiments, the FGFR inhibitor can be Sunitibib, Pazopanib, Anlotinib, MAX-40279, Zotatifin, Derazantinib, Aprutumab, LY3076226, Bemarituzumab, Vofatamab, MFGR1877S, AZD4547, Rogaratinib, Pemigatinib, Futibatinib, Debio 1347, Roblitinib, E7090, Fisogatinib, LY2874455, Alofanib, CPL-304-110, PRN1371, INCB062079, Ponatinib, Regorafenib, Dovitinib, Nintedanib, Erdafitinib, CH5183284, Infigratinib (BGJ398), Rogaratinib, Futibatinib (TAS-120), fisogatinib (BLU-554), roblitinib (FGF401), H3B-6527, E7090, HMPL-453, Anlotinib, TKI258, Lucitanib, RLY-4008, EVER4010001, or a combination thereof.

Some FGFR inhibitors have been approved by FDA for treating cancers. For example, Erdafitinib has been approved for treating FGFR3-alterated urothelial carcinoma and Pemigatinib has been approved for treating cholangiocarcinoma with FGFR2 alterations.

In some embodiments, the FGFR inhibitor can be AZD4547, LY2874455, CH5183284, FGF401, Infigratinib, Erdafitinib, Rogaratinib, Pemigatinib, Futibatinib, fisogatinib, roblitinib, INCB062079, PRN1371, H3B-6527 or a combination thereof.

In some embodiments, the FGFR inhibitors herein described are small-molecule TKIs, particularly pan-FGFR inhibitors. In some embodiments, the FGFR inhibitors herein described are reversible pan-FGFR inhibitors. In some embodiments, the FGFR inhibitor is an FGFR1, FGFR2, FGFR3, and/or FGFR4 inhibitor. In some embodiments, the FGFR inhibitor can bind FGFRs in an ATP-competitive manner with the highly conserved DFG-motif in an active conformation. In some embodiments, the FGFR inhibitor can be AZD4547, LY2874455, CH5183284, FGF401, Infigratinib, Erdafitinib, Rogaratinib, Pemigatinib, Futibatinib, fisogatinib, roblitinib, INCB062079, PRN1371, H3B-6527 or a combination thereof.

Figure 4:
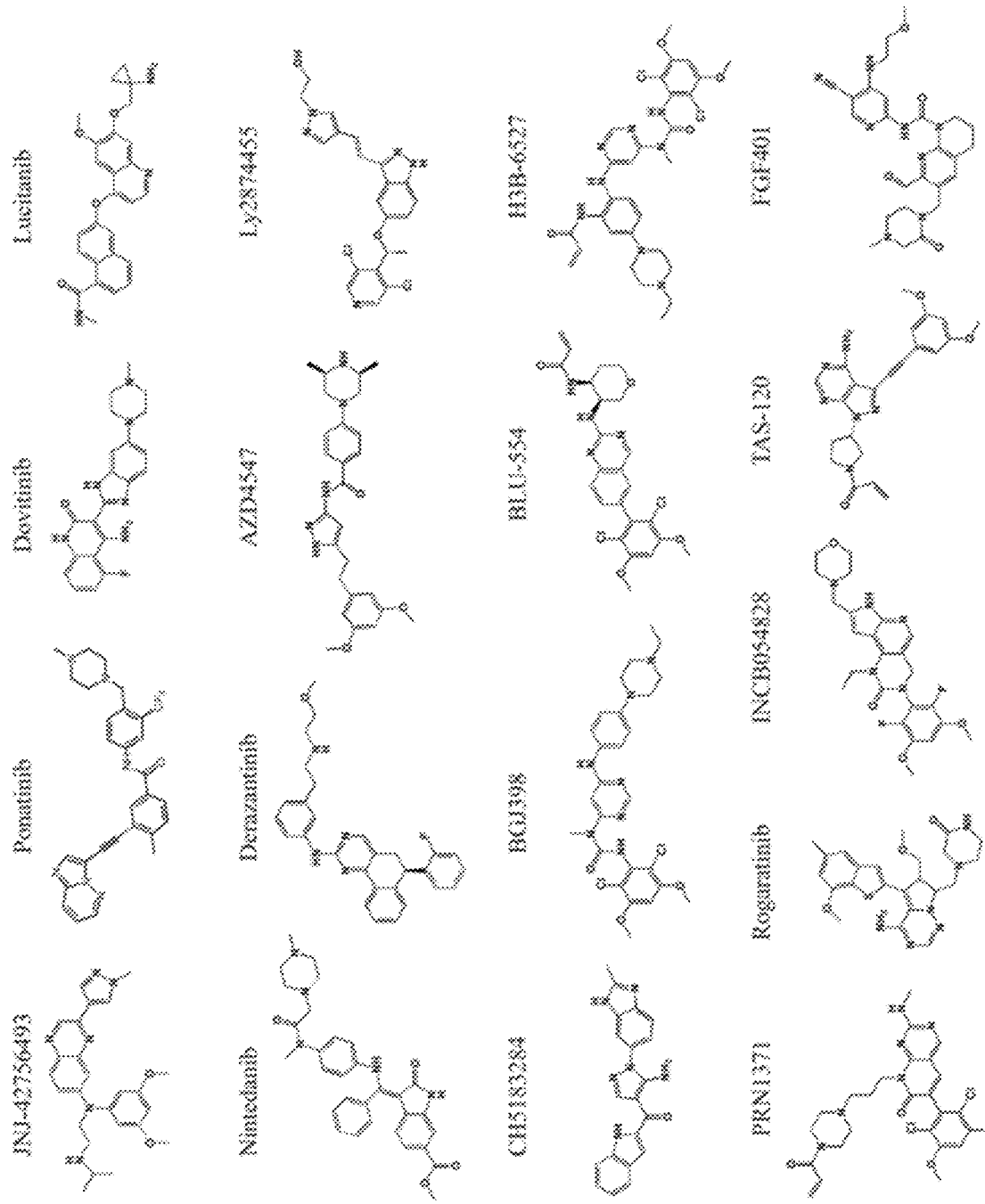
FIG. 4 shows chemical structures of non-limiting examples of FGFR small molecule inhibitors. This figure is reproduced from Dai et al., Cells. 2019, 8(6):614.

FIG. 4 shows chemical structures of non-limiting FGFR small molecule inhibitors. This figure is reproduced from Dai et al., Cells. 2019, 8(6):614, the content of which is incorporated herein by reference in its entirety.

In some embodiments, the FGFR inhibitor is AZD4547. AZD4547 is a small-molecule selective FGFR inhibitor that selectively inhibits FGFRs and suppresses FGFR signaling.

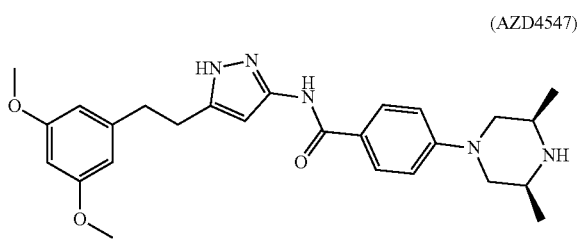

(AZD4547)

AZD4547 (N-[5-[2-(3,5-Dimethoxyphenyl)ethyl]-2H-pyrazol-3-yl]-4-(3,5-diemthylpiperazin-1-yl)benzamide AZD4547 has been shown to be a potent inhibitor of FGFR1, 2, and 3 and is also selective versus a range of other related kinases, such as KDR, IGF, PI3Ka, and AKT. Biochemical assays demonstrated that AZD4547 can potently inhibit FGFR phosphorylation and downstream signaling in human tumor cell lines and that AZD4547 has potent in vitro antiproliferative effects on tumor cell lines with deregulated FGFR expression (see e.g., Gavine et al., Cancer, Res; 72(8); 2045-56). In a representative FGFR-driven human tumor xenograft model, oral administration of AZD4547 was well tolerated and resulted in potent dose-dependent antitumor activity, consistent with plasma exposure and pharmacodynamic modulation of tumor FGFR. It has been reported that AZD4547 potently inhibits autophosphorylation of FGFR1, 2, and 3 tyrosine kinases ($IC_{50}$ values of 12, 2, and 40 nmol/L, respectively) and displays weaker inhibition of FGFR4 cellular kinase activity ($IC_{50}$=142 nmol/L). Significantly weaker inhibitory activity was observed versus cellular KDR and IGFR ligand-induced phosphorylation ($IC_{50}$ values of 258 and 828 nmol/L, respectively), representing approximately 20- and 70-fold selectivity over cellular FGFR1. At efficacious doses, no evidence of anti-KDR—related effects were observed, confirming the in vivo FGFR selectivity of AZD4547. AZD4547 has been shown to be a selective small-molecule inhibitor of FGFR with potent antitumor activity against FGFR-deregulated tumors in pre-clinical models. AZD4547 is disclosed in and can be synthesized according to the processes described in the International Patent Application Publication WO2008/075068 (the content of which is incorporated hereby in its entirety), in particular as described in Example 80.

In some embodiments, the FGFR inhibitor is Infigratinib. Infigratinib is a potent inhibitor of the FGFR family with $IC_{50}$s of 0.9 nM, 1.4 nM, 1 nM, and 60 nM for FGFR1, FGFR2, FGFR3, and FGFR4, respectively. By inhibiting the FGFR pathway, Infigratinib suppresses tumour growth.

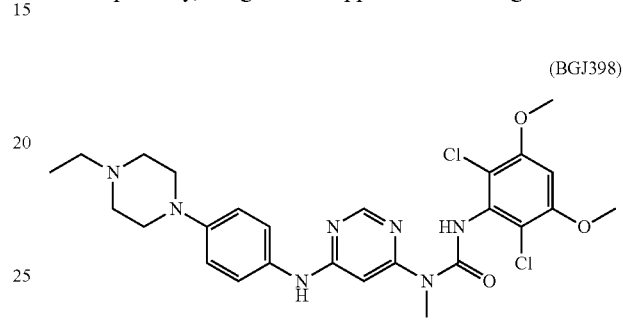

(BGJ398)

Infigratinib (3-(2,6-dichloro-3,5-dimethoxyphenyl)-1-[6-[4-(4-ethylpiperazin-1-yl)anilino]pyrimidin-4-yl]-1-methyluera)

In some embodiments, the FGFR inhibitor is Erdafitinib. Erdafitinib is a potent and orally available FGFR family inhibitor, inhibiting FGFR1/2/3/4 with $IC_{50}$s of 1.2, 2.5, 3.0 and 5.7 nM, respectively. By inhibiting the FGFR pathway, Erdafitinib is used in the therapy of locally advanced, unresectable or metastatic urothelial carcinoma.

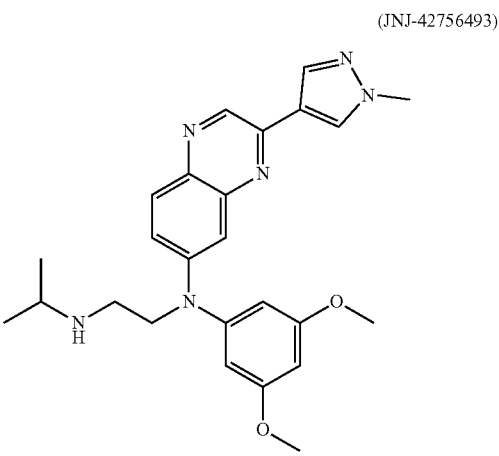

(JNJ-42756493)

Erdafitinib (N'-(3,5-dimethoxyphenyl)-N'-[3-(1-methylpyrazol-4-yl)quinoxalin-6-yl]-N-propan-2-ylethane-1,2-diamine)

Polo-like kinases (PLK) are a family of five highly conserved serine/threonine protein kinases. PLK1 is a master regulator of mitosis and is involved in several steps of the cell cycle, including mitosis entry, centrosome maturation, bipolar spindle formation, chromosome separation, and cytokinesis. PLK1 has been shown to be overexpressed in solid tumors and hematologic malignancies, including AML. PLK1 inhibition induces G2-M-phase arrest with subsequent apoptosis in cancer cells, and has emerged as a promising targeted therapy. Several PLK inhibitors have been studied in clinical trials. In a randomized phase II study of patients with AML who were treatment naïve yet unsuitable for induction therapy, the pan-PLK inhibitor, volasertib (BI6727), administered intravenously in combination with LDAC showed a significant increase in OS when compared with LDAC alone. A subsequent randomized phase III study identified no benefit of the combination and described an increased risk of severe infections. PLK1 facilitates HR during Double Strand DNA Break (DSB) Repair. PLK1 phosphorylates Rad51 and BRCA1, facilitating their recruitment to DSB sites and thereby HR-mediated DNA repair.

Onvansertib (also known as PCM-075 or NMS-1286937) is a selective ATP-competitive PLK1 inhibitor. Biochemical assays demonstrated high specificity of onvansertib for PLK1 among a panel of 296 kinases, including other PLK members. Onvansertib has potent in vitro and in vivo antitumor activity in models of both solid and hematologic malignancies. Onvansertib inhibited cell proliferation at nanomolar concentrations in AML cell lines and tumor growth in xenograft models of AML. In addition, onvansertib significantly increased cytarabine antitumor activity in disseminated models of AML.

A phase I, first-in-human, dose-escalation study of onvansertib in patients with advanced/metastatic solid tumors identified neutropenia and thrombocytopenia as the primary dose-limiting toxicities. These hematologic toxicities were anticipated on the basis of the mechanism of action of the drug and were reversible, with recovery occurring within 3 weeks. The half-life of onvansertib was established between 20 and 30 hours. The oral bioavailability of onvansertib plus its short half-life provide the opportunity for convenient, controlled, and flexible dosing schedules with the potential to minimize toxicities and improve the therapeutic window. Pharmacodynamics and biomarker studies, including baseline genomic profiling, serial monitoring of mutant allele fractions in plasma, and the extent of PLK1 inhibition in circulating blasts, have been performed to identify biomarkers associated with clinical response and are described in PCT Application No. PCT/US2021/013287, the content of which is incorporated herein by reference in its entirety.

Figure 5:
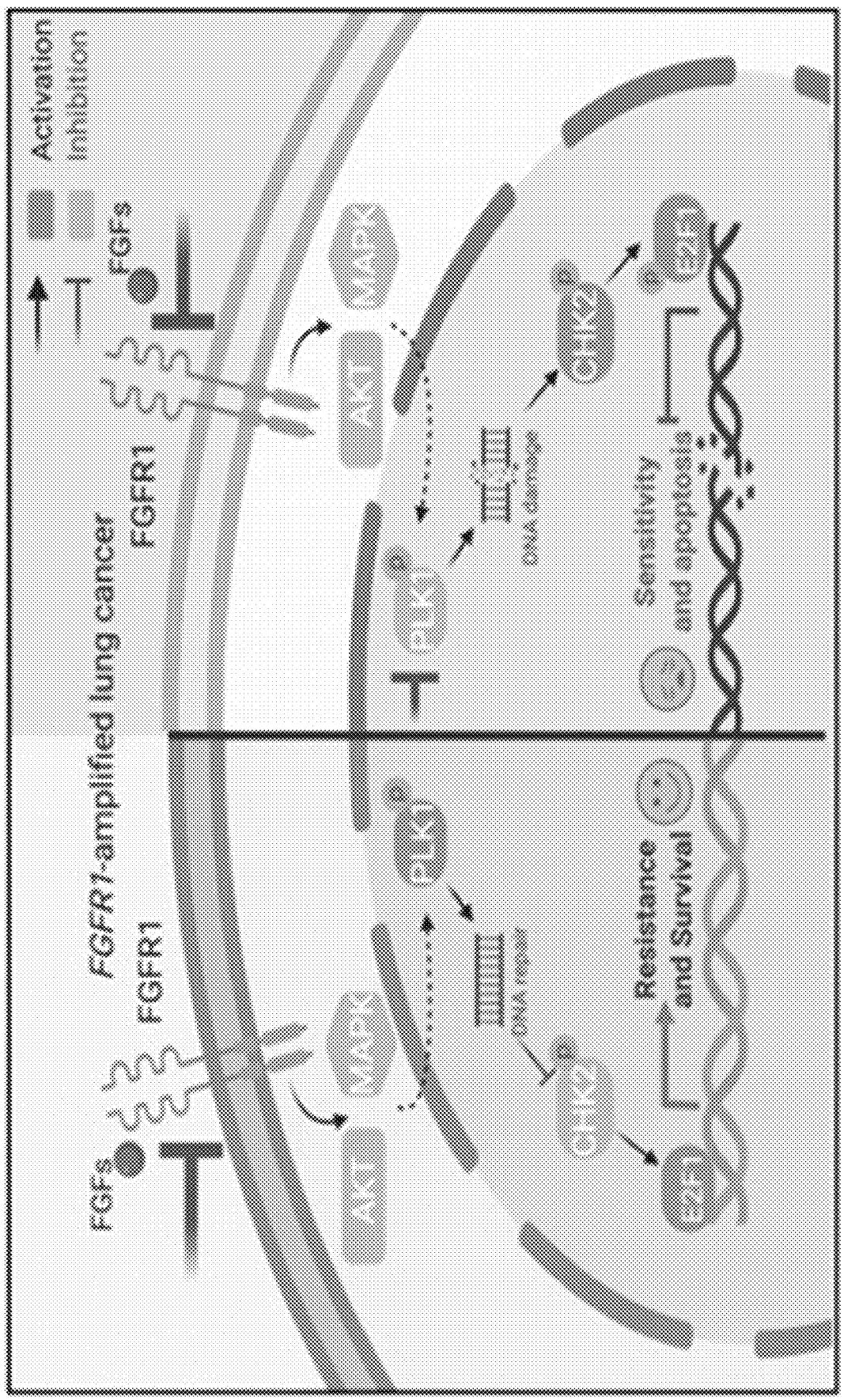
FIG. 5 depicts a non-limiting schematic illustration showing PLK1 promoters acquired resistance to FGFR-targeted therapy. This figure is reproduced from Yang et al., Cancer Res., 2021, (81) (11) 3121.

Yang et al. (Cancer Res., 2021, (81) (11) 3121) shows that PLK1 inhibitor BI2536 in combination with FGFR inhibitors synergistically enhances antiproliferative effects and apoptosis in FGFR1-amplified lung cancer cells. FIG. 5 is a non-limiting schematic illustration showing PLK1 promoters acquired resistance to FGFR-targeted therapy. This figure is reproduced from Yang et al., the content of which is incorporated herein by reference in its entirety. The study shows that PLK1 activation promotes DNA damage repair and restrains CHK2 and E2F1 phosphorylation, which compensates for FGFR inhibition-induced cell-cycle arrest (left panel in FIG. 5). However, combined FGFR1/PLK1 inhibition using PLK1 inhibitor BI2536 and FGFR1 inhibitor AZD4547 induces DNA damage, leading to the induction of CHK2 and E2F1 phosphorylation and in turn apoptosis (right panel in FIG. 5).

As disclosed herein, a combinational therapy using an FGFR inhibitor and a PLK1 inhibitor (including onvansertib) can result in significantly enhanced efficacy against cancer (e.g., head and neck cancer, non-small cell lung cancer, intrahepatic cholangiocarcinoma, gastric cancer, urothelial cancer, small cell lung cancer, breast cancer, endometrial cancer, cervical cancer, rhabdomyosarcoma, cholangiocarcinoma, ovarian cancer, or a combination thereof), causing tumor regression and cancer survival. Surprisingly, the resulting tumor regression and cancer survival rate/duration by the combination is more than additive, i.e., superior to the cumulated anti-tumor efficacy caused by the FGFR inhibitor and the PLK1 inhibitor separately. The PLK1 inhibitor can be onvansertib. Provided herein include methods, compositions and kits for treating cancer in a subject (for example, a human patient suffering from cancer). The method comprises administrating an FGFR inhibitor and a PLK1 inhibitor to the patient in a manner sufficient to inhibit progression of the cancer. For example, the FGFR inhibitor and the PLK1 inhibitor can be administrated to a subject with cancer simultaneously, separately, or sequentially. As disclosed herein, the combination treatment using onvansertib and FGFR inhibitor (e.g., FGFR1 inhibitor AZD4547) is significantly more effective than the combination treatment using BI2536 and FGFR1 for various cancer treatments, including the treatment for lung cancer (e.g., SqLC). It is also expected that the combination treatment using onvansertib and FGFR inhibitor (e.g., FGFR1 inhibitor AZD4547) has better safety and toxicity profile than the combination treatment using BI2536 and FGFR1.

In some embodiments, the inhibition of cancer progression is not merely additive, but is enhanced or synergistic (that is, the inhibition is greater than the combined inhibition of progression caused by the FGFR inhibitor alone plus the PLK1 inhibitor alone). The enhanced or synergistic efficacy or inhibition of any combination of an FGFR inhibitor and a PLK1 inhibitor of the present disclosure can be different in different embodiments. In some embodiments, the enhanced or synergistic efficacy or inhibition of any combination of an FGFR inhibitor and a PLK1 inhibitor of the present disclosure is, is about, is at least, is at least about, is at most, or is at most about, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values, higher than the combined inhibition of progression caused by the FGFR inhibitor alone plus the PLK1 inhibitor alone.

The method disclosed herein is expected to be effective with various cancers, for example, head and neck cancer, non-small cell lung cancer, intrahepatic cholangiocarcinoma, gastric cancer, urothelial cancer, small cell lung cancer, breast cancer, endometrial cancer, cervical cancer, rhabdomyosarcoma, cholangiocarcinoma, liver cancer, ovarian cancer, prostate cancer, colorectal cancer, pancreatic cancer, or a combination thereof.

As described herein, the patient can achieve complete response or partial response after treatment with the FGFR inhibitor and the PLK1 inhibitor. In some embodiments, the patient achieves a complete response. In some embodiments, the patient achieves a partial response. In some embodiments, the patient did not respond to treatment with only FGFR inhibitor(s). In some embodiments, the patient did not respond to treatment with the FGFR inhibitor alone.

The FGFR inhibitor and the PLK1 inhibitor can be administered to the patient in any manner deemed effective to treat the cancer. The FGFR inhibitor can be administered together with, or separately from, the PLK1 inhibitor. When administered separately, the FGFR inhibitor can be administered before or after the PLK1 inhibitor, or in different administration cycles.

The FGFR inhibitor and the PLK1 inhibitor can each be administered in any schedule, e.g., once or multiple times per day or week; once, twice, three times, four times, five times, six times or seven times (daily) per week; for one or multiple weeks; etc. In some embodiments, the FGFR inhibitor and the PLK1 inhibitor are each administered to the patient in a cycle of at least twice within a week. In other embodiments, the FGFR inhibitor and the PLK1 inhibitor are each administered to the patient in a cycle of at least five times within a week. In further embodiments, the patient undergoes at least two cycles of administration.

Any FGFR inhibitor, now known or later discovered, can be used in these methods, including FGFR inhibitors that are selective for FGFR (e.g., FGFR1, FGFR2, FGFR3, and/or FGFR4), and FGFR inhibitors that also inhibit the activity of other kinase proteins. The FGFR inhibitors can be small-molecule TKIs, particularly pan-FGFR inhibitors. Nonlimiting examples of FGFR inhibitors include Sunitibib, Pazopanib, Anlotinib, MAX-40279, Zotatifin, Derazantinib, Aprutumab, LY3076226, Bemarituzumab, Vofatamab, MFGR1877S, AZD4547, Rogaratinib, Pemigatinib, Futibatinib, Debio 1347, Roblitinib, E7090, Fisogatinib, LY2874455, Alofanib, CPL-304-110, PRN1371, INCB062079, Ponatinib, Regorafenib, Dovitinib, Nintedanib, Erdafitinib, CH5183284, infigratinib (BGJ398), Rogaratinib, Futibatinib (TAS-120), fisogatinib (BLU-554), roblitinib (FGF401), H3B-6527, E7090, HMPL-453, Anlotinib, TKI258, Lucitanib, RLY-4008, and EVER4010001. In some embodiments, the FGFR inhibitor can bind FGFRs in an ATP-competitive manner with the highly conserved DFG-motif in an active conformation. In some embodiments, the FGFR inhibitor is AZD4547, LY2874455, CH5183284, FGF401, Infigratinib, Erdafitinib, Rogaratinib, Pemigatinib, Futibatinib, fisogatinib, roblitinib, INCB062079, PRN1371, H3B-6527 or a combination thereof. In some embodiments, the FGFR inhibitor is AZD4547.

The FGFR inhibitor (e.g., AZD4547) can be administered to the patient at any appropriate dosage, e.g., a dosage of about, at least or at most 2 mg/kg, 5 mg/kg, 10 mg/kg, 20 mg/kg, or a number between any two of these values. The dosage unit based on the body weight (mg/kg) can be converted to another unit (e.g., mg/m$^2$) using a conversion chart such as the body surface area (BSA) conversion chart as will be understood by a person skilled in the art. The FGFR inhibitor can be administered to the patient once daily or twice daily. In some embodiments, the FGFR inhibitor is administered in a cycle of 3-10 days of daily administration.

Similarly, any PLK1 inhibitor, now known or later discovered, can be used in these methods, including PLK1 inhibitors that are selective for PLK1, and PLK1 inhibitors that also inhibit the activity of other proteins. In some embodiments, the PLK1 inhibitor is a dihydropteridinone, a pyridopyrimidine, a aminopyrimidine, a substituted thiazolidinone, a pteridine derivative, a dihydroimidazo[1,5-f] pteridine, a metasubstituted thiazolidinone, a benzyl styryl sulfone analogue, a stilbene derivative, or a combination thereof. In some of these embodiments, the PLK1 inhibitor is onvansertib, BI2536, Volasertib (BI 6727), GSK461364, AZD1775, CYC140, HMN-176, HMN-214, rigosertib (ON-01910), MLN0905, TKM-080301, TAK-960 or Ro3280.

In some embodiments, the PLK1 inhibitor is onvansertib. In these embodiments, the onvansertib is administered to the patient at any appropriate dosage, e.g., a dosage of less than 12 mg/m$^2$, less than or equal to 24 mg/m$^2$, or greater than 24 mg/m$^2$. In particular embodiments, the onvansertib is administered to the patient daily. In additional embodiments, the onvansertib is administered in a cycle of 3-10 days of daily onvansertib administration with 2-16 days with no onvansertib administration.

In some embodiments, the combination treatment with onvansertib and FGFR inhibitor can be administered at the same dose as single treatment with onvansertib or FGFR inhibitor.

As can be appreciated by one of skill in the art, the amount of co-administration of the FGFR inhibitor and the PLK1 inhibitor, and the timing of co-administration, can depend on the type (species, gender, age, weight, etc.) and condition of the subject being treated and the severity of the disease or condition being treated. The FGFR inhibitor and the PLK1 inhibitor can be formulated into a single pharmaceutical composition, or two separate pharmaceutical compositions. The active ingredients may also be entrapped in microcapsules prepared, for example, by coacervation techniques or by interracial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Methods, compositions, kits and systems disclosed herein can be applied to different types of subjects. For example, the subject can be a subject receiving a cancer treatment, a subject at cancer remission, a subject has received one or more cancer treatment, or a subject suspected of having cancer. The subject can have a stage I cancer, a stage II cancer, a stage III cancer, and/or a stage IV cancer. The cancer can be head and neck cancer, non-small cell lung cancer, intrahepatic cholangiocarcinoma, gastric cancer, urothelial cancer, small cell lung cancer, endometrial cancer, cervical cancer, rhabdomyosarcoma, cholangiocarcinoma, liver cancer, ovarian cancer, breast cancer, prostate cancer, colorectal cancer, pancreatic cancer, or a combination thereof. The cancer can be an FGFR-altered cancer, such as FGFR-amplified cancer. The methods can further comprise administering an additional therapeutic intervention to the subject. The additional therapeutic intervention can comprise a different therapeutic intervention than administering the PLK1 inhibitor and the FGFR inhibitor, an antibody, an adoptive T cell therapy, a chimeric antigen receptor (CAR) T cell therapy, an antibody-drug conjugate, a cytokine therapy, a cancer vaccine, a checkpoint inhibitor, a radiation therapy, surgery, a chemotherapeutic agent, or any combination thereof. The therapeutic intervention can be administered at any time of the treatment, for example at a time when the subject has an early-stage cancer, and wherein the therapeutic intervention is more effective that if the therapeutic intervention were to be administered to the subject at a later time. Without being bound to any particular theory, it is believed that the PLK1 inhibitor (e.g., onvansertib) can sensitize cells (e.g., cancer cells) to FGFR inhibitor treatment to achieve effective cancer treatment.

Dosing and Pharmacokinetics

The treatment of the present disclosure can comprise administration of a PLK1 inhibitor (e.g., onvansertib) for a desired duration in one or more cycles of treatment, and administration of an FGFR inhibitor.

Daily administration of an FGFR inhibitor (e.g., AZD4547) can be at, or be at about, 20 mg, 50 mg, 100 mg, 200 mg, 300 mg, 400 mg, 500 mg, 600 mg, 700 mg, 800 mg, 900 mg, 1000 mg, 1100 mg, 1200 mg, or a number or a range between any two of these values. In some embodiments, the daily dose of the FGFR inhibitor (e.g., AZD4547) can be adjusted (e.g., increased or decreased with the range) during the treatment of the subject. The daily administration of the FGFR inhibitor can be at different amounts on different days or during different weeks. For example, the treatment can comprise daily administration of the FGFR inhibitor (e.g., AZD4547) at 20 mg during week 1, 50 mg during week 2, 100 mg during week 3, 200 mg during week 4, and 400 mg during week 5 and beyond. For example, the treatment can comprise daily administration of the FGFR inhibitor (e.g., AZD4547) at 100 mg on day 1, 200 mg on day 2, 400 mg on day 3, and 400 mg or 600 mg on day 4 and beyond.

A maximum concentration ($C_{max}$) of the FGFR inhibitor (e.g., AZD4547) in a blood of the subject (during the treatment or after the treatment) when the FGFR inhibitor is administered alone or in combination with the PLK1 inhibitor can be from about 0.1 mcg/mL to about 10 mcg/mL. For example, the $C_{max}$ of the FGFR inhibitor (e.g., AZD4547) in a blood of the subject when the FGFR inhibitor is administered alone or in combination with the PLK1 inhibitor can be, or be about, 0.1 µg/mL, 0.2 µg/mL, 0.3 µg/mL, 0.4 µg/mL, 0.5 µg/mL, 0.6 µg/mL, 0.7 µg/mL, 0.8 µg/mL, 0.9 µg/mL, 1 µg/mL, 1.1 µg/mL, 1.2 µg/mL, 1.3 µg/mL, 1.4 µg/mL, 1.5 µg/mL, 1.6 µg/mL, 1.7 µg/mL, 1.8 µg/mL, 1.9 µg/mL, 2 µg/mL, 2.1 µg/mL, 2.2 µg/mL, 2.3 µg/mL, 2.4 µg/mL, 2.5 µg/mL, 2.6 µg/mL, 2.7 µg/mL, 2.8 µg/mL, 2.9 µg/mL, 3 µg/mL, 3.1 µg/mL, 3.2 µg/mL, 3.3 µg/mL, 3.4 µg/mL, 3.5 µg/mL, 3.6 µg/mL, 3.7 µg/mL, 3.8 µg/mL, 3.9 µg/mL, 4 µg/mL, 4.1 µg/mL, 4.2 µg/mL, 4.3 µg/mL, 4.4 µg/mL, 4.5 µg/mL, 4.6 µg/mL, 4.7 µg/mL, 4.8 µg/mL, 4.9 µg/mL, 5 µg/mL, 5.1 µg/mL, 5.2 µg/mL, 5.3 µg/mL, 5.4 µg/mL, 5.5 µg/mL, 5.6 µg/mL, 5.7 µg/mL, 5.8 µg/mL, 5.9 µg/mL, 6 µg/mL, 6.1 µg/mL, 6.2 µg/mL, 6.3 µg/mL, 6.4 µg/mL, 6.5 µg/mL, 6.6 µg/mL, 6.7 µg/mL, 6.8 µg/mL, 6.9 µg/mL, 7 µg/mL, 7.1 µg/mL, 7.2 µg/mL, 7.3 µg/mL, 7.4 µg/mL, 7.5 µg/mL, 7.6 µg/mL, 7.7 µg/mL, 7.8 µg/mL, 7.9 µg/mL, 8 µg/mL, 8.1 µg/mL, 8.2 µg/mL, 8.3 µg/mL, 8.4 µg/mL, 8.5 µg/mL, 8.6 µg/mL, 8.7 µg/mL, 8.8 µg/mL, 8.9 µg/mL, 9 µg/mL, 9.1 µg/mL, 9.2 µg/mL, 9.3 µg/mL, 9.4 µg/mL, 9.5 µg/mL, 9.6 µg/mL, 9.7 µg/mL, 9.8 µg/mL, 9.9 µg/mL, 10 µg/mL, a range between any two of these values, or any value between 0.1 mcg/mL to 10 mcg/mL.

An area under curve (AUC) of a plot of a concentration of the FGFR inhibitor (e.g., AZD4547) in a blood of the subject over time (e.g., $AUC_{0-24}$ for the first 24 hours after administration) when the FGFR inhibitor is administered alone or in combination with the PLK1 inhibitor can be from about 10 µg·h/mL to about 100 µg·h/mL. For example, the AUC of a plot of a concentration of the FGFR inhibitor (e.g., AZD4547)) in a blood of the subject over time (e.g., $AUC_{0-24}$ for the first 24 hours after administration) when the FGFR inhibitor is administered alone or in combination with the PLK1 inhibitor can be, or be about, 1 µg·h/mL, 2 µg·h/mL, 3 µg·h/mL, 4 µg·h/mL, 5 µg·h/mL, 6 µg·h/mL, 7 µg·h/mL, 8 µg·h/mL, 9 µg·h/mL, 10 µg·h/mL, 11 µg·h/mL, 12 µg·h/mL, 13 µg·h/mL, 14 µg·h/mL, 15 µg·h/mL, 16 µg·h/mL, 17 µg·h/mL, 18 µg·h/mL, 19 µg·h/mL, 20 µg·h/mL, 21 µg·h/mL, 22 µg·h/mL, 23 µg·h/mL, 24 µg·h/mL, 25 µg·h/mL, 26 µg·h/mL, 27 µg·h/mL, 28 µg·h/mL, 29 µg·h/mL, 30 µg·h/mL, 31 µg·h/mL, 32 µg·h/mL, 33 µg·h/mL, 34 µg·h/mL, 35 µg·h/mL, 36 µg·h/mL, 37 µg·h/mL, 38 µg·h/mL, 39 µg·h/mL, 40 µg·h/mL, 41 µg·h/mL, 42 µg·h/mL, 43 µg·h/mL, 44 µg·h/mL, 45 µg·h/mL, 46 µg·h/mL, 47 µg·h/mL, 48 µg·h/mL, 49 µg·h/mL, 50 µg·h/mL, 51 µg·h/mL, 52 µg·h/mL, 53 µg·h/mL, 54 µg·h/mL, 55 µg·h/mL, 56 µg·h/mL, 57 µg·h/mL, 58 µg·h/mL, 59 µg·h/mL, 60 µg·h/mL, 61 µg·h/mL, 62 µg·h/mL, 63 µg·h/mL, 64 µg·h/mL, 65 µg·h/mL, 66 µg·h/mL, 67 µg·h/mL, 68 µg·h/mL, 69 µg·h/mL, 70 µg·h/mL, 71 µg·h/mL, 72 µg·h/mL, 73 µg·h/mL, 74 µg·h/mL, 75 µg·h/mL, 76 µg·h/mL, 77 µg·h/mL, 78 µg·h/mL, 79 µg·h/mL, 80 µg·h/mL, 81 µg·h/mL, 82 µg·h/mL, 83 µg·h/mL, 84 µg·h/mL, 85 µg·h/mL, 86 µg·h/mL, 87 µg·h/mL, 88 µg·h/mL, 89 µg·h/mL, 90 µg·h/mL, 91 µg·h/mL, 92 µg·h/mL, 93 µg·h/mL, 94 µg·h/mL, 95 µg·h/mL, 96 µg·h/mL, 97 µg·h/mL, 98 µg·h/mL, 99 µg·h/mL, 100 µg·h/mL, a range between any two of these values, or any value between 10 µg·h/mL and 100 µg·h/mL.

A time ($T_{max}$) to reach a maximum concentration of the FGFR inhibitor (e.g., AZD4547) in a blood of the subject when the FGFR inhibitor is administered alone or in combination with the PLK1 inhibitor can be from about 3 hours to 10 hours. For example, the time ($T_{max}$) to reach a maximum concentration of the FGFR inhibitor (e.g., AZD4547) in a blood of the subject when the FGFR inhibitor is administered alone or in combination with the PLK1 inhibitor can be, or be about, 3 hours, 4 hours, 5 hours, 6 hours, 7 hours, 8 hours, 9 hours, 10 hours, a range between any two of these values, or any value between 3 hours and 10 hours.

An elimination half-life ($T_{1/2}$) of the FGFR inhibitor (e.g., AZD4547) in a blood of the subject when the FGFR inhibitor is administered alone or in combination with the PLK1 inhibitor can be from about 15 hours to about 60 hours. For example, the elimination half-life ($T_{1/2}$) of the FGFR inhibitor (e.g., olaparib) in a blood of the subject when the FGFR inhibitor is administered alone or in combination with the PLK1 inhibitor can be, or be about, 15 hours, 20 hours, 25 hours, 30 hours, 35 hours, 40 hours, 45 hours, 50 hours, 55 hours, 60 hours, a range between any two of these values, or any value between 15 hours and 60 hours.

The treatment of the present disclosure can comprise administration of a PLK1 inhibitor (onvansertib) for a desired duration in a cycle. The administration of the PLKs inhibitor (and/or the one or more chemotherapeutic agents) can be daily or with break(s) between days of administrations. The break can be, for example, 1 day, 2 days, 3 days, 4 days, 5 days, 6 days, 7 days, 8 days, 9 days, 10 days, 11 days, 12 days, 13 days, 14 days, or more. The administration can be once, twice, three times, four times, or more on a day when the PLK1 inhibitor (and/or the one or more chemotherapeutic agents) is administered to the patient. The administration can be, for example, once every two days, every three days, every four days, every five days, every six days, or every seven days. The length of the desired duration can vary, for example, 1, 2, 3, 4, 5, 6, 7, 8, 9, 10, 11, 12, 13, 14, 15, 16, 17, 18, 19, 20, 21, 22, 23, 24, 25, 26, 27, 28, or more days. Each cycle of treatment can have various lengths, for example, at least 14 days, 15 days, 16 days, 17 days, 18 days, 19 days, 20 days, 21 days, 22 days, 23 days, 24 days, 25 days, 26 days, 27 days, 28 days, or more. For example, a single cycle of the treatment can comprise administration of the PLK1 inhibitor (e.g., onvansertib) and/or the one or more chemotherapeutic agents for four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, or more in a cycle (e.g., in a cycle of at least 21 days (e.g., 21 to 28 days)). In some embodiments, the treatment can comprise administration of the PLK1 inhibitor (e.g., onvansertib) and/or the one or more chemotherapeutic agents for, or for at least, four days, five days, six days, seven days, eight days, nine days, ten days, eleven days, twelve days, thirteen days, fourteen days, fifteen days, sixteen days, seventeen days, eighteen days, nineteen days, twenty days, or a range between any two of these values, in a cycle (e.g., a cycle of at least 21 days (e.g., 21 to 28 days)). The administration of the PLK1 inhibitor (e.g., onvansertib) and/or the one or more chemotherapeutic agents in a single cycle of the treatment can be continuous or with one or more intervals (e.g., one day or two days of break). In some embodiments, the treatment comprises administration of the PLK1 inhibitor (e.g., onvansertib) for five days in a cycle of 21 to 28 days.

In some embodiments, the PLK1 inhibitor (e.g., onvansertib) is administered to the subject in need thereof on twenty days (e.g., Days 1-10 and 15-24) during a 28-day cycle. The twenty days can be, for example, a continuous daily administration for ten days (e.g., Days 1-10) and another continuous daily administration (e.g., Days 15-24) for ten days, or a continuous daily administration for four sets of five days (e.g., Days 1-5, 8-12, 15-19, and 22-26). In some embodiments, for example when the patient is identified to have low tolerance to the PLK1 inhibitor (e.g., onvansertib), the PLK1 inhibitor is administered to the subject in need thereof on ten days (e.g., Days 1-5 and 15-19) during a 28-day cycle. The ten days can be, for example, a continuous daily administration for ten days (e.g., Days 1-10) or two continuous daily admiration for five days each (e.g., Days 1-5 and Days 15-19). In some embodiments, the PLK1 inhibitor (e.g., onvansertib) is administered to the subject in need thereof daily throughout the whole cycle (e.g., daily for 28 days in a cycle of 28 days). Depending on the needs of inhibition/reversion of cancer progression in the subject, the subject can receive one, two, three, four, five, six, or more cycles of treatment.

The treatment can comprise administration of the PLK1 inhibitor (e.g., onvansertib) at, or at about, 6 mg/m$^2$-90 mg/m$^2$, for example, as a daily dose. For example, the treatment can comprise daily administration of the PLK1 inhibitor (e.g., onvansertib) at, or at about, 6 mg/m$^2$, 8 mg/m$^2$, 10 mg/m$^2$, 12 mg/m$^2$, 14 mg/m$^2$, 16 mg/m$^2$, 18 mg/m$^2$, 20 mg/m$^2$, 23 mg/m$^2$, 27 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 80 mg/m$^2$, 85 mg/m$^2$, 90 mg/m$^2$, a number or a range between any two of these values, or any value between 8 mg/m$^2$-90 mg/m$^2$. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the PLK inhibitor (e.g., onvansertib) is administered at 12 mg/m$^2$ on twenty days (e.g., Days 1-10 and 15-24) during a 28-day cycle. In some embodiments, the PLK inhibitor (e.g., onvansertib) is administered at 15 mg/m$^2$ on ten days (e.g., Days 1-5 and 15-19) during a 28-day cycle. In some embodiments, the PLK1 inhibitor (e.g., onvansertib) is administered at 8 mg/m$^2$ or 10 mg/m$^2$ everyday (e.g., Days 11-28) during a 28-day cycle. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject.

A maximum concentration ($C_{max}$) of the PLK1 inhibitor (e.g., onvansertib) in a blood of the subject (during the treatment or after the treatment) when the PLK1 inhibitor is administered alone or in combination with the FGFR inhibitor can be from about 100 nmol/L to about 1500 nmol/L. For example, the $C_{max}$ of the PLK1 inhibitor (e.g., onvansertib) in a blood of the subject when the PLK1 inhibitor is administered alone or in combination with the FGFR inhibitor can be, or be about, 100 nmol/L, 200 nmol/L, 300 nmol/L, 400 nmol/L, 500 nmol/L, 600 nmol/L, 700 nmol/L, 800 nmol/L, 900 nmol/L, 1000 nmol/L, 1100 nmol/L, 1200 nmol/L, 1300 nmol/L, 1400 nmol/L, 1500 nmol/L, a range between any two of these values, or any value between 200 nmol/L to 1500 nmol/L.

An area under curve (AUC) of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with the FGFR inhibitor can be from about 1000 nmol/L·hour to about 400000 nmol/L·hour. For example, the AUC of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with the FGFR inhibitor can be, or be about, 1000 nmol/L·hour, 5000 nmol/L·hour, 10000 nmol/L·hour, 15000 nmol/L·hour, 20000 nmol/L·hour, 25000 nmol/L·hour, 30000 nmol/L·hour, 35000 nmol/L·hour, 40000 nmol/L·hour, a range between any two of these values, or any value between 1000 nmol/L·hour and 400000 nmol/L·hour.

A time ($T_{max}$) to reach a maximum concentration of the PLK1 inhibitor (e.g., onvansertib) in a blood of the subject when the PLK1 inhibitor is administered alone or in combination with the FGFR inhibitor can be from about 1 hour to about 5 hours. For example, the time ($T_{max}$) to reach a maximum concentration of the PLK1 inhibitor (e.g., onvansertib) in a blood of the subject when the PLK1 inhibitor is administered alone or in combination with the FGFR inhibitor can be, or be about, 1 hour, 1.5 hours, 2 hours, 2.5 hours, 3 hours, 3.5 hours, 4 hours, 4.5 hours, 5 hours, a range between any two of these values, or any value between 1 hour and 5 hours.

An elimination half-life ($T_{1/2}$) of the PLK1 inhibitor (e.g., onvansertib) in a blood of the subject when the PLK1 inhibitor is administered alone or in combination with the FGFR inhibitor can be from about 10 hours to about 60 hours. For example, the elimination half-life ($T_{1/2}$) of the PLK1 inhibitor (e.g., onvansertib) in a blood of the subject when the PLK1 inhibitor is administered alone or in combination with the FGFR inhibitor can be, or be about, 10 hours, 15 hours, 20 hours, 25 hours, 30 hours, 35 hours, 40 hours, 45 hours, 50 hours, 55 hours, 60 hours, a range between any two of these values, or any value between 10 hours and 60 hours.

Additional Cancer Therapeutics or Therapy

Methods, compositions and kits disclosed herein can be used for treating cancer, for example lung cancer. In some embodiments, a method for treating cancer comprises administrating an FGFR inhibitor and a PLK1 inhibitor (e.g., onvansertib) to a subject (e.g., a patient) in need thereof. The method can comprise administering a therapeutically effective amount of the FGFR inhibitor and a therapeutically effective amount of the PLK1 inhibitor. The treatment can comprise administration of at least one additional cancer therapeutics or cancer therapy. The treatment can comprise administration a therapeutically effective amount of at least one additional cancer therapeutics or cancer therapy. The FGFR inhibitor and the cancer therapeutics or cancer therapy can, for example, co-administered simultaneously or sequentially. The PLK1 inhibitor (e.g., onvansertib) and the cancer therapeutics or cancer therapy can, for example, co-administered simultaneously or sequentially.

Methods for Predicting/Determining Treatment Efficacy and Status for Cancer

Also disclosed herein include methods, compositions, kits, and systems for predicting/determining clinical outcome for a combination treatment of cancer of the present disclosure, monitoring of the combination treatment, predicting/determining responsiveness of a subject to the combination treatment, determining the status of the cancer in a subject, and improving combination treatment outcome. The methods, compositions, kits and systems can be used to guide the combination treatment, provide combination treatment recommendations, reduce or avoid unnecessary ineffective combination treatment for patients. ctDNA can be analyzed to predict/determine clinical outcome for cancer treatment using a combination of an FGFR inhibitor and a PLK1 inhibitor of the present disclosure, monitor the combination treatment, predict/determine responsiveness of a subject to the combination treatment, determine cancer status in a subject, improve combination treatment outcome, guide combination treatment, provide combination treatment recommendations, and/or to reduce or avoid ineffective combination treatment. ctDNA can be analyzed to predict/determine clinical outcome for cancer treatment, monitor cancer treatment, predict/determine responsiveness of a subject to a cancer treatment, determine cancer status in a subject, improve cancer treatment outcome, guide cancer treatment, provide treatment recommendations, and/or to reduce or avoid ineffective cancer treatment. Such analysis of ctDNA has been described in PCT Application No. PCT/US2021/013287, the content of which is incorporated herein by reference in its entirety.

A method of determining responsiveness of a subject to a combination treatment comprising an FGFR inhibitor and a PLK1 inhibitor of the disclosure can comprise, for example, analyzing circulating tumor DNA (ctDNA) of a subject with cancer, the subject is undergoing a treatment and/or has received the combination treatment, thereby determining the responsiveness of the subject to the combination treatment. In some embodiments, determining the responsiveness of the subject comprises determining if the subject is a responder of the treatment, if the subject is or is going to be in complete remission (CR), or if the subject is or is going to be in partial remission (PR). For example, analyzing ctDNA can comprise detecting variant allele frequency in the ctDNA in a first sample obtained from the subject at a first time point, detecting variant allele frequency in the ctDNA obtained from the subject at one or more additional time points in one or more additional samples, and determining the difference of the variant allele frequency in ctDNA between the first and at least one of the one or more additional samples, a decrease in the variant allele frequency in at least one of the additional samples relative to the first sample indicates the subject as responsive to the cancer treatment.

In some embodiments, the first time point is prior or immediately prior to the combination treatment, and at least one of the one or more additional time points are at the end of or after at least a cycle of the combination treatment. In some embodiments, the cycle of the combination treatment is the first cycle of the combination treatment. In some embodiments, the first time point is prior or immediately prior to a first cycle of the combination treatment, and the one or more additional time points are at the end of or after a second cycle of the combination treatment. In some embodiments, the first cycle of the combination treatment is immediately prior to the second cycle of the combination treatment. In some embodiments, the method comprises continuing the combination treatment to the subject if the subject is indicated as responsive to the combination treatment. In some embodiments, the method comprises discontinuing the combination treatment to the subject and/or starting a different combination treatment to the subject if the subject is not indicated as responsive to the combination treatment.

Disclosed herein include methods of determining cancer status of a subject, comprising analyzing circulating tumor DNA (ctDNA) of a subject, thereby determining cancer status of the subject. The subject can be a subject undergoing a current combination treatment comprising an FGFR inhibitor and a PLK1 inhibitor of the present disclosure, a subject that has received a prior combination treatment of the present disclosure, and/or a subject that is in remission for the cancer. The subject in remission for cancer can be in complete remission (CR), or in partial remission (PR).

In some embodiments, analyzing the ctDNA comprises detecting variant allele frequency in the ctDNA. In some embodiments, analyzing the ctDNA comprises detecting variant allele frequency in the ctDNA obtained from the subject at a first time point in a first sample, detecting variant allele frequency in the ctDNA obtained from the subject at one or more additional time points in one or more additional samples, and determining the difference of the variant allele frequency in ctDNA between the first and at least one of the one or more additional samples, an increase in the variant allele frequency at the additional sample(s) relative to the first sample indicates that the subject is at risk of cancer relapse or is in cancer relapse.

In some embodiments, the first time point is prior or immediately prior to the combination treatment, and the one or more additional time points are at the end of or after at least a cycle of the combination treatment, optionally the cycle of the combination treatment is the first cycle of the combination treatment. In some embodiments, the first time point is prior or immediately prior to a first cycle of the combination treatment, and the one or more additional time points are at the end of or after a second cycle of the combination treatment, optionally the first cycle of the combination treatment is immediately prior to the second cycle of the combination treatment.

In some embodiments, the method comprises starting an additional treatment to the subject if the subject is indicated as in cancer relapse. The additional treatment can be the same or different from the current or prior combination treatment.

The variant allele frequency in ctDNA can be determined, for example, by total mutation count in the ctDNA in each of the first sample and one or more additional samples, or by the mean variant allele frequency in each of the first sample and one or more additional samples. In some embodiments, the variant allele frequency is mutant allelic frequency (MAF) for a driver mutation of the cancer (e.g., ovarian cancer, breast cancer, prostate cancer, colorectal cancer, pancreatic cancer, or a combination thereof). In some embodiments, the variant allele frequency is MAF for one or more driver mutations of the cancer (e.g., ovarian cancer, breast cancer, prostate cancer, colorectal cancer, pancreatic cancer, or a combination thereof). In some embodiments, $\text{Log}_2(C_1/C_0) < a$ MAF threshold indicates a decrease in ctDNA MAF $C_0$ is ctDNA MAF in the first sample and $C_1$ is ctDNA MAF in one of the additional samples. In some embodiments, the MAF threshold is, or is about, 0.01 to −0.10. In some embodiments, the MAF threshold is, or is about, 0.06. In some embodiments, the MAF threshold is, or is about, 0.05.

In some embodiments, the first sample comprises ctDNA from the subject before treatment, and the one of additional samples comprises ctDNA from the subject after treatment. In some embodiments, the driver mutation is a mutation in one of the below 75 genes ABL1, ANKRD26, ASXL1, ATRX, BCOR, BCORL1, BRAF, BTK, CALR, CBL, CBLB, CBLC, CCND2, CDC25C, CDKN2A, CEBPA, CSF3R, CUX1, CXCR4, DCK, DDX41, DHX15, DNMT3A, ETNK1, ETV6, EZH2, FBXW7, FLT3, GATA1, GATA2, GNAS, HRAS, IDH1, IDH2, IKZF1, JAK2, JAK3, KDM6A, KIT, KMT2A, KRAS, LUC7L2, MAP2K1, MPL, MYC, MYD88, NF1, NOTCH1, NPM1, NRAS, PDGFRA, PHF6, PPM1D, PTEN, PTPN11, RAD21, RBBP6, RPS14, RUNX1, SETBP1, SF3B1, SH2B3, SLC29A1, SMC1A, SMC3, SRSF2, STAG2, STAT3, TET2, TP53, U2AF1, U2AF2, WT1, XPO1, and ZRSR2. In some embodiments, at least one of the one or more the driver mutations is a mutation in in the 75 genes. In some embodiments, one or more the driver mutations are mutations in the 75 genes.

The driver mutation or at least one of the one or more driver mutations can be in a gene selected from the group consisting of TP53, ASXL1, DNMT3A, NRAS, SRSF2, TET2, SF3B1, FLT3, FLT3 ITD, IDH2, NPM1, RUNX1, CDKN2A, KRAS, STAG2, CALR, CBL, CSF3R, DDX41, GATA2, JAK2, PHF6, and SETBP1. In some embodiments, the driver mutation or at least one of the one or more driver mutations is in a gene selected from the group consisting of DNMT3A, TET2, NPM1, SRSF2, NRAS, CDKN2A, SF3B1, FLT3, ASXL1, SRSF2, IDH2, NRAS, and SF3B1. In some embodiments, the method further comprises determining variant allele frequency in one or more of the ctDNA, PBMCs and BMMCs of the subject.

The ctDNA can be analyzed using, for example, polymerase chain reaction (PCR), next generation sequencing (NGS), and/or droplet digital PCR (ddPCR). The sample disclosed herein can be derived from, for example, whole blood of the subject, plasma of the subject, serum of the subject, or a combination thereof. In some embodiments, the ctDNA is from whole blood of the subject, plasma of the subject, serum of the subject, or a combination thereof.

In some embodiments, the method comprises analyzing ctDNA of the subject before the treatment. In some embodiments, the treatment comprises one or more cycles, and the ctDNA is analyzed before, during and after each cycle of the treatment. Each cycle of treatment can be at least 21 days. In some embodiments, each cycle of treatment is from about 21 days to about 28 days. In some embodiments, the subject is human.

Disclosed herein include methods of improving treatment outcome for the cancer. The method can comprise: detecting variant allele frequency in circulating tumor DNA (ctDNA) obtained from a subject at a first time point in a first sample before the subject undergoes a combination treatment comprising an FGFR inhibitor and a PLK1 inhibitor of the present disclosure; detecting variant allele frequency in ctDNA obtained from the subject at one or more additional time points in one or more additional samples after the subject undergoes the combination treatment; determining the difference of the variant allele frequency in ctDNA between the first and at least one of the one or more additional samples, a decrease in the variant allele frequency in at least one of the additional samples relative to the first sample indicates the subject as responsive to the combination treatment; and continuing the combination treatment to the subject if the subject is indicated as responsive to the combination treatment, or discontinuing the combination treatment to the subject and/or starting a different cancer treatment to the subject if the subject is not indicated as responsive to the combination treatment.

Also disclosed herein include methods of treating cancer The method can comprise: administering a combination treatment comprising an FGFR inhibitor and a PLK1 inhibitor of the present disclosure to a subject in need thereof; determining a decrease, relative to a variant allele frequency in a first sample of the subject obtained at a first time point before the subject receives the combination treatment, in a variant allele frequency in a second sample of the subject obtained at a second time point after the subject receives the combination treatment; and continuing with the combination treatment. In some embodiments, the subject is a subject newly diagnosed with cancer, for example a subject that has not received any prior cancer treatment before the combination treatment. In some embodiments, the subject has received prior cancer treatment and was in remission for the cancer, for example a subject in complete remission (CR), or in partial remission (PR) after receiving the prior combination treatment.

The first time point can be, for example, prior or immediately prior to the combination treatment. The at least one of the one or more additional time points can be, for example, at the end of or after at least a cycle of the combination treatment. In some embodiments, the cycle of the combination treatment is the first cycle of the combination treatment. In some embodiments, the first time point is prior or immediately prior to a first cycle of the combination treatment, and the one or more additional time points are at the end of or after a second cycle of the combination treatment. In some embodiments, the first cycle of the combination treatment is immediately prior to the second cycle of the combination treatment.

The variant allele frequency in ctDNA can be determined, for example, by total mutation count in the ctDNA in each of the first sample and one or more additional samples, and/or by the mean variant allele frequency in each of the first sample and one or more additional samples. In some embodiments, the variant allele frequency is mutant allelic frequency (MAF) for a driver mutation of the cancer (e.g., ovarian cancer, breast cancer, prostate cancer, colorectal cancer, pancreatic cancer, or a combination thereof). In some embodiments, the variant allele frequency is mutant allelic frequency (MAF) for one or more driver mutations of the cancer (e.g., ovarian cancer, breast cancer, prostate cancer, colorectal cancer, pancreatic cancer, or a combination thereof). In some embodiments, $Log_2(C_1/C_0)<a$ MAF threshold indicates a decrease in ctDNA MAF. $C_0$ is ctDNA MAF in the first sample and $C_1$ is ctDNA MAF in one of the additional samples. In some embodiments, the MAF threshold is −0.05.

The driver mutation can be, for example, a mutation in one of the 75 genes set forth in Table 3, at least one of the one or more the driver mutations is a mutation in one of the below 75 genes ABL1, ANKRD26, ASXL1, ATRX, BCOR, BCORL1, BRAF, BTK, CALR, CBL, CBLB, CBLC, CCND2, CDC25C, CDKN2A, CEBPA, CSF3R, CUX1, CXCR4, DCK, DDX41, DHX15, DNMT3A, ETNK1, ETV6, EZH2, FBXW7, FLT3, GATA1, GATA2, GNAS, HRAS, IDH1, IDH2, IKZF1, JAK2, JAK3, KDM6A, KIT, KMT2A, KRAS, LUC7L2, MAP2K1, MPL, MYC, MYD88, NF1, NOTCH1, NPM1, NRAS, PDGFRA, PHF6, PPM1D, PTEN, PTPN11, RAD21, RBBP6, RPS14, RUNX1, SETBP1, SF3B1, SH2B3, SLC29A1, SMC1A, SMC3, SRSF2, STAG2, STAT3, TET2, TP53, U2AF1, U2AF2, WT1, XPO1, and ZRSR2, and/or one or more the driver mutations are mutations in the 75 genes. In some embodiments, the driver mutation or at least one of the one or more driver mutations is in a gene selected from the group consisting of TP53, ASXL1, DNMT3A, NRAS, SRSF2, TET2, SF3B1, FLT3, FLT3 ITD, IDH2, NPM1, RUNX1, CDKN2A, KRAS, STAG2, CALR, CBL, CSF3R, DDX41, GATA2, JAK2, PHF6, and SETBP1. In some embodiments, the driver mutation or at least one of the one or more driver mutations is in a gene selected from the group consisting of DNMT3A, TET2, NPM1, SRSF2, NRAS, CDKN2A, SF3B1, FLT3, ASXL1, SRSF2, IDH2, NRAS, and SF3B1.

In some embodiments, the method further comprises determining variant allele frequency in one or more of the ctDNA, PBMCs and BMMCs of the subject. The variant allele frequency in ctDNA can be detected, for example, using polymerase chain reaction (PCR) or next generation sequencing (NGS). In some embodiments, the variant allele frequency in ctDNA is detected using droplet digital PCR (ddPCR).

At least one of the first sample, the one or more additional samples, and the second sample can be derived from whole blood of the subject, plasma of the subject, serum of the subject, or a combination thereof. In some embodiments, the ctDNA is from whole blood of the subject, plasma of the subject, serum of the subject, or a combination thereof.

In some embodiments, the subject whose ctDNA is analyzed is undergoing or will be undergoing treatment for the cancer. The method can comprise analyzing ctDNA of the subject before the treatment. The treatment can comprise one or more cycles, and the ctDNA is analyzed before, during and after one or more cycles of the treatment. For example, the ctDNA can be analyzed before, during and after two or more cycle of the treatment, three or more cycle of the treatment, or each cycle of the treatment. Each cycle of treatment can be at least 21 days, for example, 21 days, 22 days, 23 days, 24 days, 25 days, 26 days, 27 days, 28 days, 29 days, 30 days, or more, or a range between any two of these values. In some embodiments, each cycle of treatment is from about 21 days to about 28 days. In some embodiments, each cycle of treatment is from 21 days to 28 days. In some embodiments, the subject is human.

Compositions and Kits

Disclosed herein include compositions and kits for treating cancer. In some embodiments, a kit comprises: a Polo-like kinase 1 (PLK1) inhibitor; and a manual providing instructions for co-administrating the PLK1 inhibitor with an FGFR inhibitor to a subject for treating cancer. In some embodiments, the kit comprises the FGFR inhibitor. The cancer can be, for example, ovarian cancer, breast cancer, prostate cancer, colorectal cancer, pancreatic cancer, or a combination thereof.

In some embodiments, the subject has cancer (e.g., head and neck cancer, non-small cell lung cancer, small-cell lung cancer, intrahepatic cholangiocarcinoma, gastric cancer, urothelial cancer, breast cancer, endometrial cancer, cervical cancer, rhabdomyosarcoma, cholangiocarcinoma, glioblastoma, low-grade glioma, thyroid carcinoma, gallbladder cancer, ovarian cancer, prostate cancer, or a combination thereof). In some embodiments, the instructions comprise instructions for co-administrating the PLK inhibitor and the FGFR inhibitor simultaneously. In some embodiments, the instructions comprise instructions for co-administrating the PLK inhibitor and the FGFR inhibitor sequentially. In some embodiments, the instructions comprise instructions for administering of the PLK1 inhibitor orally. In some embodiments, the instructions comprise instructions for administrating the FGFR inhibitor orally.

In some embodiments, the instructions comprise instructions the subject has received a prior FGFR inhibitor treatment. In some embodiments, the instructions comprise instructions the subject did not respond to treatment with the FGFR inhibitor alone. In some embodiments, the instructions comprise instructions the subject is known to be resistant to an FGFR inhibitor therapy.

In some embodiments, the instructions comprise instructions the subject has received at least one prior treatment for the cancer. In some embodiments, the prior treatment does not comprise the use of an FGFR inhibitor, a PLK inhibitor, or both. In some embodiments, the instructions comprise instructions the subject was in remission for the cancer. In some embodiments, the subject in remission for cancer was in complete remission (CR), or in partial remission (PR).

In some embodiments, the instructions comprise instructions for administering each of the FGFR inhibitor and the PLK1 inhibitor to the subject in a cycle of at least twice within a week. In some embodiments, the instructions comprise instructions for administering each of the FGFR inhibitor and the PLK1 inhibitor to the subject in a cycle of at least five times within a week. In some embodiments, the instructions comprise instructions for administering the FGFR inhibitor, the PLK1 inhibitor, or both are in a cycle of at least 7 days. In some embodiments, each cycle of treatment is at least about 21 days. In some embodiments, each cycle of treatment is from about 21 days to about 28 days. In some embodiments, the instructions comprise instructions for administering the PLK1 inhibitor on at least four days in the cycle. In some embodiments, the instructions comprise instructions for not administering the PLK1 inhibitor on at least one day in the cycle. In some embodiments, the instructions comprise instructions for administrating the FGFR inhibitor daily. In some embodiments, the instructions comprise instructions for administrating the FGFR inhibitor and the PLK1 inhibitor for at least two cycles.

In some embodiments, the FGFR inhibitor is small-molecule TKIs, particularly pan-FGFR inhibitor. In some embodiments, the FGFR inhibitor is Sunitibib, Pazopanib, Anlotinib, MAX-40279, Zotatifin, Derazantinib, Aprutumab, LY3076226, Bemarituzumab, Vofatamab, MFGR1877S, AZD4547, Rogaratinib, Pemigatinib, Futibatinib, Debio 1347, Roblitinib, E7090, Fisogatinib, LY2874455, Alofanib, CPL-304-110, PRN1371, INCB062079, Ponatinib, Regorafenib, Dovitinib, Nintedanib, Erdafitinib, CH5183284, infigratinib (BGJ398), Rogaratinib, Futibatinib (TAS-120), Fisogatinib (BLU-554), roblitinib (FGF401), H3B-6527, E7090, HMPL-453, Anlotinib, TKI258, Lucitanib, RLY-4008, EVER4010001, or a combination thereof. In some embodiments, the FGFR inhibitor is AZD4547, LY2874455, CH5183284, FGF401, Infigratinib, Erdafitinib, Rogaratinib, Pemigatinib, Futibatinib, fisogatinib, roblitinib, INCB062079, PRN1371, H3B-6527 or a combination thereof. In some embodiments, the FGFR inhibitors is AZD4547.

In some embodiments, the PLK1 inhibitor is selective and/or specific for PLK1. In some embodiments, the PLK1 inhibitor is a dihydropteridinone, a pyridopyrimidine, a aminopyrimidine, a substituted thiazolidinone, a pteridine derivative, a dihydroimidazo[1,5-f]pteridine, a metasubstituted thiazolidinone, a benzyl styryl sulfone analogue, a stilbene derivative, or any combination thereof. In some embodiments, the PLK1 inhibitor is onvansertib, BI2536, Volasertib (BI 6727), GSK461364, AZD1775, CYC140, HMN-176, HMN-214, rigosertib (ON-01910), MLN0905, TKM-080301, TAK-960 or Ro3280. In some embodiments, the PLK1 inhibitor is onvansertib. In some embodiments, the FGFR inhibitor is AZD4547, and the PLK1 inhibitor is onvansertib.

In some embodiments, the instructions comprise instructions for administering the PLK1 inhibitor at 8 mg/m$^2$-90 mg/m$^2$. In some embodiments, the instructions comprise instructions for administering the FGFR inhibitor at 20 mg-1200 mg.

The methods, compositions and kits disclosed herein can also be used to sensitize cancer cells to one or more FGFR inhibitors. The method can comprise contacting cancer cells with a composition comprising a PLK1 inhibitor (e.g., onvansertib), or a pharmaceutically acceptable salt, solvate, stereoisomer thereof, thereby sensitizing the cancer cells to the one or more FGFR inhibitors (e.g., AZD4547). Contacting cancer cells with the composition can occur in vitro, ex vivo, in vivo, or in any combination. In some embodiments, contacting cancer cells with the composition is in a subject's body. In some embodiments, cancer cells are contacted with the composition in a cell culture. The subject can be a mammal, for example a human. The sensitization of the cancer cells can increase the responsiveness of the cancer cells to the one or more FGFR inhibitors by, or by about, 1%, 5%, 10%, 15%, 20%, 25%, 30%, 35%, 40%, 45%, 50%, 55%, 60%, 65%, 70%, 75%, 80%, 85%, 90%, 95%, or a range between any two of these values. The sensitization of the cancer cells can increase the responsiveness of the cancer cells to the one or more FGFR inhibitors by at least, or by at least about, 1%, 5%, 10%, 15%, 20%, 25%, 30%, 35%, 40%, 45%, 50%, 55%, 60%, 65%, 70%, 75%, 80%, 85%, 90%, 95%, or a range between any two of these values. The increase of the responsiveness of the cancer cells is, in some embodiments, relative to the untreated cancer cells. The sensitization of the cancer cells can increase the responsiveness of the subject having the cancer cells to one or more FGFR inhibitors by, or by about, 1%, 5%, 10%, 15%, 20%, 25%, 30%, 35%, 40%, 45%, 50%, 55%, 60%, 65%, 70%, 75%, 80%, 85%, 90%, 95%, or a range between any two of these values. The sensitization of the cancer cells can increase the responsiveness of the subject having the cancer cells to the one or more FGFR inhibitors by at least, or by at least about, 1%, 5%, 10%, 15%, 20%, 25%, 30%, 35%, 40%, 45%, 50%, 55%, 60%, 65%, 70%, 75%, 80%, 85%, 90%, 95%, or a range between any two of these values. The increase of the responsiveness of the subject having the cancer cells is, in some embodiments, relative to the subjects untreated with the composition.

The sensitization of the cancer cells can, for example, reduce the colony forming capacity of the cancer cells by, by at least, or by at least about, 20%, 25%, 30%, 35%, 40%, 45%, 50%, 55%, 60%, 65%, 70%, 75%, 80%, 85%, 90%, 95%, or a range between any two of these values. The decrease of the colony-forming capacity of the cancer cells is, in some embodiments, relative to the cancer cells untreated with the composition. The sensitization of the cancer cells can increase the relative number of cells in G2 and/or mitotic stages by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the expression of mitotic markers, such as phosphorylated nucleophosmin (NPM) on Threonine 199, in the cancer cells by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the percentage of cancer cells expressing phosphorylated histone H3 (pHH3) by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the percentage of cancer cells expressing cleaved caspase-3 by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the expression of the apoptotic markers, such as cleaved caspase-3 and cleaved PARP, by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the expression of DNA damage markers, such as γ-H2AX, by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The sensitization of the cancer cells can increase the percentage of cancer cells expressing γ-H2AX by at least 1.5 folds, 2 folds, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values. The increase of the relative number of cells in G2 and/or mitotic stages, of the expression of phosphorylated NPM (Thr199), cleaved caspase 3, cleaved PARP and γH2AX, of the percentage of cancer cells expressing pHH3, cleaved caspase-3 and γ-H2AX is, in some embodiments, relative to those in the cancer cells or subjects untreated with the composition.

The method can comprise determining sensitization of the cancer cells to the one or more FGFR inhibitors after being contacted with the PLK1 inhibitor. The method can comprise contacting the cancer cells with the one or more FGFR inhibitors concurrently and/or after being contacted with the PLK1 inhibitor. In some embodiments, contacting the cancer cells with the one or more FGFR inhibitors occurs in the body of a subject. The subject can be a mammal, for example human. The subject can be, for example, a subject that did not respond to, or is known to be resistant to, FGFR inhibitors alone. The subject can be, for example, a subject that had prior treatment with one of the one or more FGFR inhibitors. In some embodiments, the method comprises determining the response of the subject to the one or more FGFR inhibitors.

EXAMPLES

Some aspects of the embodiments discussed above are disclosed in further detail in the following example, which are not in any way intended to limit the scope of the present disclosure.

Example 1

Antitumor Activity of the Combination of AZD4547 and Onvansertib in Two FGFR1-Amplified SqLC Cell Lines In this example, the efficacy of onvansertib in combination with AZD4547 was evaluated in two FGFR1-amplified lung SqLC cancer cell lines: NCI-H1703 (H1703) and NCI-H520 (H520).

H1703 and H520 were cultured and treated for 72 hours with AZD4547 and onvansertib alone or in combination. The treated cells were then subjected to the CellTiter-Glo® cell viability assay. The results are shown in FIG. 6A-FIG. 6F.

Figure 6A:
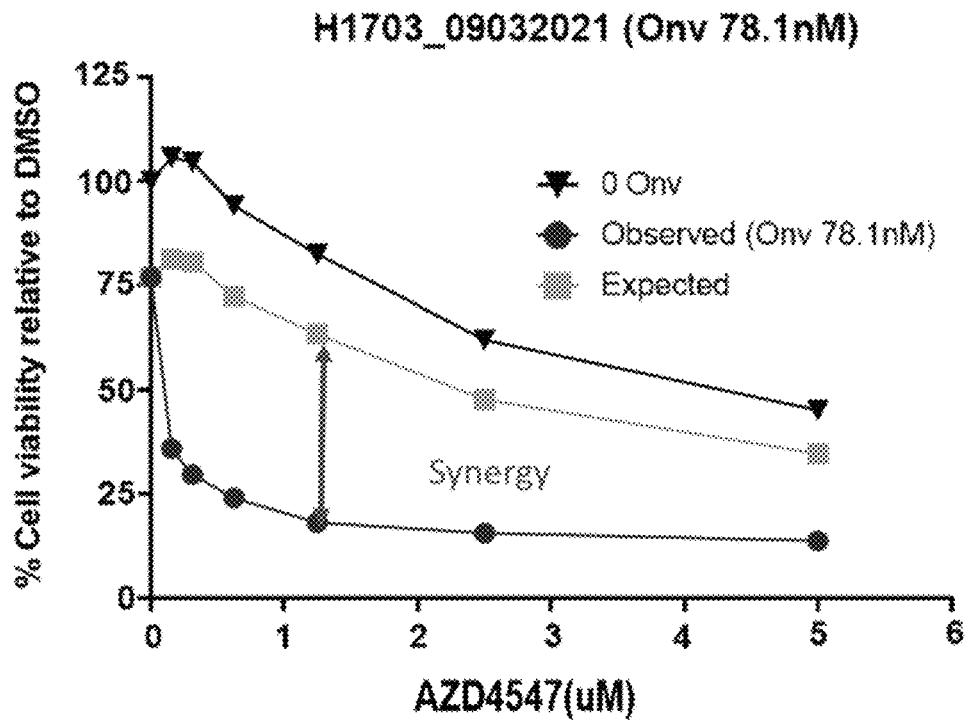
FIG. 6A-FIG. 6F depict non-limiting exemplary embodiments and data showing that onvansertib synergizes with the FGFR inhibitor AZD4547 in two FGFR1-amplified squamous lung cell (SqLC) lines.
Figure 6B:
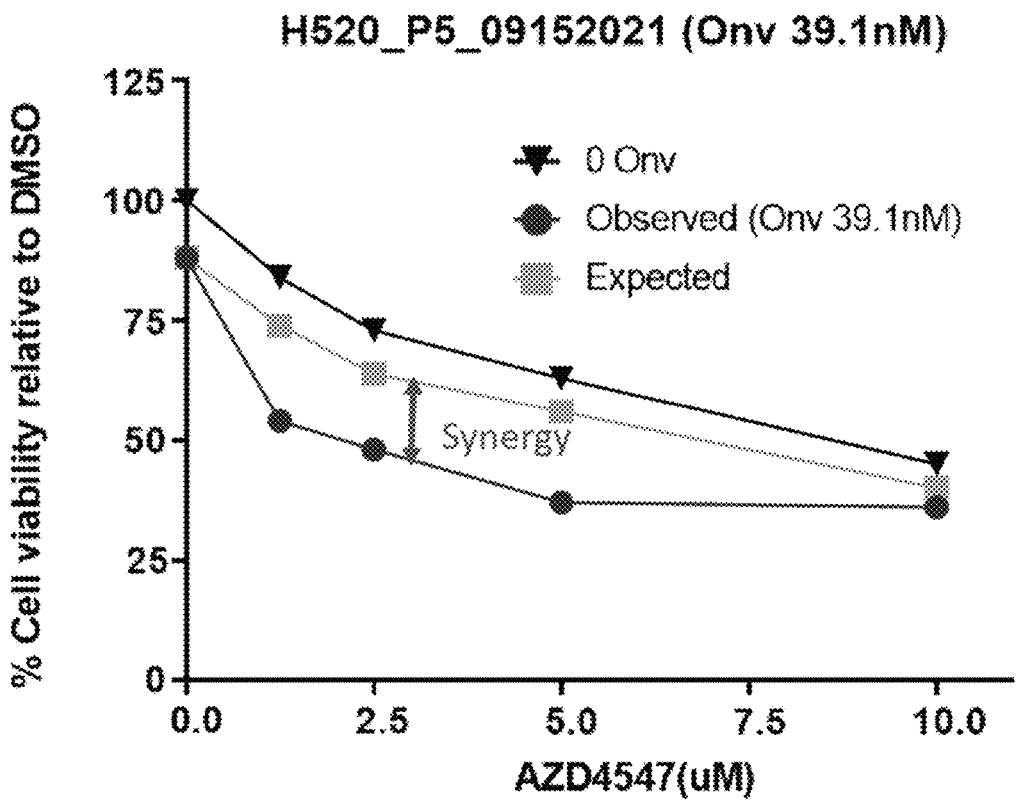
Figure 6C:
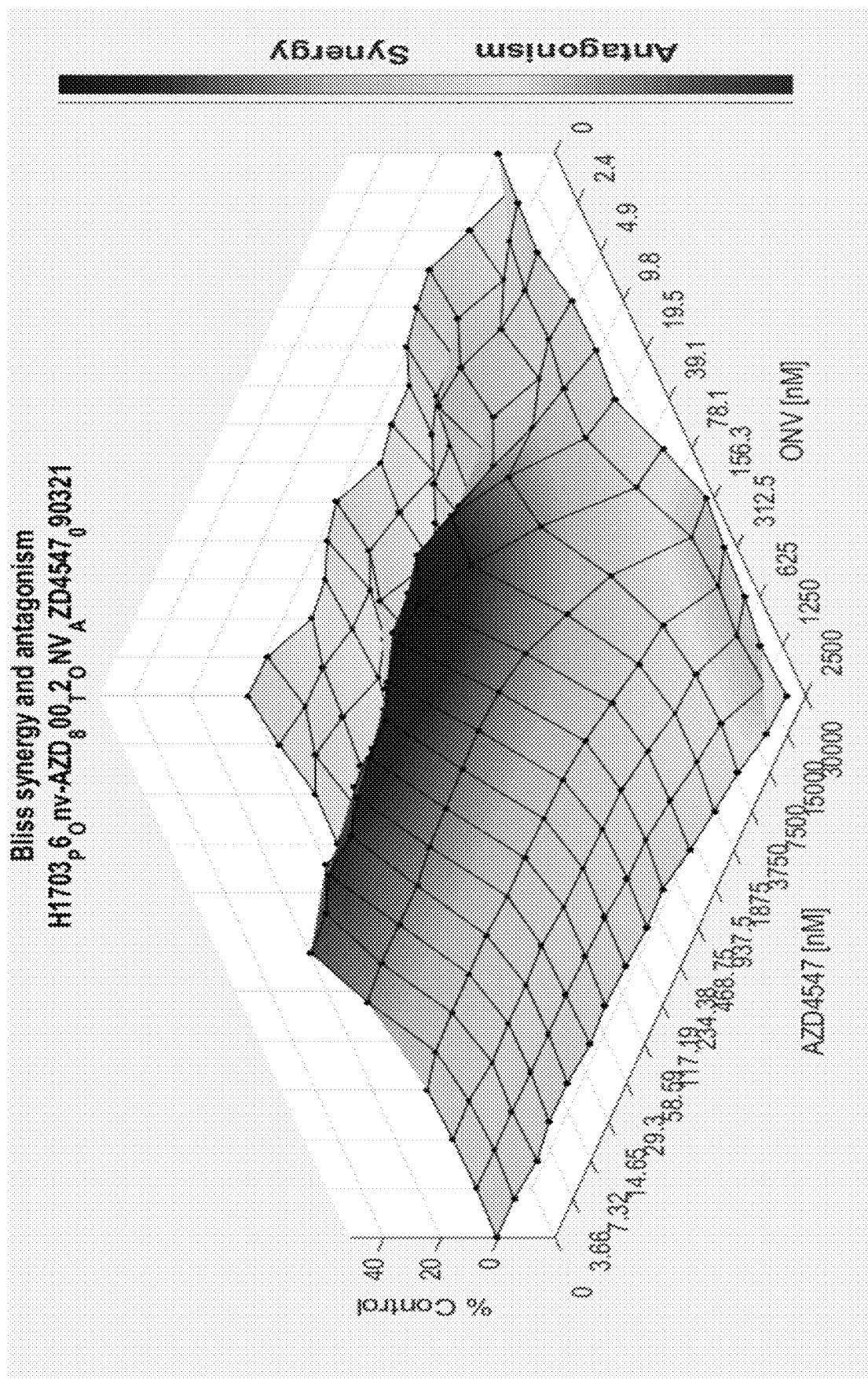

FIG. 6A-FIG. 6B are two plots showing dose-response curves of H1703 and H520 cells treated with AZD4547 alone (triangle) and with AZD4547 and onvansertib (circle) in comparison with the expected effect if there is no synergy (square). The expected effect is the expected effect of AZD4547 and onvansertib acting independently. Onvansertib was provided at a concentration of 78.1 nM and 39.1 nM in H1703 and H520, respectively.

Figure 6D:
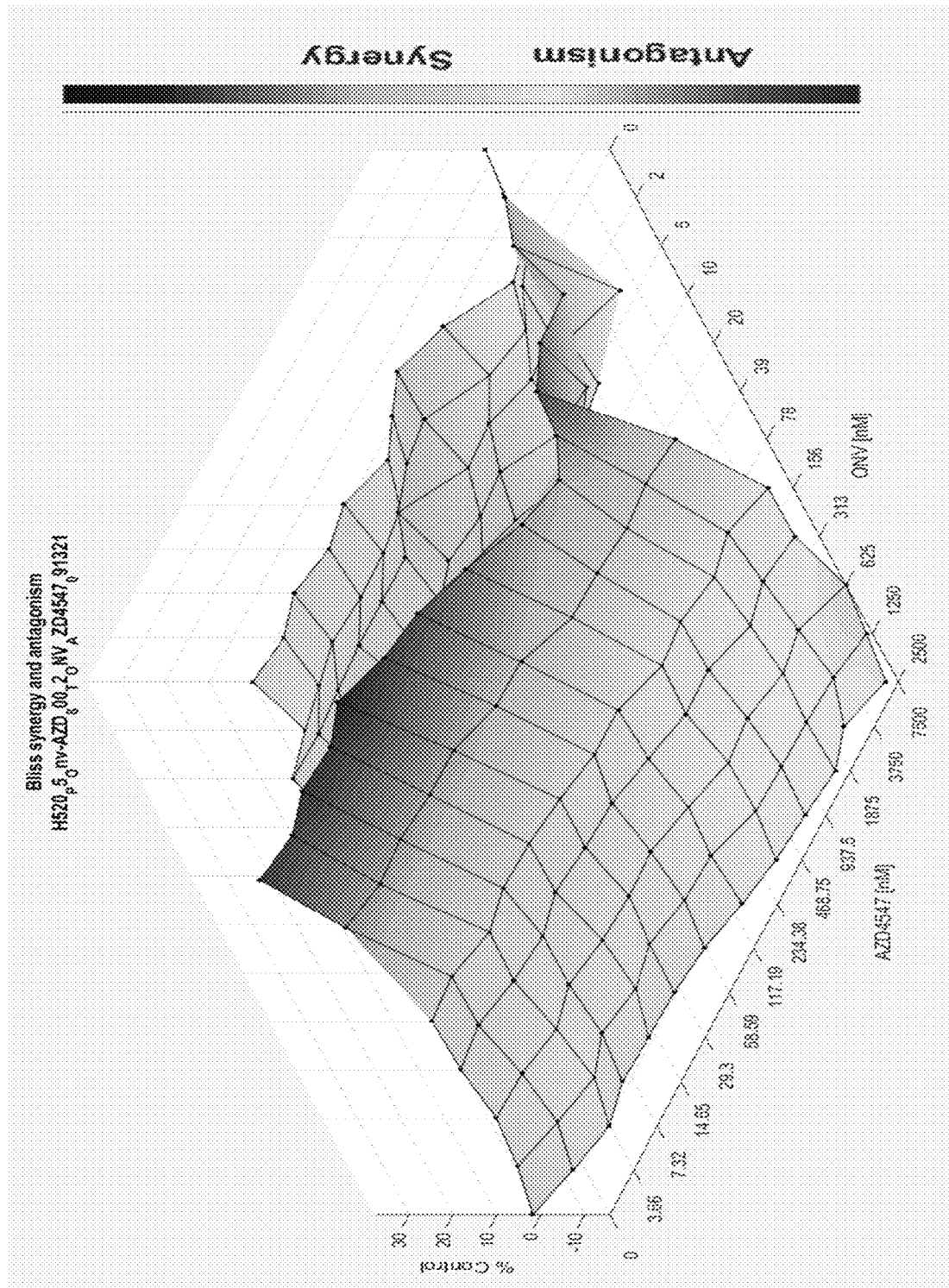
Figure 6E:
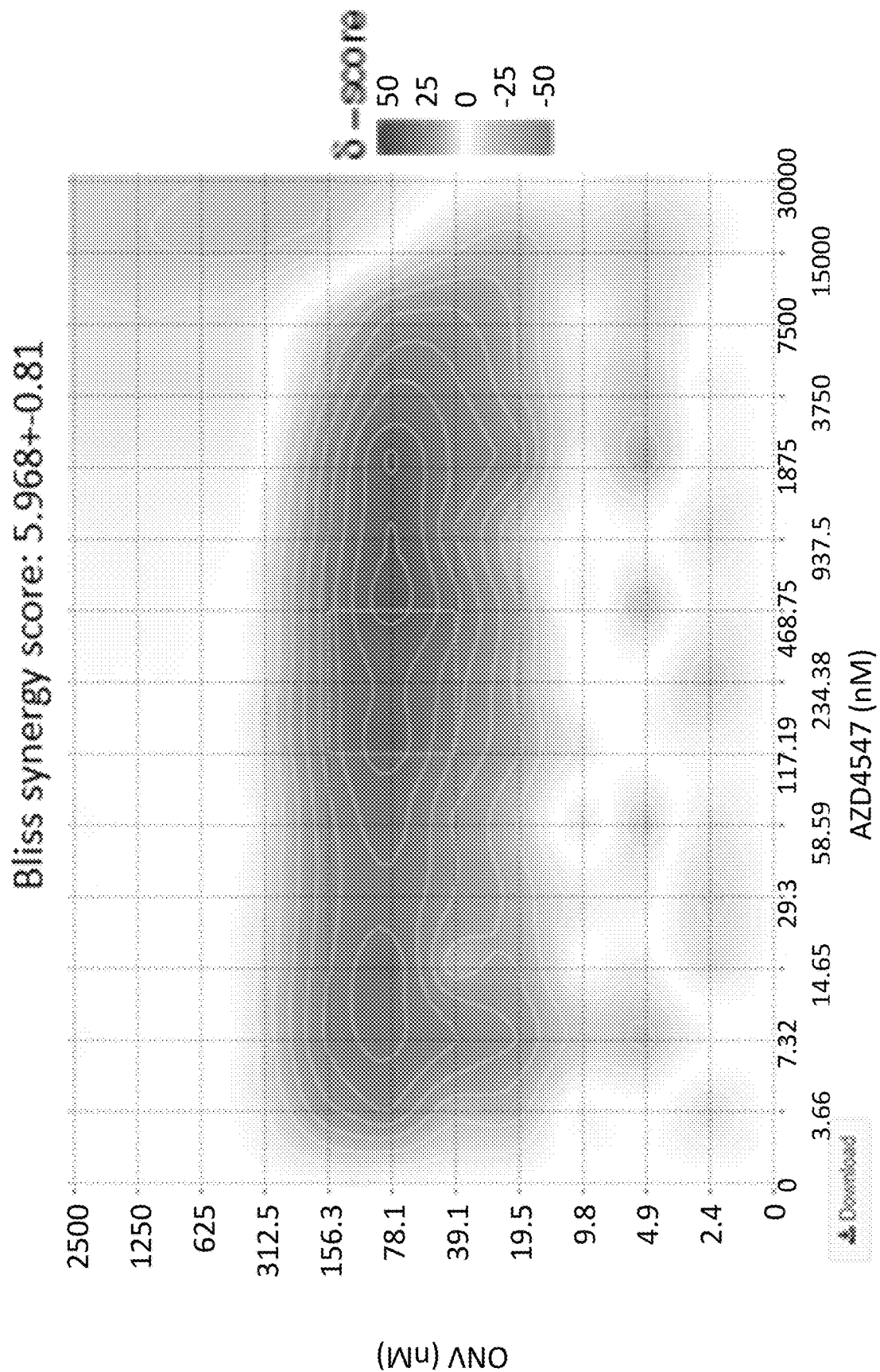
Figure 6F:
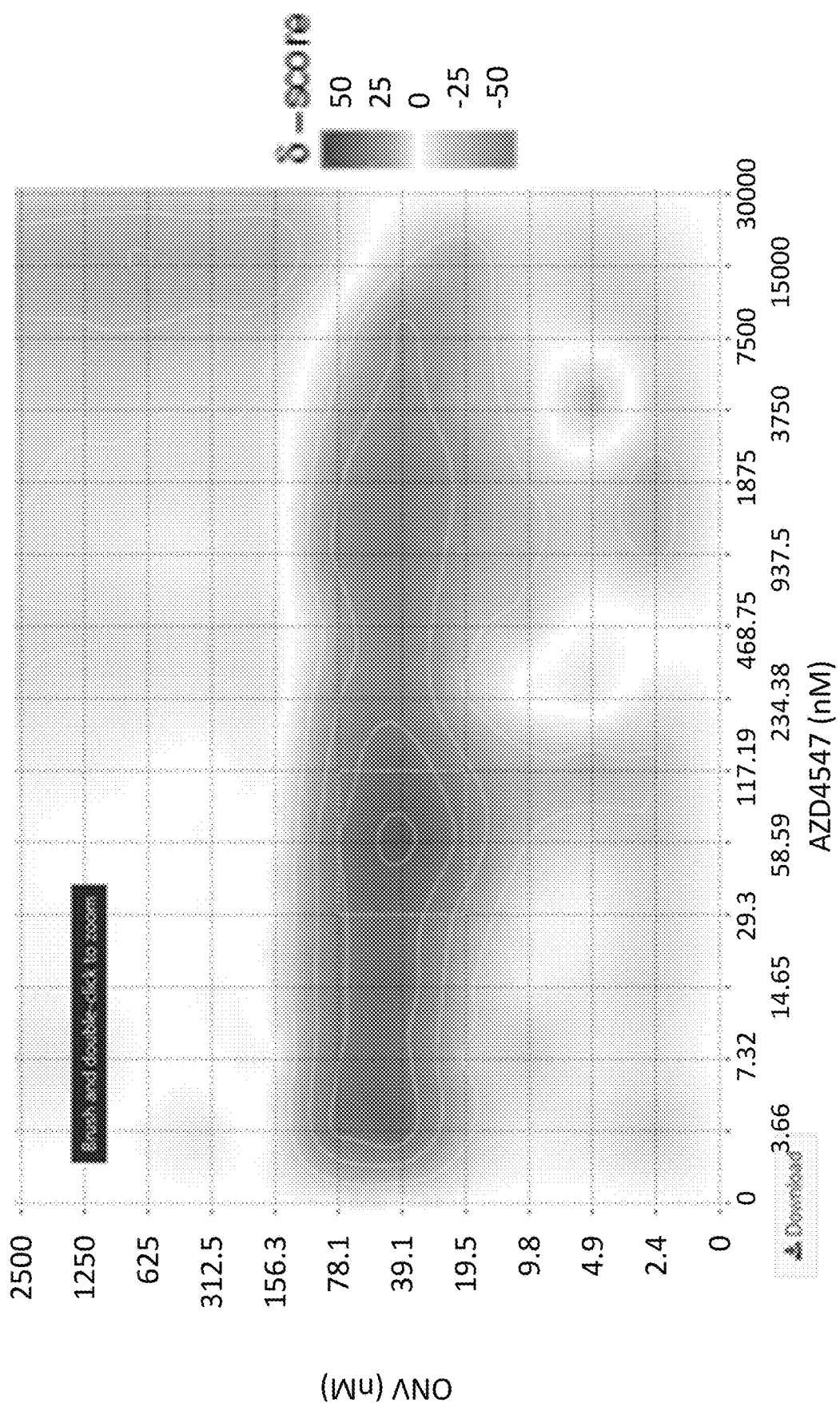

FIG. 6C-FIG. 6F are four plots showing synergistic effects of onvansertib and AZD4547, using the Bliss model. In particular, the synergistic effects were observed at onvansertib concentrations ranging between 19.5 nM and 156.3 nM in the H1703 cell line, with a synergy score of 5.968±0.81 (FIG. 6C and FIG. 6E) and between 20 nM and 156 nM in the H520 cell line, with a synergy score of 3.354±0.66 (FIG. 6D and FIG. 6F).

This example demonstrates that onvansertib synergistically enhances the antiproliferative effect of FGFR inhibitor AZD4547 in FGFR1-amplified lung cancer cells.

Example 2

Antitumor Activity of the Combination of Onvansertib and FGFR Inhibitors

In this example, the synergy between onvansertib and the FGFR inhibitors, including AZD4547, Infigratinib, and Erdafitinib, was evaluated and shown in several cancer cell lines, such as NCI-H1703 (FGFR1-amplified SqLC), NCI-H520 (FGFR1-amplified SqLC), DMS114 (FGFR1-amplified SCLC) and in SNU16 (FGFR2-amplified gastric cell line).

The Bliss independence model was used to evaluate the synergic effects of onvansertib and the FGFR inhibitors. Following drug co-treatment, the observed cell viability is compared to the results expected from simple drug additivity according to the Bliss independence model (BLISS, 1939). Synergistic effects are defined as the difference between the expected and observed responses, which can then be analyzed in terms of greater-than-expected sensitivity to one of the drug components.

NCI-H1703 were cultured and treated with onvansertib and one of 3 different FGFR inhibitors, including AZD4547, Infigratinib and Erdafitinib, alone or in combination. The results are shown in FIG. 7-FIG. 20.

Figure 7:
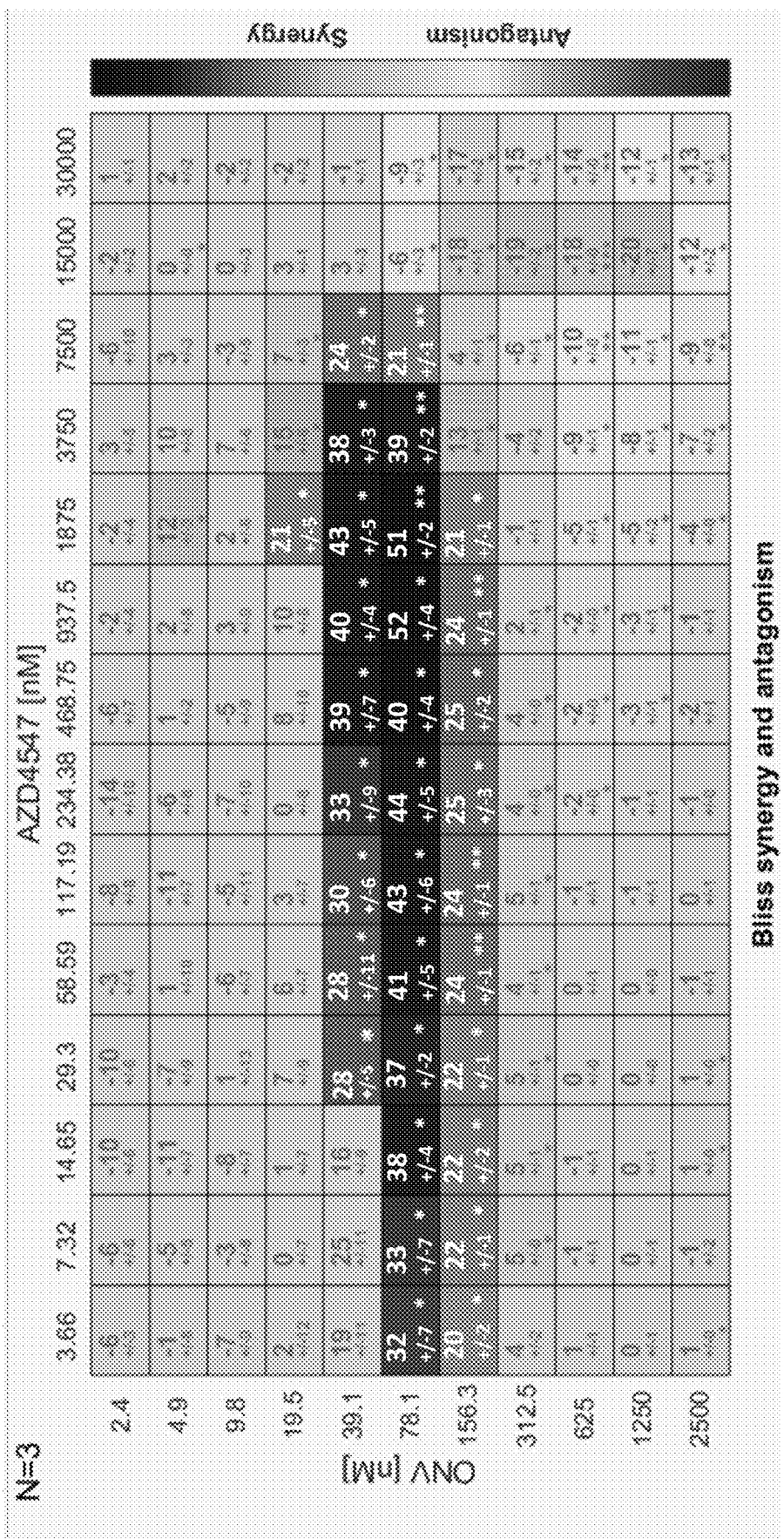
FIG. 7 depicts non-limiting exemplary data related to Bliss synergy combination matrix of onvansertib and AZD4547 in NCI-H1703 cell line in 2D view using the same gradient scale as FIG. 6C. The scores shown in the boxes are synergy scores. Asterisk(s) (*, , or *) indicate that the corresponding score is significant (* $P<5\times10^{-2}$,  $P<10^{-3}$, and * $P<10^{-4}$).
Figure 8:
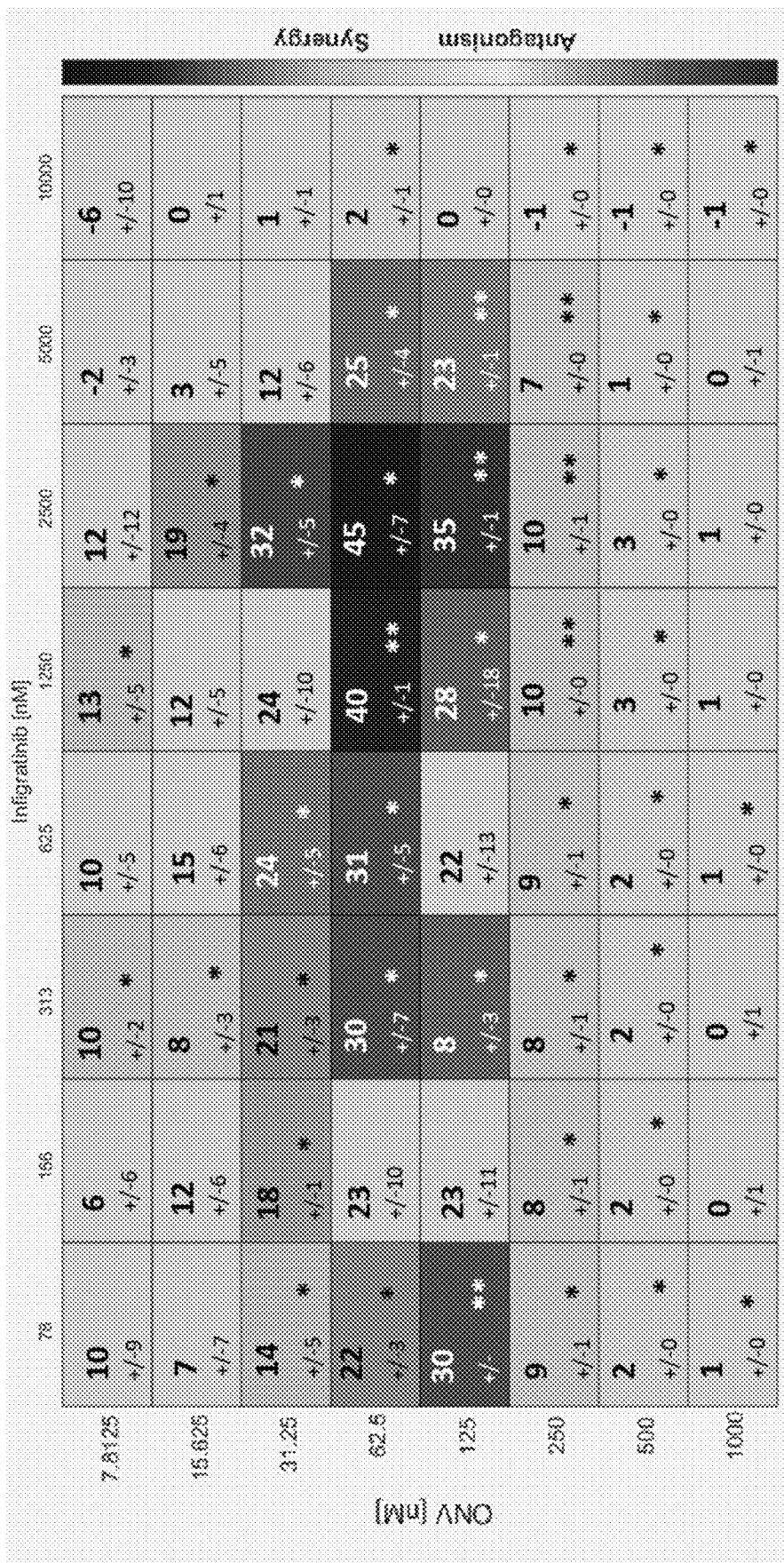
FIG. 8 depicts non-limiting exemplary data related to Bliss synergy combination matrix of onvansertib and FGFR inhibitor Infigratinib (BGJ398) in NCI-H1703 cell line. The scores shown in the boxes are synergy scores. Asterisk(s) (*, , or *) indicate that the corresponding score is significant (* $P<5\times10^{-2}$,  $P<10^{-3}$, and * $P<10^{-4}$).
Figure 9:
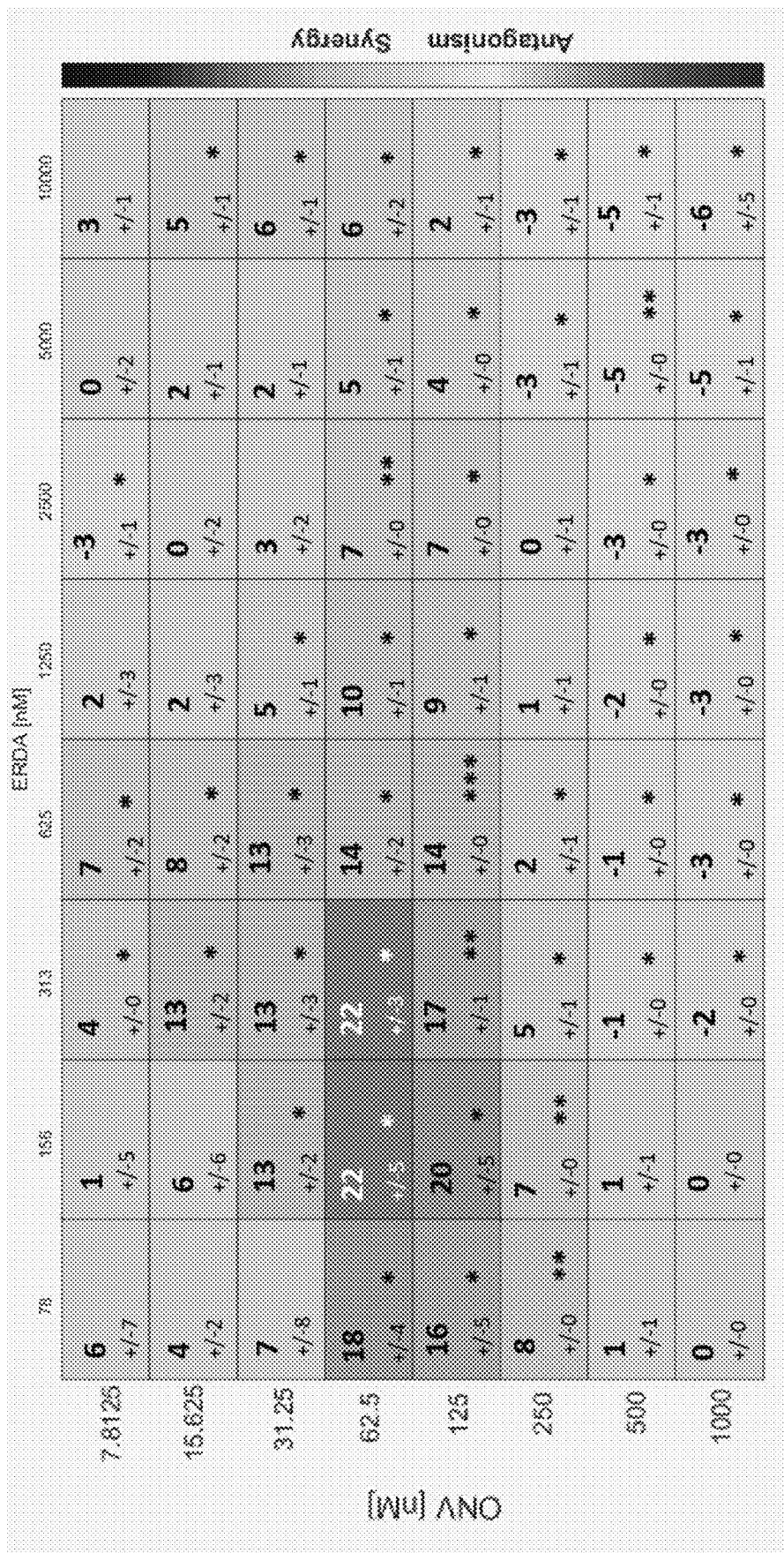
FIG. 9 depicts non-limiting exemplary embodiments and data related to Bliss synergy combination matrix of onvansertib and FGFR inhibitor Erdafitinib (JNJ-42756493) in NCI-H1703 cell line. The scores shown in the boxes are synergy scores. Asterisk(s) (*, , or *) indicate that the corresponding score is significant (* $P<5\times10^{-2}$,  $P<10^{-3}$, and * $P<10^{-4}$).

FIG. 7-FIG. 9 are plots showing synergistic effects of onvansertib and FGFR inhibitors (AZD4547, Infigratinib, and Erdafitinib) in NCI-H1703 cells, using the Bliss model. In particular, the synergistic effects were observed in the H1703 cell line at onvansertib concentrations ranging between 19.5 nM and 156.3 nM with AZD4547 (FIG. 7), between 15.625 nM and 125 nM with Infigratinib (FIG. 8) and between 31.25 nM and 125 nM with Erdafitinib (FIG. 9).

Figure 10:
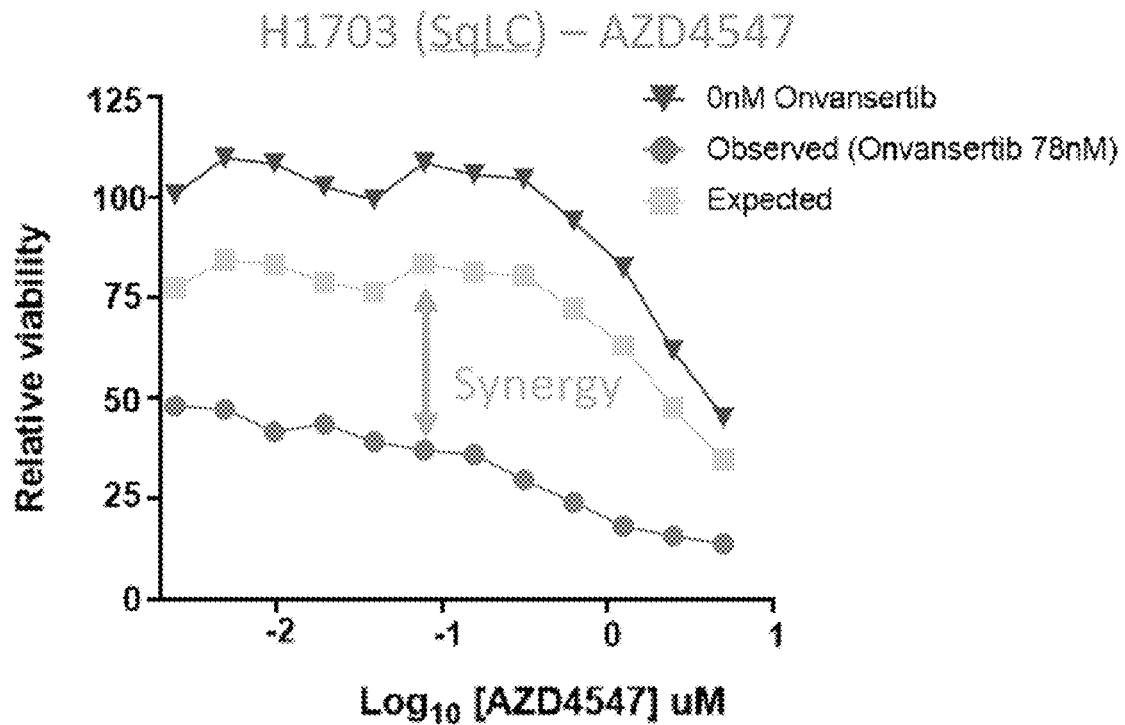
FIG. 10 depicts non-limiting exemplary embodiments and data related to dose-response curves of NCI-H1703 cell line when treated with AZD4547 alone or onvansertib in combination with different doses of AZD4547.
Figure 11:
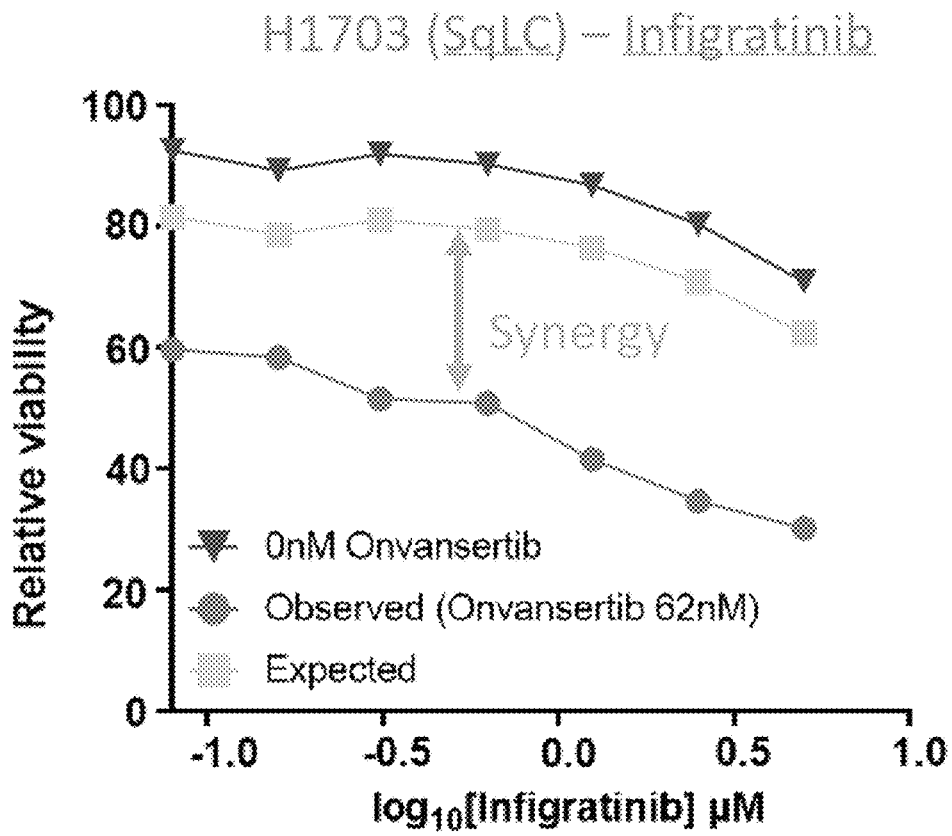
FIG. 11 depicts non-limiting exemplary embodiments and data related to dose-response curves of NCI-H1703 cell line when treated with Infigratinib alone or onvansertib in combination with different doses of Infigratinib.
Figure 12:
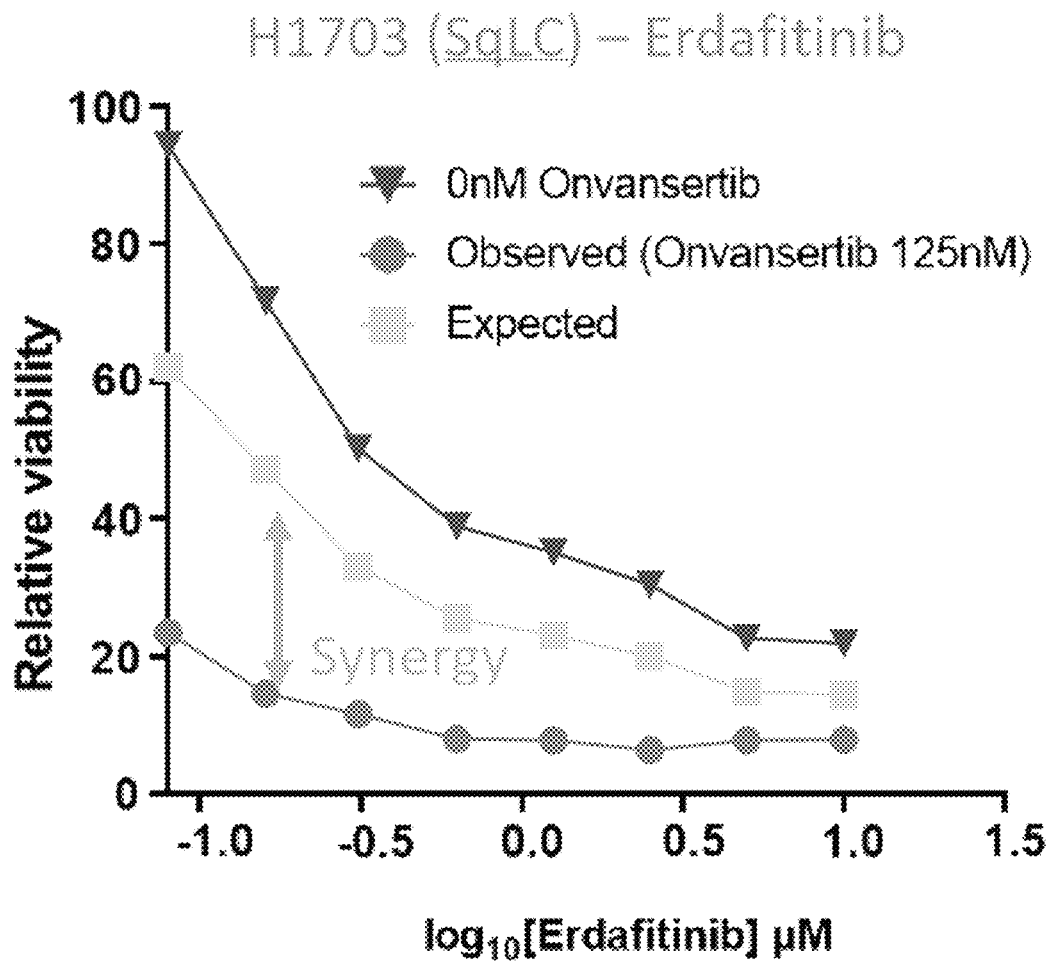
FIG. 12 depicts non-limiting exemplary embodiments and data related to dose-response curves of NCI-H1703 cell line when treated with Erdafitinib alone or onvansertib in combination with different doses of Erdafitinib.

FIG. 10-FIG. 12 are plots showing dose-response curves of NCI-H1703 cells treated with FGFR inhibitors (AZD4547, Infigratinib, or Erdafitinib) alone (triangle) and with the combination of FGFR inhibitors (AZD4547, Infigratinib, or Erdafitinib) and onvansertib (circle) in comparison with the expected effect if there is no synergy (square). The expected effect is the expected effect of FGFR inhibitor and onvansertib acting independently. Onvansertib was provided at a concentration of 78 nM, when combined with AZD4547; 62 nM, when combined with Infigratinib; and 125 nM, when combined with Erdafitinib.

Figure 13:
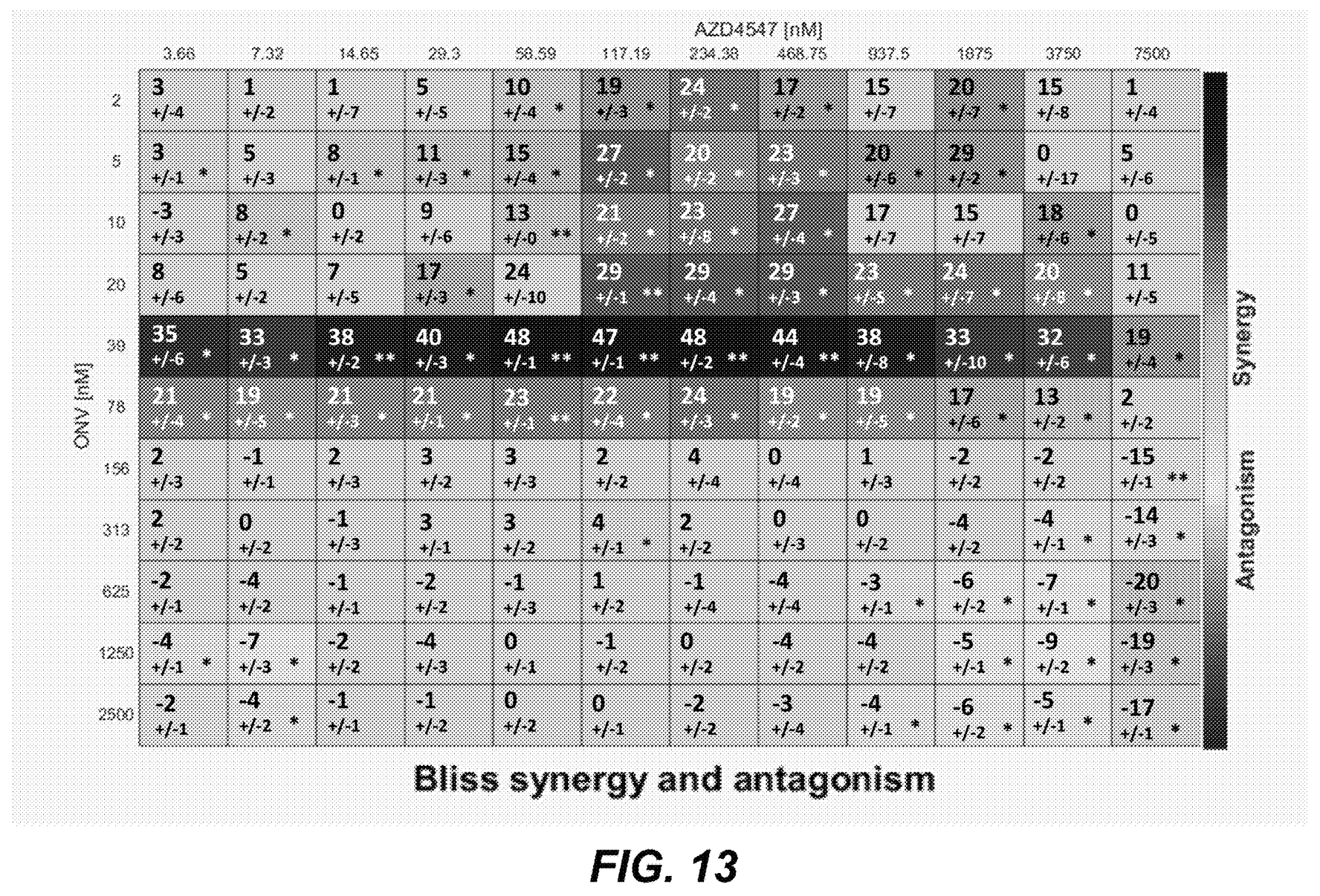

FIG. 13 is a plot showing synergistic effects of onvansertib and AZD4547 in NCI-H520 cells, using the Bliss model. In particular, the synergistic effects were observed in the NCI-H520 cell line at onvansertib concentrations ranging between 2 nM and 78 nM when combined with AZD4547 (FIG. 13).

Figure 16:
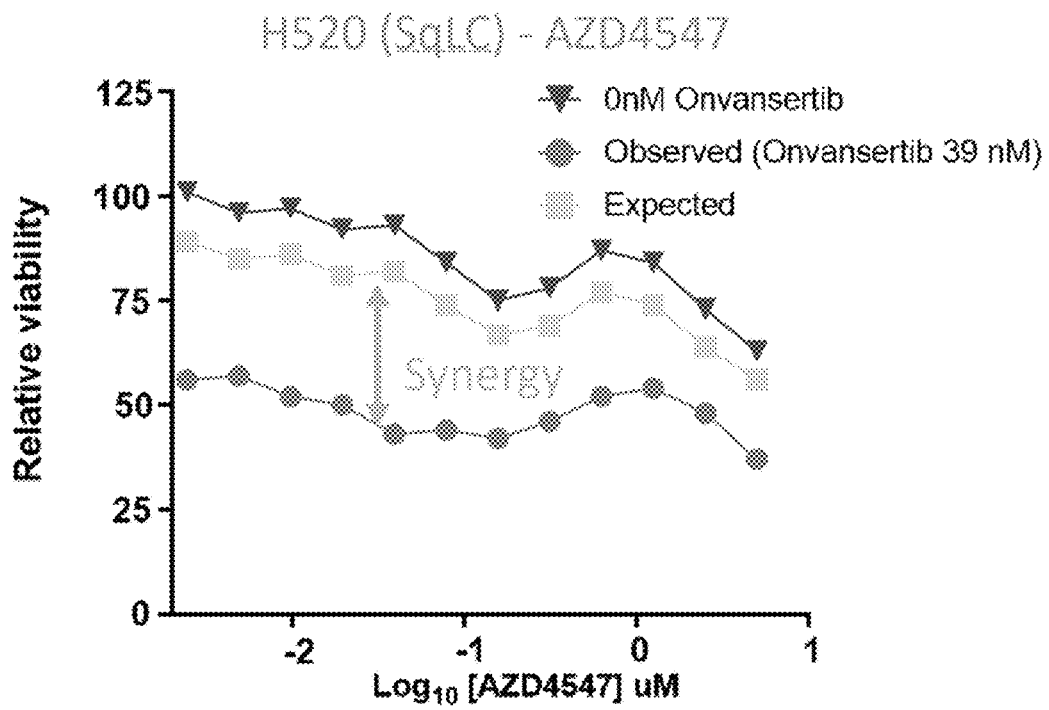
FIG. 16 depicts non-limiting exemplary embodiments and data related to dose-response curves of NCI-H520 cell line when treated with AZD4547 alone or onvansertib in combination with different doses of AZD4547.

FIG. 16 is a plot showing dose-response curves of NCI-H520 cells treated with AZD4547 alone (triangle) and with the combination of AZD4547 and onvansertib (circle) in comparison with the expected effect if there is no synergy (square). The expected effect is the expected effect of AZD4547 and onvansertib acting independently. Onvansertib was provided at a concentration of 39 nM.

Figure 14:
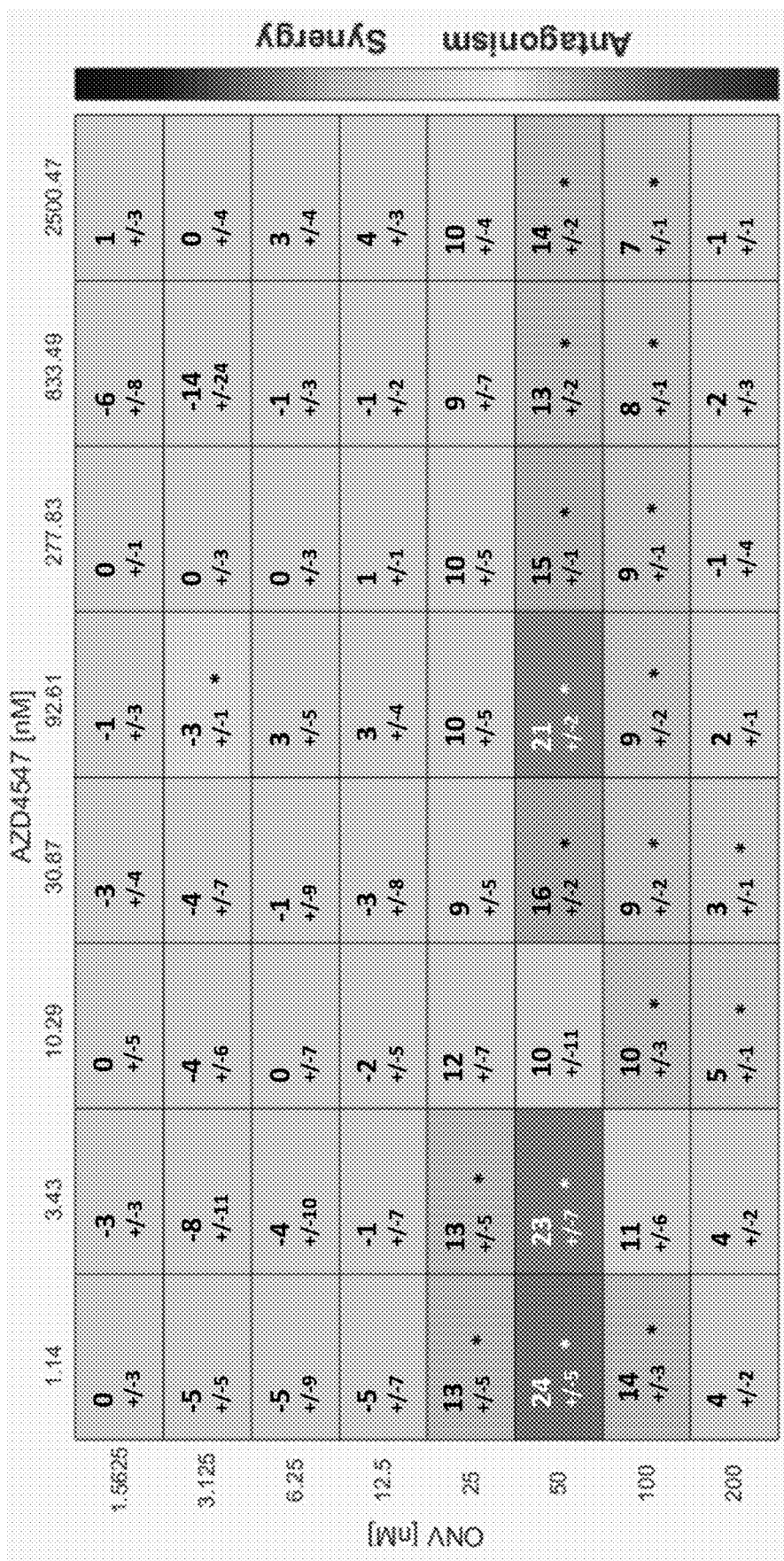
FIG. 14 depicts non-limiting exemplary embodiments and data related to Bliss synergy combination matrix of onvansertib and AZD4547 in the small cell lung cancer DMS114 cell line. The scores shown in the boxes are synergy scores. Asterisk(s) (*, , or *) indicate that the corresponding score is significant (* $P<5\times10^{-2}$,  $P<10^{-3}$, and * $P<10^{-4}$).
Figure 15:
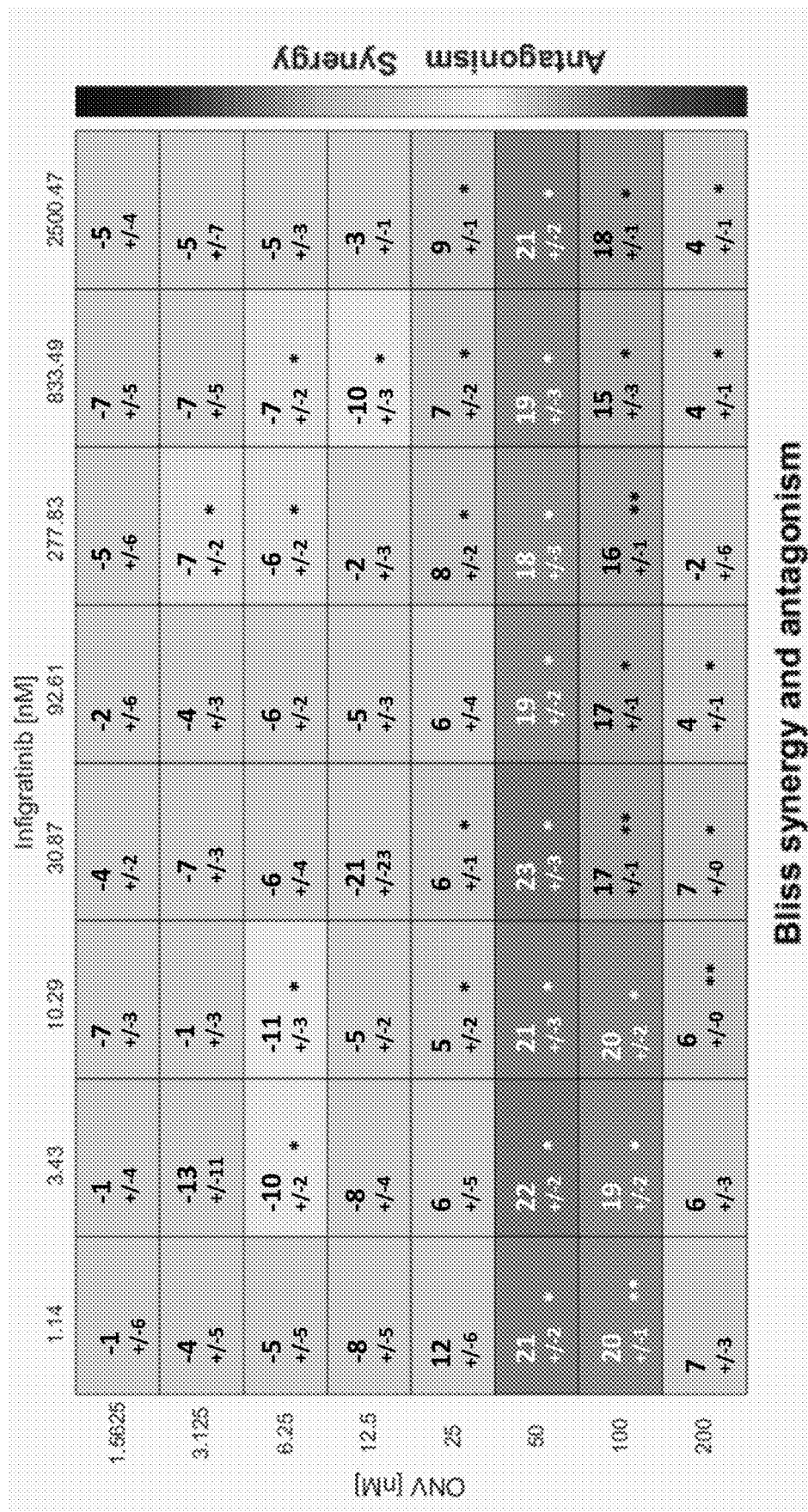
FIG. 15 depicts non-limiting exemplary embodiments and data related to Bliss synergy combination matrix of onvansertib and Infigratinib in DMS114 cell line. The scores shown in the boxes are synergy scores. Asterisk(s) (*, , or *) indicate that the corresponding score is significant (* $P<5\times10^{-2}$,  $P<10^{-3}$, and * $P<10^{-4}$).

FIG. 14-FIG. 15 are plots showing synergistic effects of onvansertib and FGFR inhibitor (AZD4547 or Infigratinib) in DMS114, using the Bliss model. In particular, the synergistic effects were observed in the DMS114 cell line at onvansertib concentrations ranging between 25 nM and 100 nM when combined with AZD4547 (FIG. 14), and between 50 nM and 100 nM with Infigratinib (FIG. 15).

Figure 17:
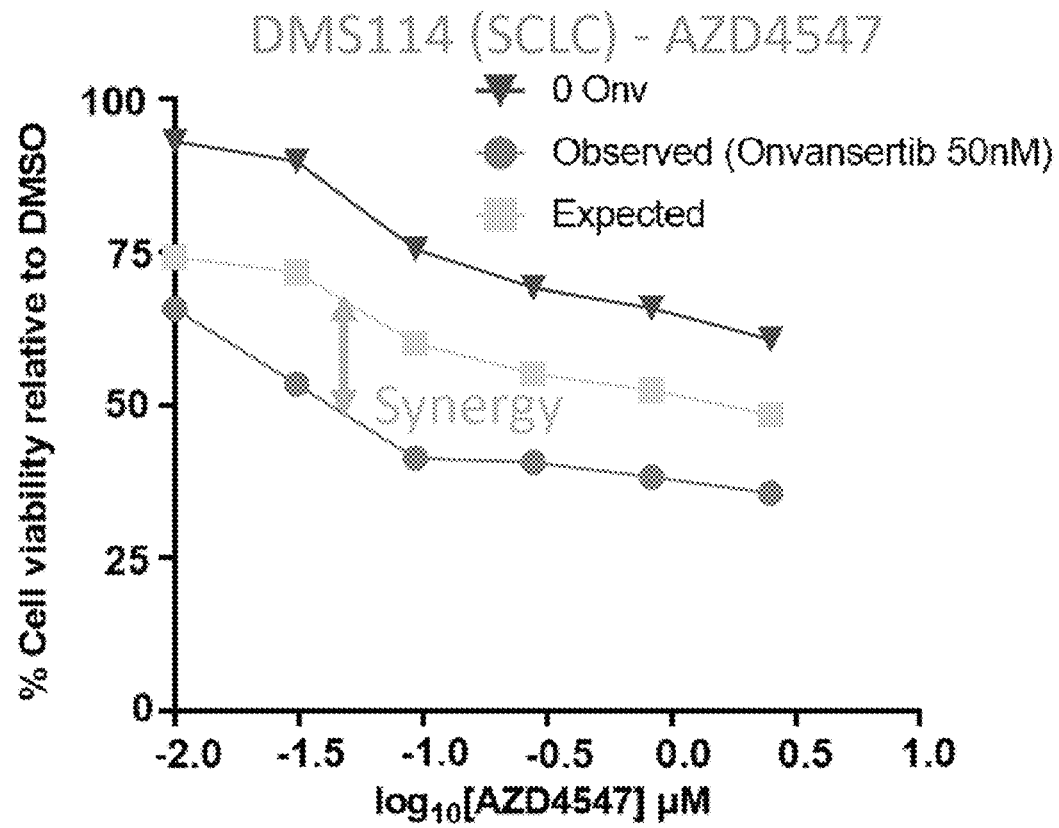
FIG. 17 depicts non-limiting exemplary embodiments and data related to dose-response curves of DMS114 cell line when treated with AZD4547 alone or onvansertib in combination with different doses of AZD4547.
Figure 18:
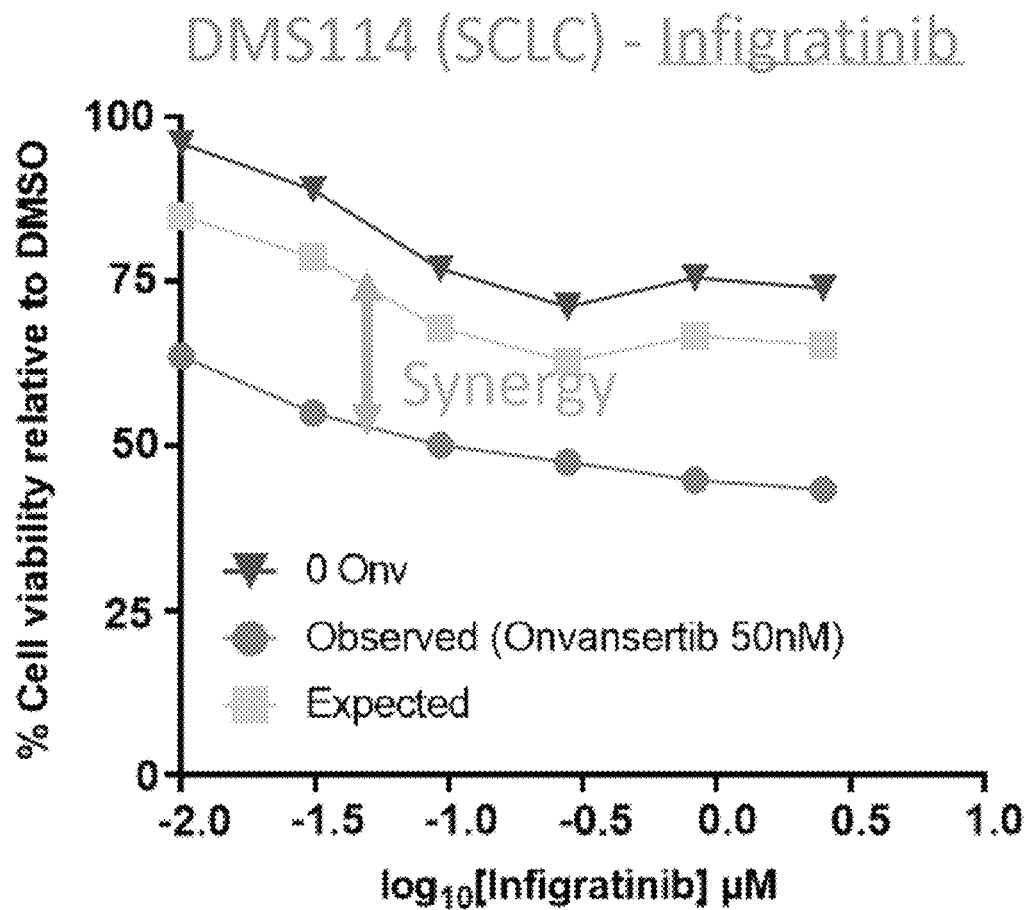
FIG. 18 depicts non-limiting exemplary embodiments and data related to dose-response curves of DMS114 cell line when treated with Infigratinib alone or onvansertib in combination with different doses of Infigratinib.

FIG. 17-FIG. 18 are plots showing dose-response curves of DMS114 cells treated with FGFR inhibitor (AZD4547 or Infigratinib) alone (triangle) and with the combination of FGFR inhibitor (AZD4547 or Infigratinib) and onvansertib (circle) in comparison with the expected effect if there is no synergy (square). The expected effect is the expected effect of FGFR inhibitor and onvansertib acting independently. Onvansertib was provided at a concentration of 50 nM, when combined with either AZD4547 or Infigratinib.

Figure 19:
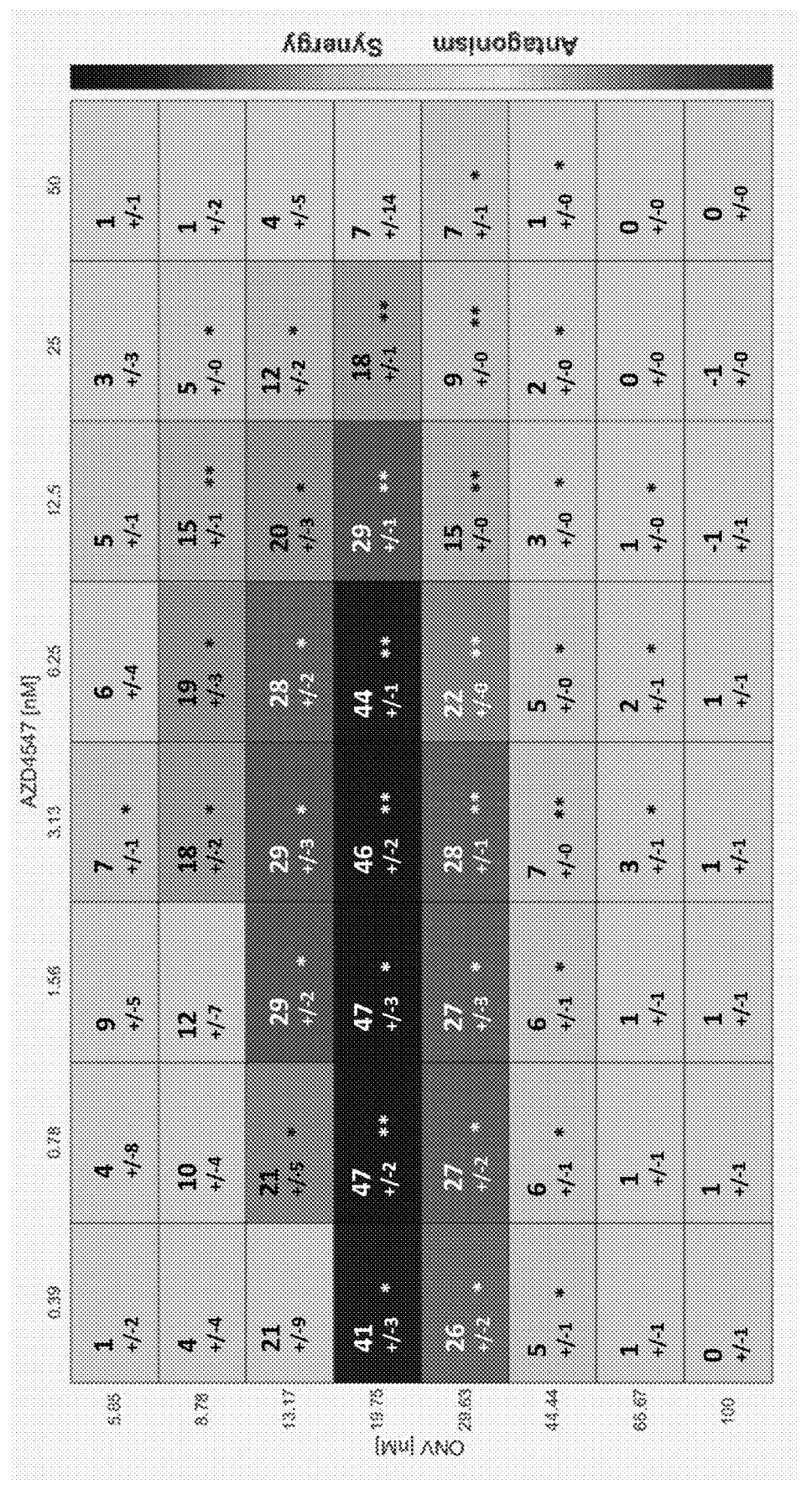
Figure 20:
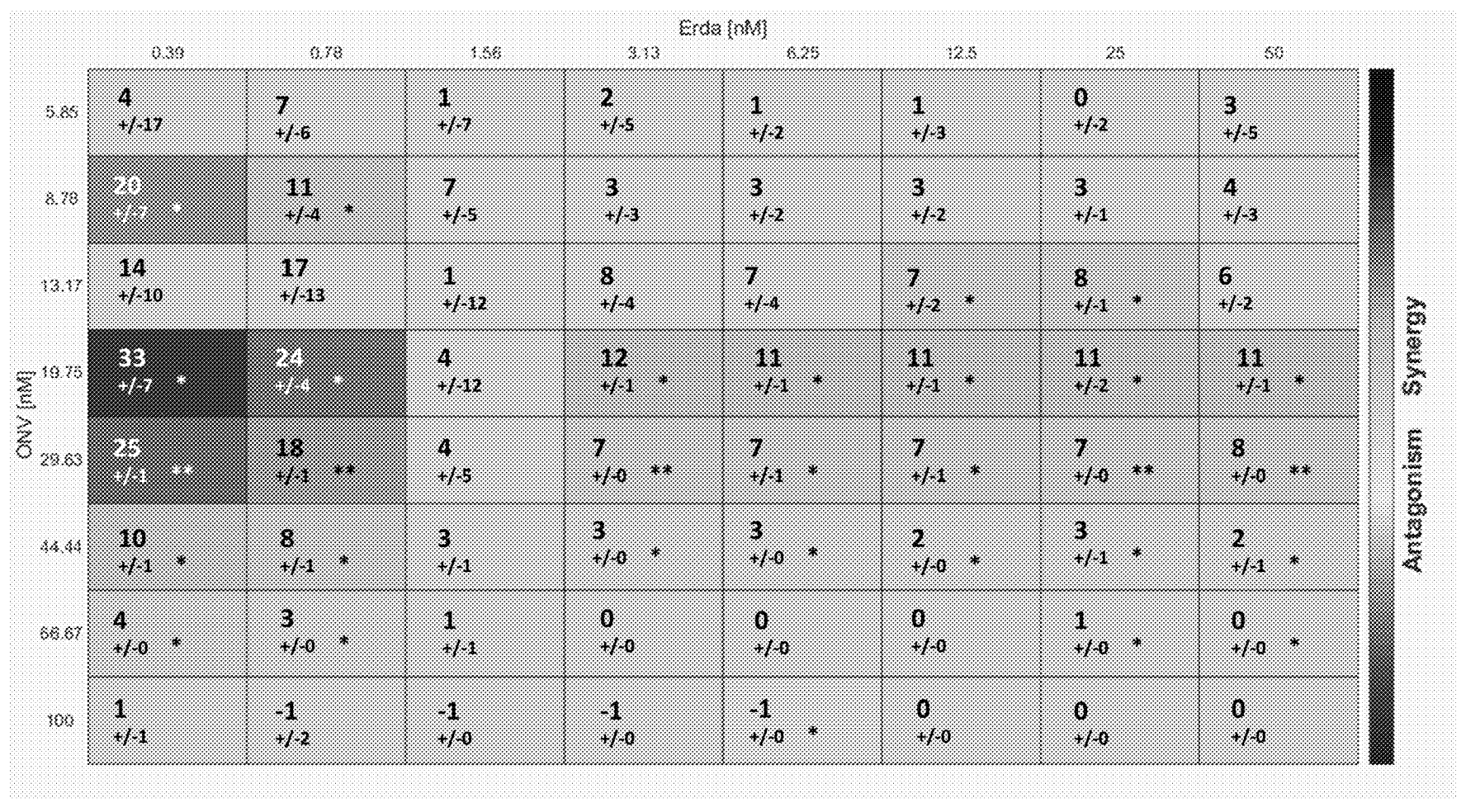

FIG. 19-FIG. 20 are plots showing synergistic effects of onvansertib and FGFR inhibitor (AZD4547 or Erdafitinib) in SNU16 cells, using the Bliss model. In particular, the synergistic effects were observed in the SNU16 cell line at onvansertib concentrations ranging between 8.78 nM and 29.63 nM when combined with AZD4547 (FIG. 19), and between 19.75 nM and 29.63 nM with Erdafitinib (FIG. 20).

Figure 21:
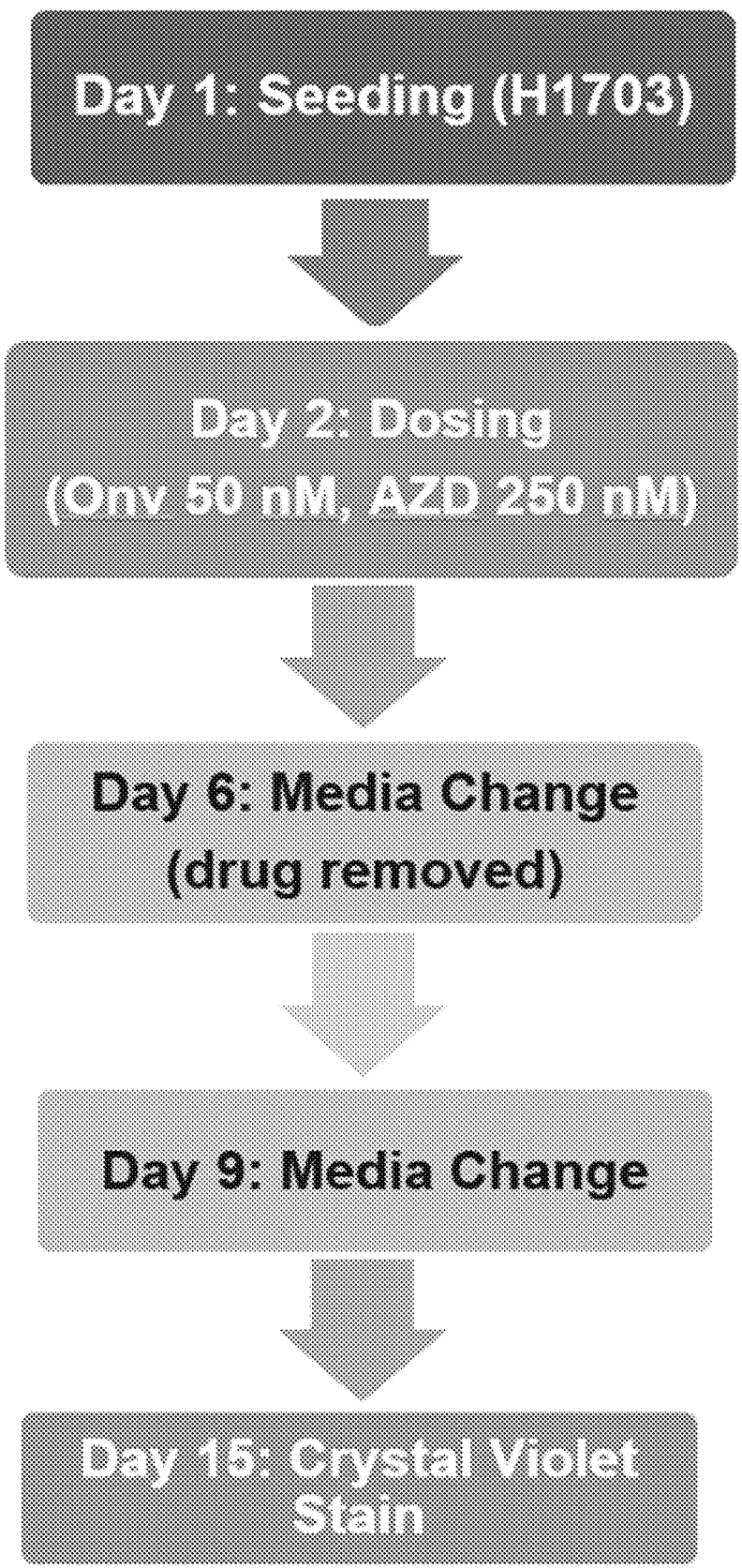
FIG. 21 depicts non-limiting exemplary embodiments and data related to steps of determining colony forming capacity of NCI-H1703 cell lines treated with the combination of onvansertib and AZD4547.
Figure 22:
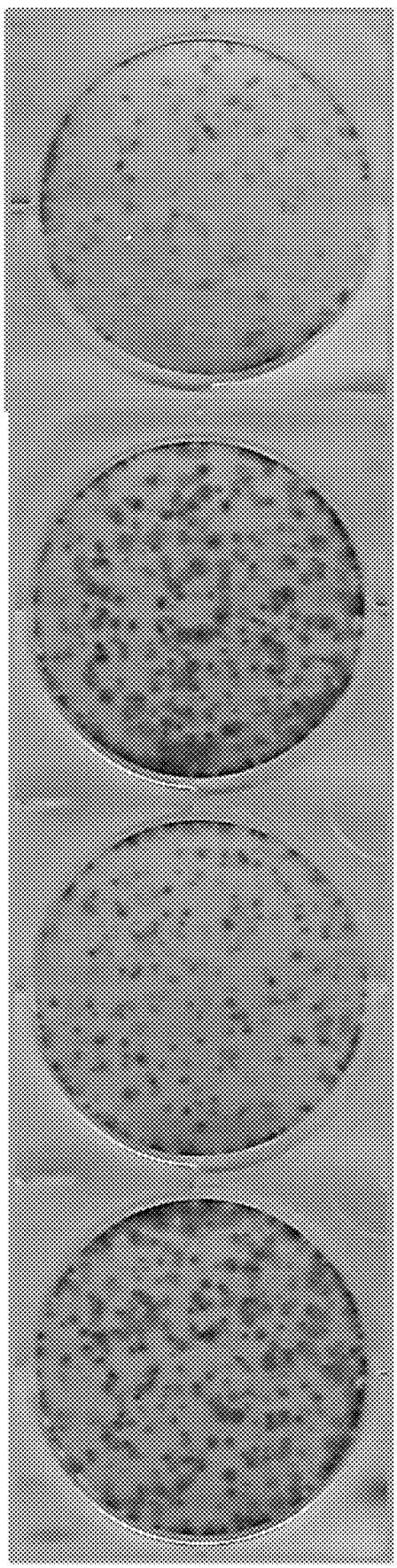
FIG. 22 depicts non-limiting exemplary embodiments and data related to colonies formed by NCI-H1703 cells treated with the combination of onvansertib and AZD4547 and controls (DMSO or single treatment with onvansertib or AZD4547).
Figure 22:
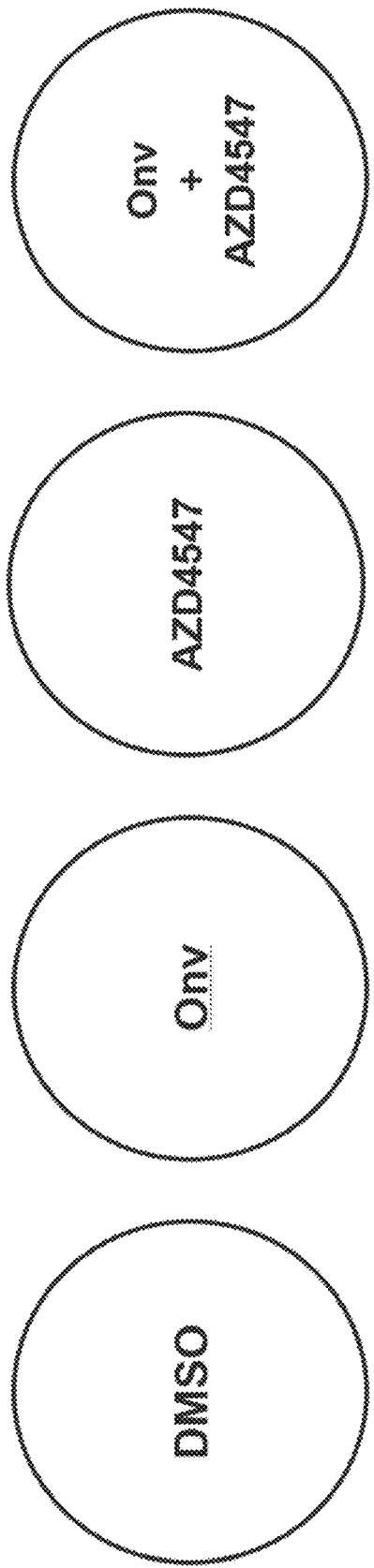
Figure 23:
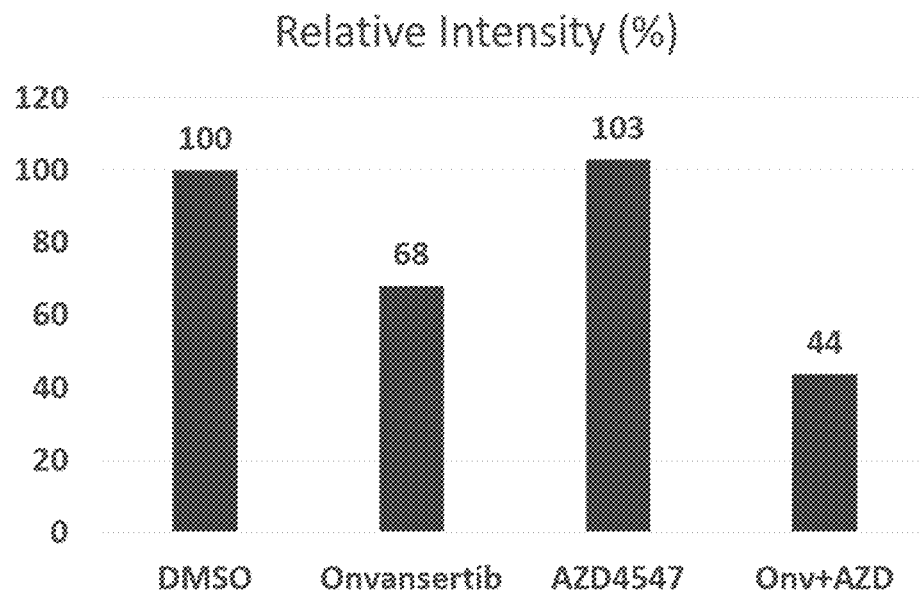
FIG. 23 depicts non-limiting exemplary embodiments and data related to the quantification of colonies formed by NCI-H1703 cells treated with the combination of onvansertib and AZD4547, compared to controls (DMSO or single treatment with onvansertib or AZD4547), as indicated by the relative intensity of crystal violet staining.

In vitro mechanistic studies were also conducted, showing that the combined treatment with onvansertib and AZD4547 decreased colony forming capacity of NCI-H1703 cells, compared to DMSO and single agent treatments. To determine the colony forming capacity, NCI-H1703 cells were cultured for 1 day, followed by treatment with 50 nM of onvansertib and 250 nM AZD4547. NCI-H1703 cells treated with DMSO or single agent (either 50 nM of onvansertib or 250 nM AZD4547) were set up as controls. The culture media was changed 4 days after the treatment to remove the onvansertib and/or AZD4547. The culture media was changed again after 3 days. After culturing for another 6 days, the NCI-H1703 cells were stained with crystal violet. The workflow of determining colony forming capacity is illustrated in FIG. 21. FIG. 22 shows the colonies formed by NCI-H1703 cells treated with different agents. Single treatment with onvansertib (50 nM) reduced the colony-forming capacity of NCI-H1703 cells, compared to NCI-H1703 cells treated with DMSO and AZD4547 (250 nM) alone. Combined treatment with onvansertib (50 nM) and AZD4547 (250 nM) further reduced the colony-forming capacity of NCI-H1703 cells, compared to NCI-H1703 cells treated with onvansertib alone. The colonies formed by NCI-H1703 cells shown in FIG. 22 were quantified as indicated by percentage relative intensity (FIG. 23).

Figure 24:
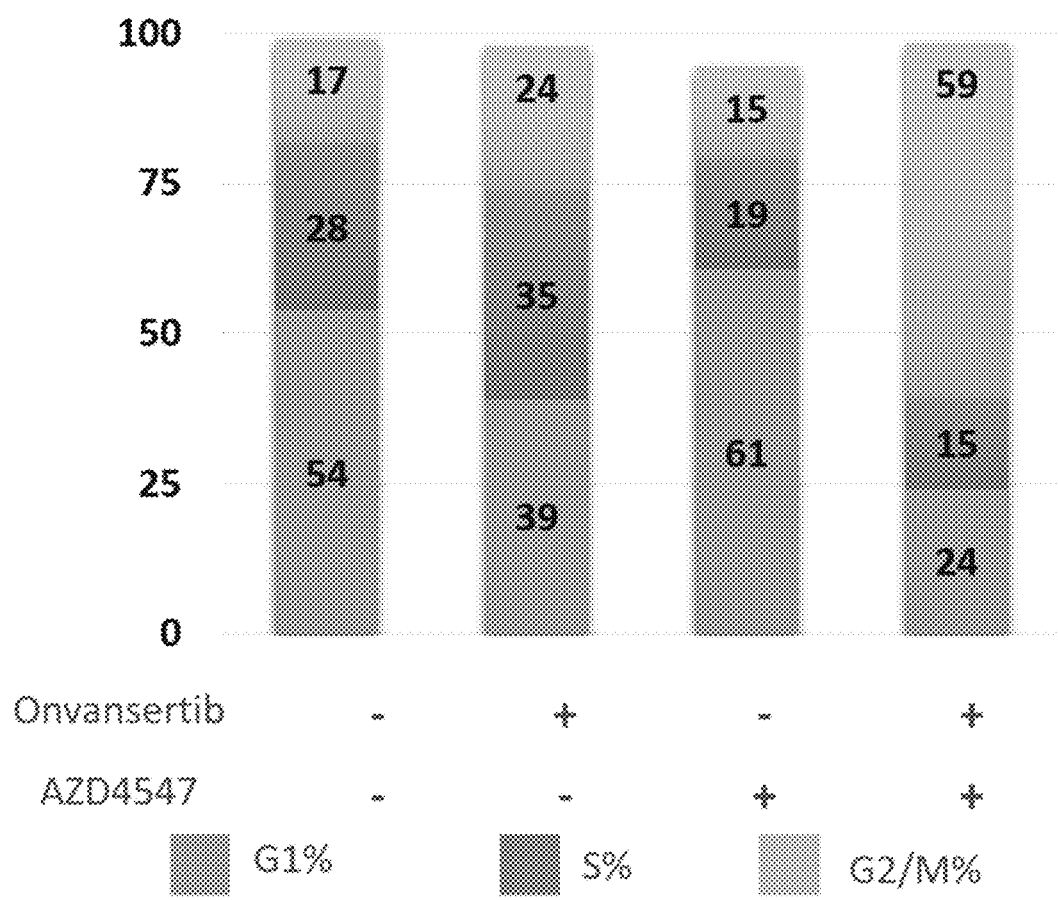
FIG. 24 depicts non-limiting exemplary embodiments and data related to cell cycle analysis of NCI-H1703 cells treated for 48 h (combination of onvansertib and AZD4547, single agents or DMSO), showing that the combination of onvansertib and AZD4547 increases G2 phase and/or mitotic arrest.
Figure 25:
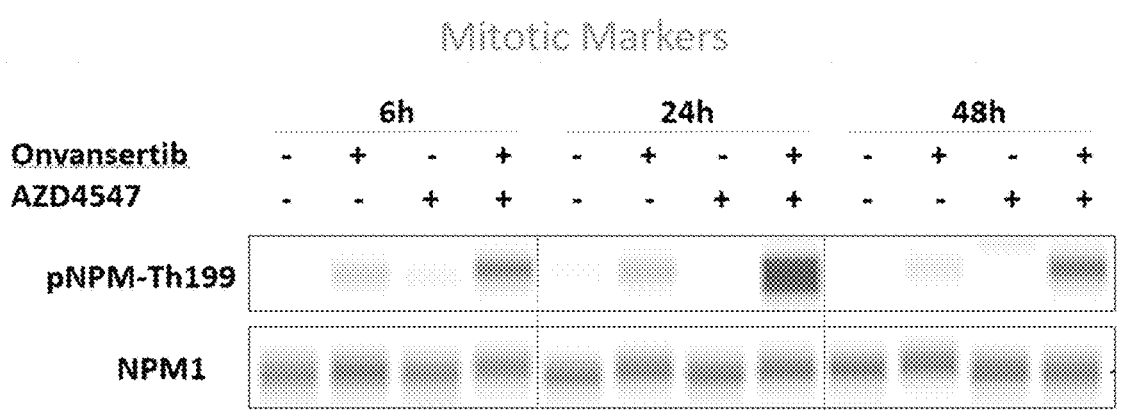
FIG. 25 depicts non-limiting exemplary embodiments and data related to the amount of mitotic marker pNPM-Th199 at different time points after treatments.
Figure 26:
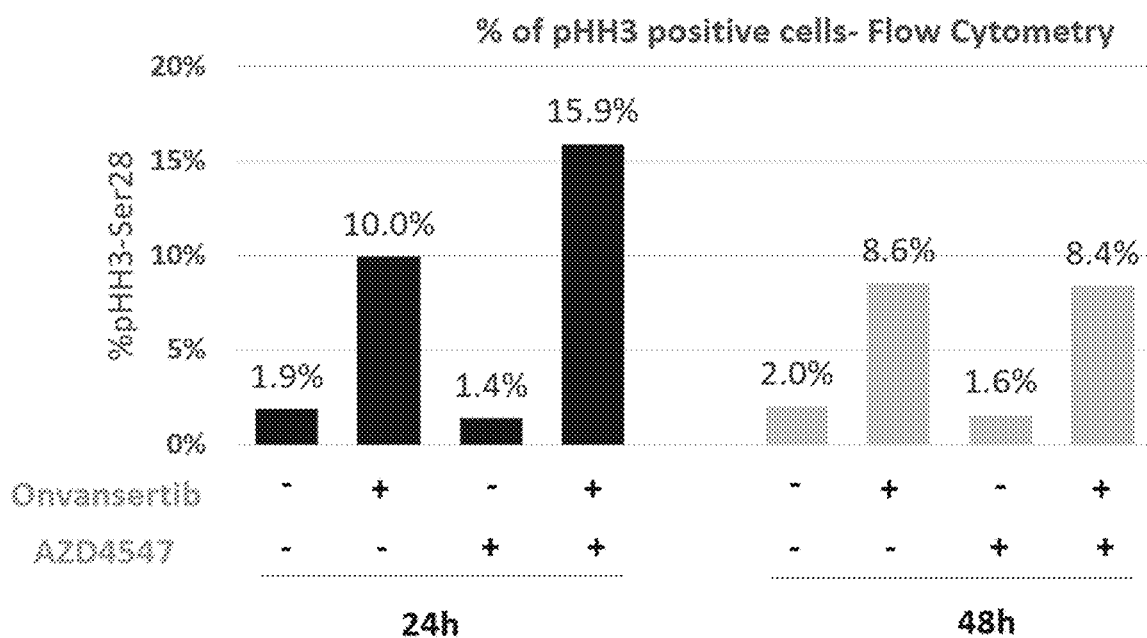
FIG. 26 depicts non-limiting exemplary embodiments and data related to the percentage of phosphorylated histone H3 (pHH3) positive cells 24 hrs and 48 hrs after treatments (single treatment with onvansertib or AZD4547 or combined treatment with onvansertib or AZD4547), compared to cells treated with DMSO and showing that onvansertib single agent and in combination with AZD4547 increase mitotic arrest.

Furthermore, the combination of onvansertib and AZD4547 induced increased G2 and/or mitotic arrest compared to vehicle (DMSO) and single agents. To conduct cell cycle analysis, NCI-H1703 cells were treated with DMSO, 50 nM onvansertib, 2.5 μM AZD4547 or both for 48 hrs. FIG. 24 shows the relative number of cells in each cycle stage, 48 hrs after treatment. Treatment with onvansertib alone increased the % of cells in G2 and/or mitotic stages, compared to vehicle and treatment with AZD4547 alone. Combined treatment with onvansertib and AZD4547 further increased the % of cells in G2 and mitotic stages, compared to single treatment with onvansertib. To confirm the effect of the combination of onvansertib and AZD4547, the phosphorylation of NPM at Threonine 199 was determined at 6 hrs, 24 hrs and 48 hrs after treatments. Increased phosphorylation of NPM was observed at all time points after being treated with onvansertib alone. Phosphorylation of NPM was further increased after being treated with the combination of onvansertib and AZD4547 (FIG. 25). The percentage of pHH3 positive cells was also determined using flow cytometry at 24 h and 48 h. At 24 h, both single treatment with onvansertib alone and combined treatment with onvansertib and AZD4547 increased the percentage of pHH3 positive cells, while a greater percentage of pHH3 positive cells was observed following the combined treatment with onvansertib and AZD4547 (FIG. 26). At 48 h, single treatment with onvansertib alone and combined treatment with onvansertib and AZD4547 increased the percentage of pHH3 positive cells to a similar extent (FIG. 26).

Figure 27:
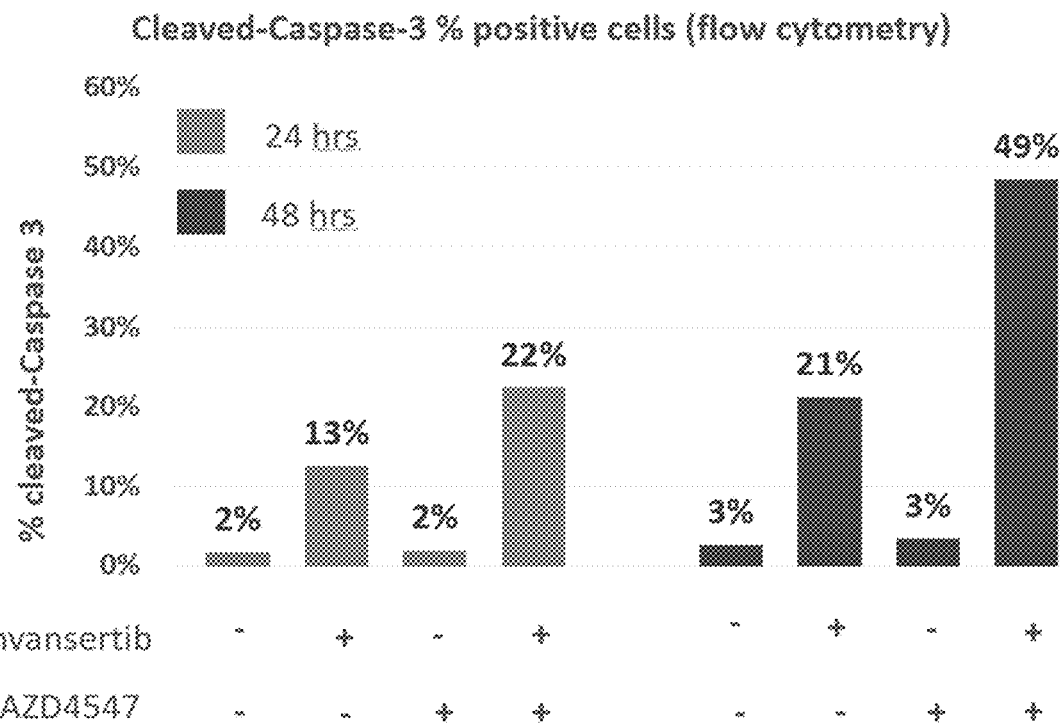
FIG. 27 depicts non-limiting exemplary embodiments and data related to the percentage of cleaved-caspase-3 positive cells 24 h and 48 h after treatments (single treatment with onvansertib or AZD4547 or combined treatment with onvansertib or AZD4547), compared to cells with no treatment and showing that onvansertib single agent and in combination with AZD4547 increase mitotic arrest.
Figure 28:
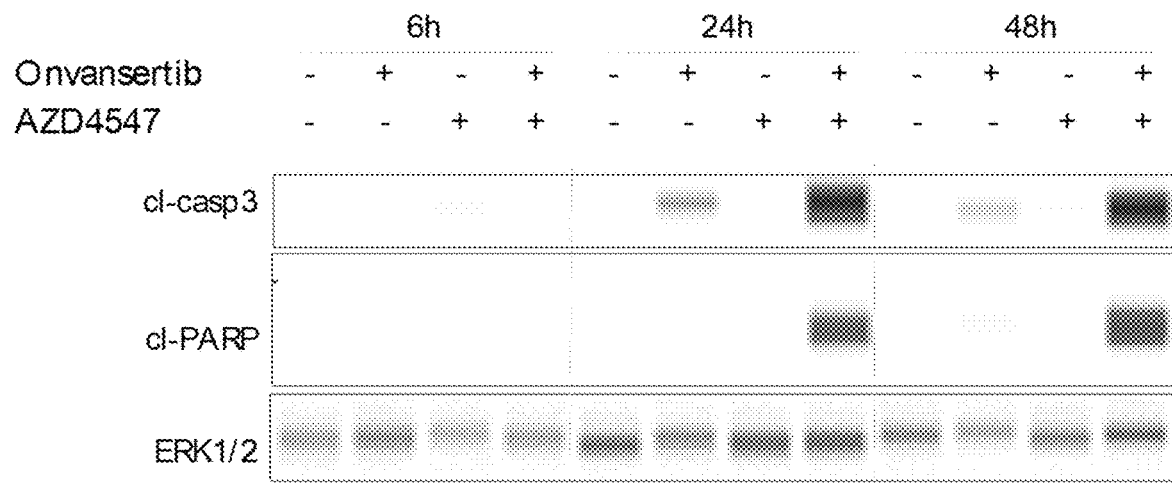
FIG. 28 depicts non-limiting exemplary embodiments and data related to the amounts of apoptotic markers cleaved caspase 3 (cl-casp3) and cleaved Poly (ADP-ribose) polymerase (cl-PARP) at different time points after treatments (single treatment with onvansertib or AZD4547 or combined treatment with onvansertib or AZD4547), compared to cells treated with DMSO and showing that the combination induces increased apoptosis compared to DMSO and single agents.

The combination of onvansertib and AZD4547 also induced increased apoptosis compared to vehicle and single agents in NCI-H1703 cells. To determine the effect of the combination of onvansertib and AZD4547 on apoptosis, the percentage of cleaved-caspase-3 positive cells was determined with flow cytometry, 24 h and 48 h after different treatments. At both 24 h and 48 h after different treatments, single treatment with onvansertib increased the percentage of cleaved-caspase-3 positive cells, compared to vehicle and treatment with AZD4547 alone (FIG. 27). Combined treatment with onvansertib and AZD4547 further increased the percentage of cleaved-caspase-3 positive cells at both time points, compared to treatment with onvansertib alone (FIG. 27). In addition, the amounts of cleaved caspase-3 and cleaved PARP were determined at 6 h, 24 h and 48 h after different treatments using Western Blot. None of the treatments increased the cleaved caspase-3 and cleaved PARP at 6 h (FIG. 28). At both 24 h and 48 h, single treatment with onvansertib increased the cleaved caspase-3, but not cleaved PARP (FIG. 28). Combined treatment with both onvansertib and AZD4547 increased cleaved PARP at 24 h and 48 h, and further increased cleaved caspase-3 compared to single treatment with onvansertib (FIG. 28).

Figure 29:
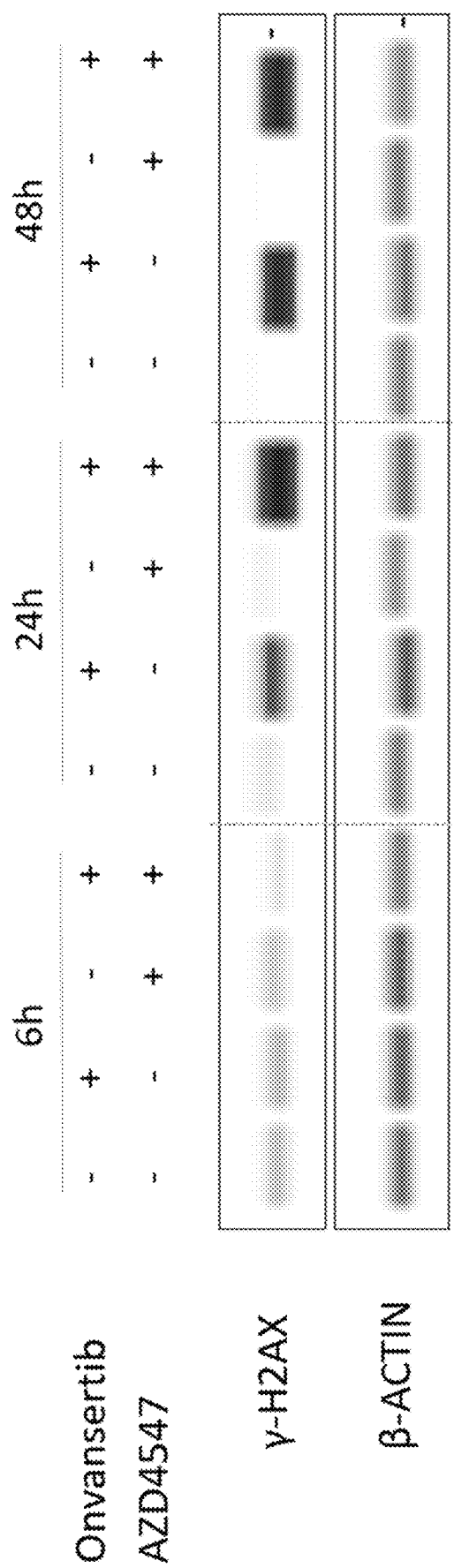
FIG. 29 depicts non-limiting exemplary embodiments and data related to the amount of phosphorylated histone H2AX (γH2AX) at different time points after treatments (single treatment with onvansertib or AZD4547 or combined treatment with onvansertib or AZD4547), compared to cells treated with DMSO and showing that the combination induces increased DNA damage compared to DMSO and single agents.
Figure 30:
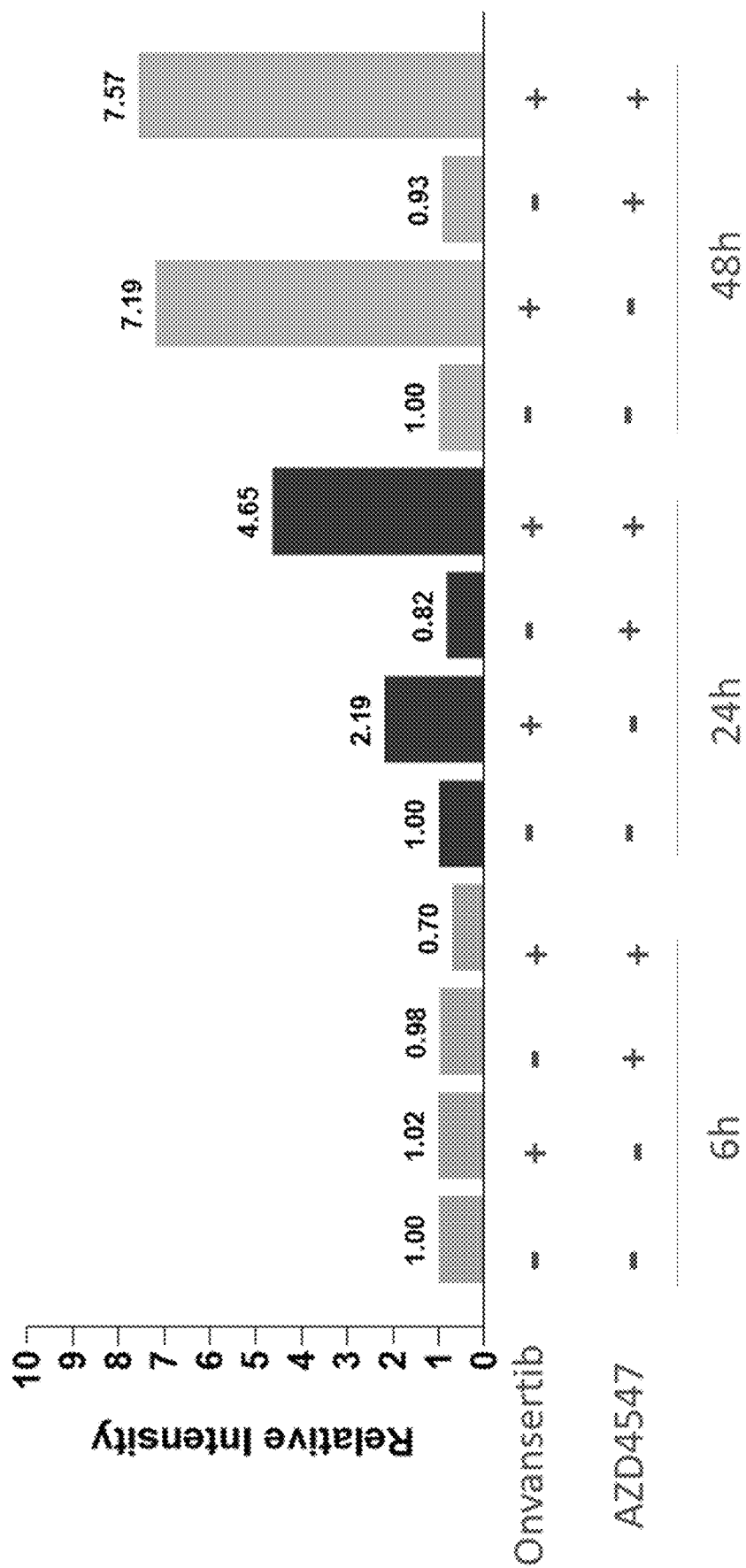
FIG. 30 depicts non-limiting exemplary embodiments and data related to the relative intensity of the γ-H2AX band in FIG. 29 to quantify the increase in DNA damage observed in the combination group compared to DMSO or single agents.
Figure 31:
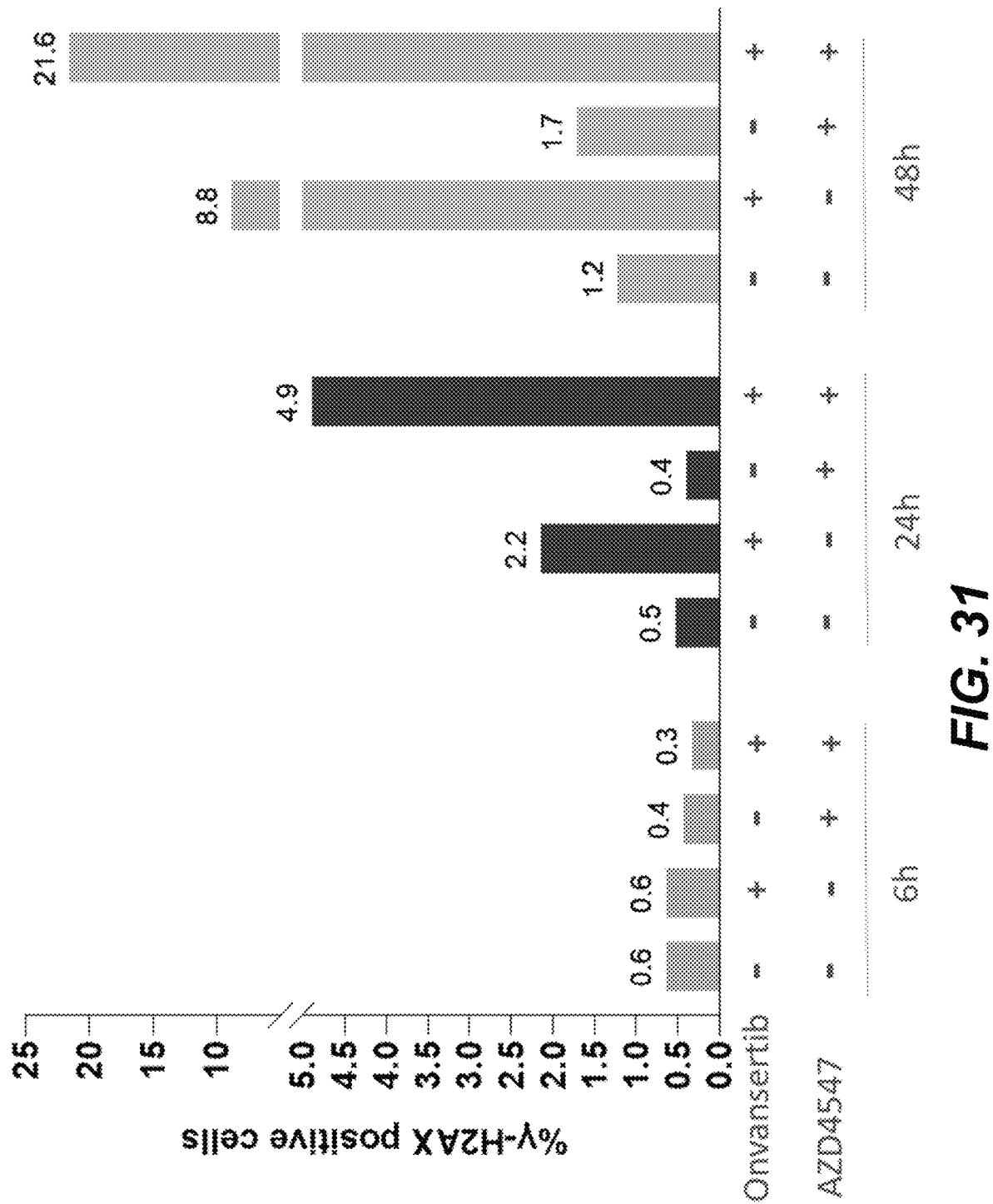
FIG. 31 depicts non-limiting exemplary embodiments and data related to the percentage of γ-H2AX cells assessed by flow cytometry at different time points after treatments (single treatment with onvansertib or AZD4547 or combined treatment with onvansertib or AZD45417), compared to cells with no treatment and showing that the combination induces increased DNA damage compared to DMSO and single agents.

Moreover, the combination of onvansertib and AZD4547 induced increased DNA damage compared to vehicle and single agents in NCI-H1703 cells. FIG. 29 shows the assessment of γ-H2AX at 6 h, 24 h, and 48 h after different treatments using Western Blot. The relative intensity of band shown in FIG. 29 is quantified and shown in FIG. 30. The amounts of γ-H2AX were about the same after both single treatments with either onvansertib or AZD4547 and combined treatment, compared to cells receiving no treatment (FIGS. 29 and 30). At both 24 h and 48 h, single treatment with onvansertib increased the γ-H2AX, compared to cells receiving single treatment with AZD4547 or DMSO (FIGS. 29 and 30). Combined treatment with onvansertib and AZD4547 further increased the γ-H2AX at both 24 h and 48 h after treatments, compared to single treatment with onvansertib (FIGS. 29 and 30). To confirm the above observations, percentage of γ-H2AX positive cells was quantified using flow cytometry. The percentages of γ-H2AX positive cells were about the same after both single treatments with either onvansertib or AZD4547 and combined treatment, compared to cells receiving DMSO treatment (FIG. 31). At both 24 h and 48 h, single treatment with onvansertib increased the percentage of γ-H2AX positive cells, compared to cells receiving single treatment with AZD4547 or DMSO (FIG. 31). Combined treatment with onvansertib and AZD4547 further increased the percentage of γ-H2AX positive cells at both 24 h and 48 h after treatment, compared to single treatment with onvansertib (FIG. 31). In FIG. 27-FIG. 31, the concentration of onvansertib used was 50 nM and the concentration of AZD4547 was 2.5 μM.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of therapeutically treating lung cancer or gastric cancer, the method comprising: administrating a fibroblast growth factor receptor (FGFR) inhibitor and onvansertib to a subject with the lung cancer or the gastric cancer, thereby inhibiting progression of the lung cancer or the gastric cancer.

2. The method of claim 1, wherein the subject has lung cancer.

3. The method of claim 1, comprising identifying a subject with the lung cancer or the gastric cancer cancer as a subject having FGFR-amplified cancer and/or cancer that comprises FGFR overexpression, and administering FGFR inhibitor and onvansertib to the subject with the lung cancer or the gastric cancer.

4. The method of claim 1, wherein onvansertib and the FGFR inhibitor are co-administered simultaneously or administered sequentially.

5. The method of claim 1, wherein the inhibition of the lung cancer or the gastric cancer progression is greater than the combined inhibition of progression caused by the FGFR inhibitor alone plus onvansertib alone.

6. The method of claim 1, wherein the subject has received a prior FGFR inhibitor treatment, and wherein the subject did not respond to treatment with the FGFR inhibitor alone or is known to be resistant to an FGFR inhibitor therapy.

7. The method of claim 1, wherein the FGFR inhibitor and onvansertib are each administered to the subject in a cycle of at least twice within a week.

8. The method of claim 1, wherein onvansertib is administered on at least four days in the cycle.

9. The method of claim 1, wherein the FGFR inhibitor is selective and/or specific for one or more FGFRs.

10. The method of claim 1, wherein onvansertib is administered at 6 mg/m$^2$-90 mg/m$^2$.

11. The method of claim 1, wherein the subject has received at least one prior lung cancer or gastric cancer, treatment.

12. The method of claim 1, wherein the subject was in remission for the lung cancer or the gastric cancer.

13. The method of claim 1, further comprising determining the lung cancer or the gastric cancer status of the subject.

14. A method of sensitizing lung cancer or gastric cancer cells to an FGFR inhibitor, the method comprising: contacting the lung cancer or gastric cancer cells with a composition comprising onvansertib, thereby sensitizing the lung cancer or gastric cancer cells to the FGFR inhibitor.

15. The method of claim 14, wherein contacting the lung cancer or gastric cancer cells with the composition occurs in vitro, ex vivo, and/or in vivo.

16. The method of claim 14, wherein contacting the lung cancer or gastric cancer cells with the composition is in a subject.

17. The method of claim 14, comprising determining sensitization of the lung cancer or gastric cancer cells to the FGFR inhibitor after being contacted with the composition.

18. The method of claim 14, comprising contacting the lung cancer or gastric cancer cells with the FGFR inhibitor.

* * * * *